US012691185B2

(12) United States Patent
Deblonde et al.

(10) Patent No.: US 12,691,185 B2
(45) Date of Patent: Jul. 28, 2026

(54) METHODS OF SEQUESTERING TARGET ELEMENTS

(71) Applicants: LAWRENCE LIVERMORE NATIONAL SECURITY, LLC, Livermore, CA (US); THE PENN STATE RESEARCH FOUNDATION, University Park, PA (US)

(72) Inventors: Gauthier Deblonde, Livermore, CA (US); Yongqin Jiao, Livermore, CA (US); Dan McFarland Park, Livermore, CA (US); Joseph Anthony Mattocks, University Park, PA (US); Joseph Alfred Cotruvo, Jr., University Park, PA (US)

(73) Assignees: LAWRENCE LIVERMORE NATIONAL SECURITY, LLC, Livermore, CA (US); THE PENN STATE RESEARCH FOUNDATION, University Park, PA (US)

( * ) Notice: Subject to any disclaimer, the term of this patent is extended or adjusted under 35 U.S.C. 154(b) by 281 days.

(21) Appl. No.: 17/175,228

(22) Filed: Feb. 12, 2021

(65) Prior Publication Data

US 2021/0268132 A1 Sep. 2, 2021

Related U.S. Application Data

(60) Provisional application No. 62/976,149, filed on Feb. 13, 2020.

(51) Int. Cl.
*A61K 51/08* (2006.01)
*C22B 3/24* (2006.01)
*C22B 59/00* (2006.01)

(52) U.S. Cl.
CPC ................ *A61K 51/08* (2013.01); *C22B 3/24* (2013.01); *C22B 59/00* (2013.01)

(58) Field of Classification Search
CPC .......... A61K 51/08; C22B 3/24; C22B 59/00; C22B 58/00; C22B 61/00; C02F 1/00; C02F 1/001; C02F 1/006; C02F 1/004; C02F 2001/422; C02F 2001/425; C02F 1/444; C02F 1/441; C02F 1/442; C02F 1/44; C02F 1/46; C02F 1/461; C02F 1/447
USPC .............................. 424/1.11, 1.49, 1.65, 1.69
See application file for complete search history.

(56) References Cited

U.S. PATENT DOCUMENTS

| | | | |
|---|---|---|---|
| 5,441,643 A | 8/1995 | Spears et al. | |
| 5,665,865 A | 9/1997 | Lerner et al. | |
| 10,413,621 B2 | 9/2019 | Basilion et al. | |
| 10,442,860 B2 | 10/2019 | Bedi et al. | |
| 10,537,644 B2 | 1/2020 | Huang et al. | |
| 2007/0116782 A1 | 5/2007 | Abrams et al. | |
| 2010/0137346 A1 | 6/2010 | Bergeron, Jr. | |
| 2014/0141044 A1 | 5/2014 | Bhatt et al. | |
| 2016/0177419 A1 | 6/2016 | Hatanaka et al. | |
| 2017/0101698 A1 | 4/2017 | Karamalidis et al. | |
| 2018/0195147 A1 | 7/2018 | Jiao et al. | |
| 2022/0348619 A1* | 11/2022 | Boyle ................. C07K 14/435 |

FOREIGN PATENT DOCUMENTS

| | | |
|---|---|---|
| CN | 105612426 A | 5/2016 |
| JP | 2016047810 A | 4/2016 |
| JP | 2017193518 A | 10/2017 |
| WO | 9116912 A1 | 11/1991 |
| WO | 03014373 A2 | 2/2003 |
| WO | 2010099536 A2 | 9/2010 |
| WO | 2015021143 A1 | 2/2015 |
| WO | 2015111407 A1 | 7/2015 |
| WO | 2017216384 A1 | 12/2017 |
| WO | 2020051274 A2 | 3/2020 |

OTHER PUBLICATIONS

Aisen et al., Stoichiometric and site characteristics of the binding of iron to human transferrin, J. Biol. Chem., 253(6):1930-1937 (1978).
Allred et al., Siderocalin-mediated recognition, sensitization, and cellular uptake of actinides, PNAS, 112(33):10342-10347 (2015).
Brayshaw et al., Lanthanides compete with calcium for binding to cadherins and inhibit cadherin-mediated cell adhesion, Metallomics, 11(5):914-924 (2019).
Calisti et al., Engineered ferritin for lanthanide binding, Plos One, 13(8):e0201859 (2018).
Chaudhuri et al., Characterization of lanthanide ion binding to the EF-hand protein S100 beta by luminescence spectroscopy, Biochemistry, 36(12):9674-9680 (1997).
Cook et al., Structural basis for rare earth element recognition by methylobacterium extorquens lanmodulin, Biochemistry, 58(2):120-125 (2019).
Correnti et al., Mammalian siderophores, siderophore-binding lipocalins, and the labile iron pool, J. Biol. Chem., 287(17):13524-13531 (2012).
Cotruvo et al., Lanmodulin: A highly selective lanthanide-binding protein from a lanthanide-utilizing bacterium, J. Am. Chem. Soc., 140(44):15056-15061 (2018).
Dautry-Varsat et al., pH and the recycling of transferrin during receptor-mediated endocytosis, PNAS, 80(8):2258-2262 (1983).
Deblonde et al., Solution thermodynamic stability of complexes formed with the octadentate hydroxypyridinonate ligand 3,4,3-LI(1,2-HOPO): a critical feature for efficient chelation of lanthanide(IV) and actinide(IV) ions, Inorg. Chem., 52(15):8805-8811 (2013).

(Continued)

*Primary Examiner* — D. L. Jones
(74) *Attorney, Agent, or Firm* — Zilka-Kotab, P.C.

(57) ABSTRACT

Provided herein are methods of sequestering target elements (e.g., rare earth elements and/or radiometals) from a sample, methods of purifying target elements from samples, pharmaceutical compositions comprising target elements, and methods of treating a subject with said pharmaceutical compositions.

10 Claims, 49 Drawing Sheets

Specification includes a Sequence Listing.

(56) References Cited

OTHER PUBLICATIONS

Du et al., Complexation of ytterbium to human transferrin and its uptake by K562 cells, European Journal of Biochemistry, 269(24):6082-6090 (2002).

Gans et al., Investigation of equilibria in solution, Determination of equilibrium constants with the HYPERQUAD suite of programs, Talanta, 43(10):1739-1753 (1996).

Haiech et al., Effects of cations on affinity of calmodulin for calcium: ordered binding of calcium ions allows the specific activation of calmodulin-stimulated enzymes, Biochemistry, 20(13):3890-3897 (1981).

Harris et al., Binding constants for neodymium(III) and samarium(III) with human serum transferrin, Inorg. Chem., 25:2041-2045 (1986).

Harris et al., Difference ultraviolet spectroscopic studies on the binding of lanthanides to human serum transferrin, Inorg. Chem., 31:5001-5006 (1992).

Johnson, S. G. NIST46. Nist https://www.nist.gov/srd/nist46 (2013).

Kim et al., High-affinity recognition of lanthanide(III) chelate complexes by a reprogrammed human lipocalin 2, J. Am. Chem. Soc., 131(10):3565-3576 (2009).

Martin et al., Double-lanthanide-binding tags: design, photophysical properties, and NMR applications, J. Am. Chem. Soc., 129(22):7106-7113 (2007).

Nitz et al., Structural origin of the high affinity of a chemically evolved lanthanide-binding peptide, Angewandte Chemie International Edition, 43(28):3682-3685 (2004).

Özçubukçu et al., Selective recognition of americium by peptide-based reagents, Inorg. Chem., 50(17):7937-7939 (2011).

Park et al., Bioadsorption of rare earth elements through cell surface display of lanthanide binding tags, Environ. Sci. Technol., 50(5):2735-2742 (2016).

Pham et al., A macrocyclic chelator with unprecedented Th4+ affinity, J. Am. Chem. Soc., 136(25):9106-9115 (2014).

Sun et al., Transferrin as a metal ion mediator, Chem. Rev., 99(9):2817-2842 (1999).

Ye et al., Probing site-specific calmodulin calcium and lanthanide affinity by grafting, J. Am. Chem. Soc., 127(11):3743-3750 (2005).

Deblonde et al., Selective and efficient biomacromolecular extraction of rare-earth elements using lanmodulin, Inor. Chem., 50:1-13 (2020).

International Application No. PCT/US21/17973 International Search Report mailed Jun. 7, 2021.

Mattocks et al.,A Selective, Protein-Based Fluorescent Sensor with Picomolar Affinity for Rare Earth Elements, JACS, 141:2857-2861 (2019).

Maniccia et al. "Inverse tuning of metal binding affinity and protein stability by altering charged coordination residues in designed calcium binding proteins," PMC Biophysics, vol. 2, No. 11, 2009, pp. 1-16.

Kolobynina et al., "Emerging roles of the single EF-hand Ca2+ sensor tescalcin in the regulation of gene expression, cell growth and differentiation," Journal of Cell Science, vol. 129, 2016, pp. 3533-3540.

Bogdanov et al., "Design of metal-binding green fluorescent protein variants," Biochimica et Biophysica Acta, vol. 1397, 1998, pp. 56-64.

Wang et al., "A single molecular probe for multi-analyte (Cr3+, Al3+ and Fe3+) detection in aqueous medium and its biological application," Chemical Communications, vol. 50, 2014, pp. 12258-12261.

Deblonde et al. "Receptor recognition of transferrin bound to lanthanides and actinides: a discriminating step in cellular acquisition of f-block metals," Metallomics, vol. 5, 2013, pp. 619-626.

Vuilleumier et al. "Conserved hypothetical protein; putative exported protein [Methylorubrum extorquens AM1]," GenBank: ACS39628. 1, 2014.

Kisselev et al., "Polypeptide Release Factors in Prokaryotes and Eukaryotes: Same Function, Different Structure," Structure, vol. 10, 2002, pp. 8-9.

Witkowski et al., "Conversion of a β-Ketoacyl Synthase to a Malonyl Decarboxylase by Replacement of the Active-Site Cysteine with Glutamine," Biochemistry, vol. 38, 1999, pp. 11643-11650.

Whisstock et al., "Prediction of protein function from protein sequence and structure," Quarterly Review of Biophysics, vol. 36, No. 3, 2003, pp. 307-340.

Devos et al., "Practical Limits of Function Prediction," Proteins: Structure, Function, and Genetics, vol. 41, 2000, pp. 98-107.

Xue et al., "Protein MRI contrast agent with unprecedented metal selectivity and sensitivity for liver cancer imaging," PNAS, vol. 112, No. 21, 2015, pp. 6607-6612.

Altschul et al., "Basic Local Alignment Search Tool," Journal of Molecular Biology, vol. 215, No. 3, 1990, pp. 403-410.

Altschul et al., "Gapped BLAST and PSI-BLAST: a new generation of protein database search programs," Nucleic Acids Research, vol. 25, No. 17, 1997, pp. 3389-3402.

Farrell et al., "β-Lactoglobulin and α-lactalbumin as potential modulators of mammary cellular activity," Protoplasma, vol. 159, 1990, pp. 157-167.

Gardner et al., "Manipulating the yeast genome: deletion, mutation, and tagging by PCR," Methods in Molecular Biology, vol. 1205, 2014, pp. 45-78.

Goldenzweig et al., "Automated Structure- and Sequence-Based Design of Proteins for High Bacterial Expression and Stability," Molecular Cell, vol. 63, No. 2, 2016, pp. 337-346.

Haas et al. "De novo transcript sequence reconstruction from RNA-seq using the Trinity platform for reference generation and analysis," Nature Protocols, vol. 8, No. 8, 2013, pp. 1494-1512.

Hebenstreit et al., "Structural changes in calcium-binding allergens: use of circular dichroism to study binding characteristics," Allergy, vol. 60, No. 9, 2005, pp. 1208-1211.

Ikura et al., "The role of calcium-binding proteins in the control of transcription: structure to function," BioEssays, vol. 24, No. 7, 2002, pp. 625-636.

Karlin et al., "Applications and statistics for multiple high-scoring segments in molecular sequences," Proc. Natl. Acad. Sci. USA, vol. 90, No. 12, 1993, pp. 5873-5877.

Karlin et al., "Methods for assessing the statistical significance of molecular sequence features by using general scoring schemes," Proc. Natl. Acad. Sci. USA, vol. 87, No. 6, 1990, pp. 2264-2268.

Kunkel, "Rapid and efficient site-specific mutagenesis without phenotypic selection," Proc. Natl. Acad. Sci. USA, vol. 82, No. 2, 1985, pp. 488-492.

Lewit-Bentley et al., "EF-hand calcium-binding proteins," Current Opinion in Structural Biology, vol. 10, No. 6, 2000, pp. 637-643.

Li et al., "MEGAHIT: an ultra-fast single-node solution for large and complex metagenomics assembly via succinct de Bruijn graph," Bioinformatics, vol. 31, No. 10, 2015, pp. 1674-1676.

Lim et al., "Lanthanide-binding peptides and the enzymes that Might Have Been," Cellular and Molecular Life Sciences, vol. 61, No. 17, 2004, pp. 2184-2188.

Maki et al., "Structures, functions and molecular evolution of the penta-EF-hand Ca2+-binding proteins," Biochimica et Biophysica Acta, vol. 1600, No. 1-2, 2002, pp. 51-60.

Needleman et al., "A general method applicable to the search for similarities in the amino acid sequence of two proteins," Journal of Molecular Biology, vol. 48, No. 3, 1970, pp. 443-453.

Poussu et al., "A gene truncation strategy generating N- and C-terminal deletion variants of proteins for functional studies: mapping of the Sec1p binding domain in yeast Mso1p by a Mu in vitro transposition-based approach," Nucleic Acids Research, vol. 33, No. 12, 2005, pp. e104.

Rasmussen et al., "Ca2+ and Na+ binding to high affinity sites of calcium-containing proteins measured by capillary electrophoresis," Journal of Inorganic Biochemistry, vol. 95, No. 2-3, 2003, pp. 113-123.

Saboury et al., "Application of a simple calorimetric data analysis on the binding study of calcium ions by human growth hormone," Journal of Thermal Analysis and Calorimetry, vol. 83, No. 1, 2006, pp. 175-179.

(56) References Cited

OTHER PUBLICATIONS

Sievers et al., "Fast, scalable generation of high-quality protein multiple sequence alignments using Clustal Omega," Molecular Systems Biology, vol. 7, Article No. 539, 2011, pp. 1-6.

Smith et al., "Identification of common molecular subsequences," Journal of Molecular Biology, vol. 147, No. 1, 1981, pp. 195-197.

Sonnhammer et al., "Pfam: A Comprehensive Database of Protein Domain Families Based on Seed Alignments," Proteins: Structure, Function, and Genetics, vol. 28, No. 3, 1997, pp. 405-420.

Stormo et al., "Use of the 'Perceptron' algorithm to distinguish translational initiation sites in *E. coli,*" Nucleic Acids Research, vol. 10, No. 9, 1982, pp. 2997-3011.

Vetter et al., "Novel aspects of calmodulin target recognition and activation," European Journal of Biochemistry, vol. 270, No. 3, 2003, pp. 404-414.

Weiner et al., "Rapid motif-based prediction of circular permutations in multi-domain proteins," Bioinformatics, vol. 21, No. 7, 2005, pp. 932-937.

Yu et al., "Circular permutation: a different way to engineer enzyme structure and function," Trends in Biotechnology, vol. 29, No. 1, 2011, pp. 18-25.

Office Action from Canadian Application No. 3,170,828, dated Feb. 17, 2026, 5 pages.

* cited by examiner nformation

SEQUENCE LISTING

```
<160> NUMBER OF SEQ ID NOS: 5

<210> SEQ ID NO 1
<211> LENGTH: 111
<212> TYPE: PRT
<213> ORGANISM: Artificial Sequence
<220> FEATURE:
<223> OTHER INFORMATION: Synthetic polypeptide

<400> SEQUENCE: 1

Pro Thr Thr Thr Thr Lys Val Asp Ile Ala Ala Phe Asp Pro Asp Lys
1               5                   10                  15

Asp Gly Thr Ile Asp Leu Lys Glu Ala Leu Ala Ala Gly Ser Ala Ala
                20                  25                  30

Phe Asp Lys Leu Asp Pro Asp Lys Asp Gly Thr Leu Asp Ala Lys Glu
            35                  40                  45

Leu Lys Gly Arg Val Ser Glu Ala Asp Leu Lys Lys Leu Asp Pro Asp
        50                  55                  60

Asn Asp Gly Thr Leu Asp Lys Lys Glu Tyr Leu Ala Ala Val Glu Ala
65                  70                  75                  80

Gln Phe Lys Ala Ala Asn Pro Asp Asn Asp Gly Thr Ile Asp Ala Arg
                85                  90                  95

Glu Leu Ala Ser Pro Ala Gly Ser Ala Leu Val Asn Leu Ile Arg
                100                 105                 110

<210> SEQ ID NO 2
<211> LENGTH: 12
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
```

-continued

```
<223> OTHER INFORMATION: Xaa is D or N
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: MISC_FEATURE
<222> LOCATION: (3)..(3)
<223> OTHER INFORMATION: Xaa is D or N
<220> FEATURE:
<221> NAME/KEY: misc_feature
<222> LOCATION: (4)..(4)
<223> OTHER INFORMATION: Xaa can be any naturally occurring amino acid
<220> FEATURE:
<221> NAME/KEY: MISC_FEATURE
<222> LOCATION: (5)..(5)
<223> OTHER INFORMATION: Xaa is D or N
<220> FEATURE:
<221> NAME/KEY: misc_feature
<222> LOCATION: (6)..(8)
<223> OTHER INFORMATION: Xaa can be any naturally occurring amino acid
<220> FEATURE:
<221> NAME/KEY: MISC_FEATURE
<222> LOCATION: (9)..(9)
<223> OTHER INFORMATION: Xaa is D or E
<220> FEATURE:
<221> NAME/KEY: misc_feature
<222> LOCATION: (10)..(10)
<223> OTHER INFORMATION: Xaa can be any naturally occurring amino acid
<220> FEATURE:
<221> NAME/KEY: MISC_FEATURE
<222> LOCATION: (11)..(11)
<223> OTHER INFORMATION: Xaa is D or E
<220> FEATURE:
<221> NAME/KEY: MISC_FEATURE
<222> LOCATION: (12)..(12)
<223> OTHER INFORMATION: Xaa is D or E

<400> SEQUENCE: 2

Xaa Xaa Xaa Xaa Xaa Xaa Xaa Xaa Xaa Xaa Xaa Xaa
1               5                   10

<210> SEQ ID NO 3
<211> LENGTH: 107
<212> TYPE: PRT
<213> ORGANISM: RH AL1

<400> SEQUENCE: 3

Ala Lys Met Asp Met Lys Ala Ile Asp Pro Asp Ser Asp Gly Thr Val
1               5                   10                  15

Ser Leu Ala Glu Ala Gln Asp Ala Ala Ala Lys Lys Phe Ala Ala Met
            20                  25                  30

Asp Pro Asp Asn Asp Gly Thr Ile Asp Leu Lys Glu Ala Lys Gly Lys
        35                  40                  45

Met Ala Lys Ala Lys Phe Lys Lys Thr Asp Ala Asp Asn Asp Gly Thr
    50                  55                  60

Val Asp Lys Ala Glu Tyr Ser Ala Leu Val Glu Ser Ala Phe Lys Ala
65                  70                  75                  80

Ala Asp Pro Asp Gly Asp Gly Thr Leu Asp Ala Lys Glu Leu Lys Thr
                85                  90                  95

Pro Ala Gly Gln Lys Leu Leu Ser Leu Ile Gln
            100                 105

<210> SEQ ID NO 4
<211> LENGTH: 110
<212> TYPE: PRT
<213> ORGANISM: Hansschlegelia sp

<400> SEQUENCE: 4
```

```
Ala Ser Gly Ala Asp Ala Leu Lys Ala Leu Asn Lys Asp Asn Asp Asp
1               5                   10                  15

Ser Leu Glu Ile Ala Glu Val Ile His Ala Gly Ala Thr Thr Phe Thr
            20                  25                  30

Ala Ile Asn Pro Asp Gly Asp Thr Thr Leu Glu Ser Gly Glu Thr Lys
        35                  40                  45

Gly Arg Leu Thr Glu Lys Asp Trp Ala Arg Ala Asn Lys Asp Gly Asp
        50                  55                  60

Gln Thr Leu Glu Met Asp Glu Trp Leu Lys Ile Leu Arg Thr Arg Phe
65                  70                  75                  80

Lys Arg Ala Asp Ala Asn Lys Asp Gly Lys Leu Thr Ala Ala Glu Leu
                85                  90                  95

Asp Ser Lys Ala Gly Gln Gly Val Leu Val Met Ile Met Lys
                100                 105                 110

<210> SEQ ID NO 5
<211> LENGTH: 96
<212> TYPE: PRT
<213> ORGANISM: Xanthomonas axonopodis

<400> SEQUENCE: 5

Ala Gln Ala Gln Val Gln Val Gln Asp Ser Gln Gln Tyr Leu Gln Arg
1               5                   10                  15

Met Asp Thr Asp Gly Asp Gly Arg Val Ser Leu Asp Glu Tyr Leu Ala
            20                  25                  30

Trp Met Ser Tyr Ala Phe Asp Gln Arg Asp Thr Asp His Asp Gly Val
        35                  40                  45

Leu Gln Gly Asp Glu Leu Pro Gly Arg Arg Gly Lys Pro Ile Thr Arg
        50                  55                  60

Ala Ala His Arg Ala Thr Leu Ile Ala Arg Phe Ala Arg Gln Asp Ala
65                  70                  75                  80

Asn Gly Asp Gly Tyr Leu Ser Ala Arg Glu Leu Leu Ala Pro Pro Arg
                85                  90                  95
```

METHODS OF SEQUESTERING TARGET ELEMENTS

STATEMENT OF US GOVERNMENT SUPPORT

This invention was made with Government support under Contract No. DE-AC52-07NA27344 and DE-SC0021007 awarded by the United States Department of Energy. The Government has certain rights in the invention.

INCORPORATION BY REFERENCE OF MATERIAL SUBMITTED ELECTRONICALLY

A Sequence Listing has been submitted electronically in TXT format and is hereby incorporated by reference in its entirety. The TXT copy, created on May 15, 2025, is named 13517_SubSeqListing.txt and is 5,268 bytes in size.

BACKGROUND

Proteins are ubiquitous in the environment and serve a wide range of functions that are vital to microorganisms, plants, insects, and mammals, including humans. Evolution has led certain natural proteins to play a central role in the biogeochemistry of specific nutrients. While the binding of naturally abundant s-, d-, or p-block elements to metalloproteins seems logical, the chelation of f-block elements by natural macromolecules is, at first sight, surprising. The uptake of rare earth elements by metalloproteins had rarely been studied. Moreover, the chemistry of 4f-elements readily differs from that of other blocks of the periodic table with almost no redox chemistry under natural conditions (except for the $Ce^{4+}/Ce^{3+}$ couple), a coordination number of 8 to 10 compared to the usual 4 to 6, and a large ionic radius (about 1 Å) relative to d-block metals. There is a lack of naturally efficient rare-earth elements (REE)-binding macromolecules which has led the industry and associated research field to generally ignore proteins for the REE life cycle and favor small manmade chelators instead. In addition, there is a need for naturally efficient radiometal (RM)-binding macromolecules.

The emergence of bio-sourced or bio-inspired chelators for selective REE and/or RM sequestration could offer a new avenue toward a more sustainable REE sector and a more sustainable RM sector. Leveraging biomolecules for metal extraction technologies is rather appealing since most biochemical processes occur with quantitative yields, fast kinetics, and extremely high selectivity and fidelity.

SUMMARY

Provided herein are methods of sequestering target elements (e.g., rare earth elements, radiometals, or Bi, Tl, and In) from a sample, methods of purifying a target element from samples, pharmaceutical compositions comprising target elements, and methods of treating a subject with said pharmaceutical compositions.

The disclosure also provides methods of sequestering a target element (TE) from a sample comprising contacting the sample and lanmodulin protein (LanM) in a first solution such that the target element binds to the lanmodulin to form TE-LanM, wherein the first solution is aqueous and has a pH of 2.5 to 6.5, and wherein the TE is one or more of a rare-earth element (REE), Bi, Tl, and In and the LanM protein comprises at least one LanM unit; recovering the TE-LanM from the first solution to form a second solution comprising the TE-LanM; adjusting the pH of the second solution to less than 2.5 such that the TE desorbs from the LanM; separating the LanM and the TE; and repeating the contacting, recovering, and adjusting steps with a second sample and the LanM at least once.

The disclosure provides methods of sequestering a rare earth element from a sample comprising contacting the sample and lanmodulin protein (LanM) in a first solution such that the rare earth element (REE) binds to the lanmodulin to form REE-LanM, wherein the first solution is aqueous and has a pH of 2.5 to 6.5 and the LanM protein comprises at least one LanM unit; recovering the REE-LanM from the first solution to form a second solution comprising the REE-LanM; adjusting the pH of the second solution to less than 2.5 such that the REE desorbs from the LanM; separating the LanM and the REE; and repeating the contacting, recovering, and adjusting steps with a second sample and the LanM at least once.

In embodiments, the REE comprises one or more of Sc, Y, La, Ce, Pr, Nd, Pm, Sm, Eu, Gd, Tb, Dy, Ho, Er, Tm, Yb, and Lu. In embodiments, each LanM unit binds up to four REEs. In embodiments, the sample further comprises non-target elements (non-TEs). In embodiments, the non-target elements comprise Li, Na, K, Mg, Ca, Sr, Rb, Cs, Ba, Al, Si, Mn, Fe, Co, Ni, Cu, Zn, Ti, Sn, V, or a combination thereof. In embodiments, the sample is an industrial feedstock comprising TEs and non-TEs. In embodiments, the non-TEs can include one or more radioisotopes that do not bind to LanM or LanM otherwise has a weak affinity for, such as Ra-224, Ra-228, Ti-44, Np-239, and Pa-231 In embodiments, the industrial feedstock is non-combusted coal, electronic waste, geothermal brine, waste streams, radioisotope production compositions, industrial effluents, ore deposits (e.g. bastnaesite, monazite, allanite, and the like), or a combination thereof. In embodiments, the TE comprises a radioactive isotope. In embodiments, the radioactive isotope comprises $^{44}Sc$, $^{47}Sc$, $^{90}Y$, $^{134}Ce$, $^{134}La$, $^{86}Y$, $^{88}Y$, $^{139}Ce$, $^{149}Tb$, $^{153}Gd$, $^{17}Lu$, $^{165}Dy$, $^{152}Eu$, $^{153}Sm$, $^{147}Pm$, $^{166}Ho$, $^{169}Yb$, $^{176}Yb$, $^{212}Bi$, $^{213}Bi$, $^{225}Ac$, $^{226}Ac$, $^{228}Ac$, $^{227}Ac$, $^{239}Pu$, $^{240}Pu$, $^{241}Pu$, $^{244}Pu$, $^{241}Am$, $^{243}Am$, $^{244}Cm$, $^{246}Cm$, $^{248}Cm$, $^{250}Bk$, $^{249}Bk$, $^{248}Bk$, $^{247}Bk$, $^{252}Cf$, $^{254}Es$, $^{255}Fm$, $^{152}Tb$, $^{155}Tb$, $^{161}Tb$, or a combination thereof. In embodiments, the LanM is bound to a support (LanM-support). In embodiments, the support comprises a sponge, a powder, a resin, a filter, thin film, gel, or a combination thereof.

Also provided herein are methods of purifying a target element (TE) from an industrial feedstock comprising contacting the industrial feedstock and lanmodulin protein (LanM) such that the TE binds to LanM to form TE-LanM, and the LanM protein comprises at least one LanM unit; and recovering the TE-LanM from the industrial feedstock to form a solution comprising the TE-LanM; wherein the industrial feedstock comprises TE and non-target elements. In embodiments, the method further comprises adjusting the pH of the solution comprising the TE-LanM to less than 2.5, such that the TE desorbs from the LanM; and separating the LanM and the TE. In embodiments, the methods further comprise repeating the contacting, recovering, and adjusting steps with a second industrial feedstock and the LanM at least once. In embodiments, the industrial feedstock is non-combusted coal, electronic waste, geothermal brine, waste streams, radioisotope production compositions, industrial effluents, ore deposits, or a combination thereof.

Also provided herein are REE pharmaceutical compositions comprising (i) an REE bound to a modified lanmodulin protein (LanM) and (ii) at least one pharmaceutically acceptable excipient, wherein the modified LanM is LanM modified with a targeting moiety. In embodiments, the targeting moiety is an antibody, a peptide, or a small organic molecule. In addition to pharmaceutical compositions having a rare earth element bound to a modified lanmodulin protein, it is also contemplated herein that the pharmaceutical composition could include instead or additionally one or more of Bi, Tl, and In bound to the modified lanmodulin protein.

Also provided herein are methods of treating cancer in a subject suffering therefrom, comprising administering the pharmaceutical composition disclosed herein. In embodiments, the cancer is liver cancer, skin cancer, bone metastases, brain cancer glioblastoma, lymphoma, colon cancer, prostate cancer, or leukemia.

Also provided herein are methods of imaging a tumor in a subject, comprising administering the pharmaceutical composition disclosed herein to the subject and performing an imaging modality on the subject. In embodiments, the imaging modality is selected from the group consisting of magnetic resonance imaging (MRI), positron emission tomography (PET), positron emission tomography/computed tomography (PET/CT), positron emission tomography/magnetic resonance imaging (PET/MRI), and single-photon emission computerized tomography (SPECT).

Further provided herein are methods of preparing a REE pharmaceutical composition comprising purifying the REE by contacting the REE and a LanM such that the REE binds to the lanmodulin to form REE-LanM, and the LanM protein comprises at least one LanM unit; recovering the REE-LanM to form a solution comprising the REE-LanM; adjusting the pH of the solution comprising the REE-LanM to less than 2.5, such that the REE desorbs from the LanM; isolating the desorbed REE; and admixing the desorbed REE and at least one pharmaceutically acceptable excipient to provide the REE pharmaceutical composition. The method can include purification, isolation and mixing with at least one pharmaceutically acceptable excipient of one or more of Bi, In, and Tl as an alternative to or in addition to the rare earth element.

Also provided herein are methods of purifying a TE from a pharmaceutical composition comprising contacting the pharmaceutical composition and LanM such that the TE binds to LanM to form TE-LanM, and the LanM protein comprises at least one LanM unit; and recovering the TE-LanM from the pharmaceutical composition to form a solution comprising the TE-LanM; wherein the pharmaceutical composition comprises TE and non-target elements.

Also provided herein are method of sequestering radiometals from a sample, methods of purifying radiometals from a mixture of metals, pharmaceutical compositions comprising rare earth elements, and methods of treating a subject with said pharmaceutical compositions.

The disclosure provides methods of sequestering a radiometal from a sample comprising contacting the sample and lanmodulin protein (LanM) in a first solution such that the radiometal (RM) binds to the lanmodulin to form RM-LanM, wherein the first solution is aqueous and has a pH of 2.5 to 10 and the LanM protein comprises at least one LanM unit; recovering the RM-LanM from the first solution to form a second solution comprising the RM-LanM; adjusting the pH of the second solution to less than 2.5 such that the RM desorbs from the LanM; separating the LanM and the RM; and repeating the contacting, recovering, and adjusting steps with a second sample and the LanM at least once.

Also provided herein are methods of purifying a radiometal (RM) from a mixture of metals comprising contacting a sample comprising the mixture of metals and lanmodulin protein, wherein the mixture of metals comprises a radiometal having a +3 oxidation state [RM (III)] and a metal having an oxidation state other than +3 [M (III*)]; such that the RM (III) binds to LanM to form RM (III)-LanM and the LanM protein comprises at least one LanM unit; and separating the RM (III)-LanM and the M (III*).

Also provided herein are RM pharmaceutical compositions comprising (i) an RM bound to a modified lanmodulin protein (LanM) and (ii) at least one pharmaceutically acceptable excipient, wherein the modified LanM is LanM modified with a targeting moiety. In embodiments, the targeting moiety is an antibody, a peptide, or a small organic molecule.

Also provided herein are methods of treating cancer in a subject suffering therefrom, comprising administering the RM pharmaceutical composition disclosed herein. In embodiments, the cancer is liver cancer, skin cancer, bone metastases, brain cancer glioblastoma, lymphoma, colon cancer, prostate cancer, or leukemia.

Also provided herein are methods of imaging a tumor in a subject, comprising administering the RM pharmaceutical composition disclosed herein to the subject and performing an imaging modality on the subject.

Further provided herein are methods of preparing a RM pharmaceutical composition comprising purifying the RM by contacting the RM and a LanM such that the RM binds to the lanmodulin to form RM-LanM; recovering the RM-LanM to form a solution comprising the RM-LanM and the LanM protein comprises at least one LanM unit; adjusting the pH of the solution comprising the RM-LanM to less than 2.5, such that the RM desorbs from the LanM; isolating the desorbed RM; and admixing the desorbed RM and at least one pharmaceutically acceptable excipient to provide the RM pharmaceutical composition.

Also provided herein is a kit or use in purifying metals, the kit comprising: lanmodulin protein; and, a filter with a molecular weight cut-off of about 0.5 kDa to about 11 kDa, a column, or a size-exclusion medium.

BRIEF DESCRIPTION OF FIGURES

FIG. 1A is an absorbance spectrum of wavelength 500 nm to 620 nm between the initial sample and the final sample. FIG. 1B is an absorbance spectrum of wavelength 720 nm to 840 nm between the initial sample and the final sample. FIG. 1C is an absorbance spectrum of wavelength 850 nm to 900 nm between the initial sample and the final sample. FIG. 1D is a graph of the absorbance and the molar ratio of EDTA/LanM at various wavelengths.

FIG. 2A is an absorbance spectrum of wavelength 430 nm to 510 nm of $Pr^{3+}$ compared to $Ho^{3+}$. FIG. 2B is a graph of the absorbance and the molar ratio of LanM/(Pr+Ho) at various wavelengths. FIG. 2C is an absorbance spectrum of wavelength 430 nm to 540 nm of $Pr^{3+}$ compared to $Er^{3+}$. FIG. 2D is a graph of the absorbance and the molar ratio of LanM/(Pr+Er) at various wavelengths.

FIG. 3A is an absorbance spectrum of $Er_4LanM$ exchanged with $La^{3+}$. FIG. 3B is an absorbance spectrum of $Er_4LanM$ exchanged with $Yb^{3+}$.

FIG. 5A is a series of absorbance spectra of Nd-LanM vs. $Ca^{2+}$, wherein the x-axis shows wavelength (nm) from 720 nm to 860 nm. FIG. 5B is a reference absorbance spectrum versus molarity of $Ca^{2+}$. FIG. 5C is a series of absorbance spectra of Nd-LanM vs. $Mg^{2+}$, wherein the x-axis shows wavelength (nm) from 720 nm to 860 nm. FIG. 5D is a reference absorbance spectrum versus molarity of $Mg^{2+}$. FIG. 5E is a series of absorbance spectra of Nd-LanM vs. $Zn^{2+}$, wherein the x-axis shows wavelength (nm) from 720 nm to 860 nm. FIG. 5F is a reference absorbance spectrum versus molarity of $Zn^{2+}$. FIG. 5G is a series of absorbance spectra of Nd-LanM vs. $Cu^{2+}$, wherein the x-axis shows wavelength (nm) from 720 nm to 860 nm. FIG. 5H is a reference absorbance spectrum versus molarity of $Cu^{2+}$.

FIG. 6A is a graph of the absorbance versus pH, the main spectral changes observed upon pH titration of Nd-LanM solutions. [Nd]=1 mM. [LanM]=0.25 mM. Buffer: 25 mM glycine, 25 mM $KCH_3COO$, 50 mM KCl. Full absorbance spectra and similar data obtained with $Pr^{3+}$, $Er^{3+}$, and $Ho^{3+}$ are given in FIG. 7A-FIG. 7H; FIG. 6B is a graph of the hydrodynamic radius (nm) versus pH for Nd-LanM solutions. The hydrodynamic diameter of Nd-LanM measured by DLS as a function of pH. [Nd]=600 μM. [LanM]=100 μM. T=25° C. Error bars correspond to the averaged peak width (8 measurements). The height of the markers is higher than the standard deviation of the average size; FIG. 6C is a graph showing the size-exclusion ultracentrifugation of REE-LanM samples as function of pH using individual REE solution. [REE]$_{initial}$=30 μM. [LanM]=10 μM. Filtration performed with 3 kDa MWCO spin filters. Arsenazo analyses; FIG. 6D is a graph showing the size-exclusion ultracentrifugation of REE-LanM samples at as function of pH using an equimolar mixture of REEs. [REE]$_{total}$=200 μM. [LanM]=50 μM. ICP-MS analyses.

FIG. 7A is an absorbance spectrum of the Er-LanM solution at varying pHs. FIG. 7B is a graph of absorbance versus pH of the Er-LanM solution at varying pHs. FIG. 7C is an absorbance spectrum of the Nd-LanM solution at varying pHs. FIG. 7D is a graph of absorbance versus pH of the Nd-LanM solution at varying pHs. FIG. 7E is an absorbance spectrum of the Ho-LanM solution at varying pHs. FIG. 7F is a graph of absorbance versus pH of the Ho-LanM solution at varying pHs. FIG. 7G is an absorbance spectrum of the Pr-LanM solution at varying pHs. FIG. 7H is a graph of absorbance versus pH of the Pr-LanM solution at varying pHs.

FIG. 8A is a series of absorbance spectra. FIG. 8B is a graph of the wavelength of maximum absorbance.

FIG. 9A is an absorbance spectrum of the ligand-ligand competition titration between EDTA and acid-treated Nd-LanM. FIG. 9B is a graph of the absorbance versus the molar ratio of EDTA/LanM of the ligand-ligand competition titration between EDTA and acid-treated Nd-LanM. FIG. 9C is an absorbance spectrum of the ligand-ligand competition titration between EDTA and untreated Nd-LanM. FIG. 9D is a graph of the absorbance versus the molar ratio of EDTA/LanM of the ligand-ligand competition titration between EDTA and untreated Nd-LanM.

FIG. 10A-FIG. 10D shows the resilience of LanM to repeated acid attacks. Absorbance spectra of $Er^{3+}$-LanM and $Nd^{3+}$-LanM systems following acid-base pH cycles (pH 1.8 to 5). Solid curves: $Ln^{3+}$ bound to LanM (pH>2). Dotted curves: $Ln^{3+}$ released from LanM (pH<2). % REE bound to LanM calculated based on the most sensitive absorbance wavelengths, 795 and 732 nm for Nd, 520 and 377 nm for Er. FIG. 10A is a series of absorbance spectra of $Er^{3+}$-LanM after repeated acid attacks. FIG. 10B is a series of absorbance spectra of $Nd^{3+}$-LanM after repeated acid attacks. FIG. 10C is a graph of % Er bound to LanM calculated based on the most sensitive absorbance wavelengths. FIG. 10D is a graph of % Nd bound to LanM calculated based on the most sensitive absorbance wavelengths.

FIG. 11A is a series of absorbance spectra showing the thermal

Figure 11A:
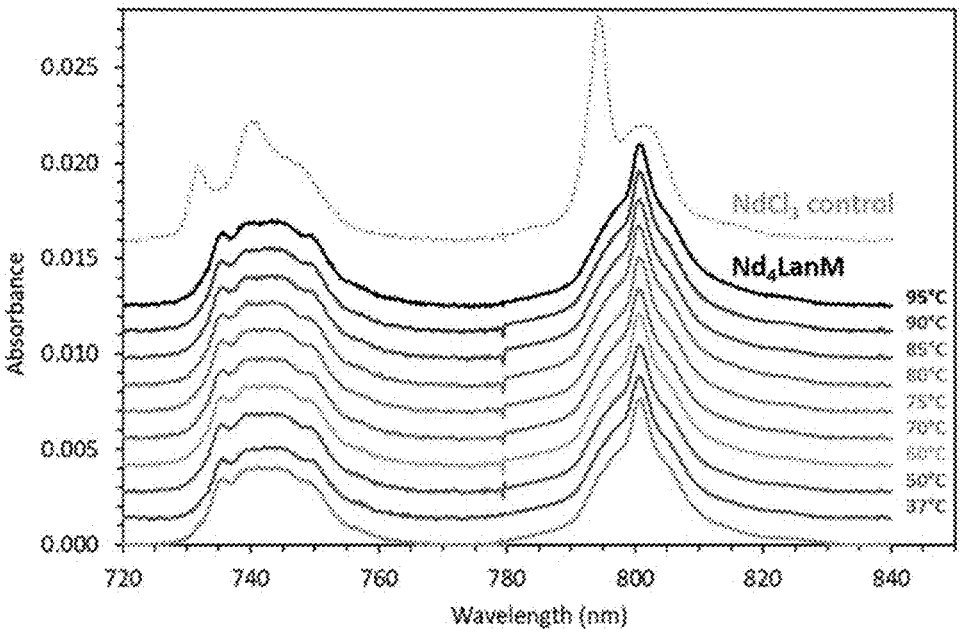
FIG. 11A-FIG. 11B shows the thermal stability of REE-LanM. Thermal stability tests of the $Nd^{3+}$-LanM complex followed by UV-vis-NIR spectrophotometry and dynamic light scattering. [Nd]=1 mM, [LanM]=0.25 mM. Dotted curve: 1 mM $NdCl_3$, no LanM. Buffer: 25 mM glycine, 25 mM $KCH_3COO$, 50 mM KCl, pH 5. The samples were successively incubated for 10 hours at each temperature from 25° C. to 95° C. (Total test>100 h) as indicated on the graphs. Absorbance spectra measured after cooling to room temperature. Hydrodynamic diameter of unbound LanM and Nd-bound LanM. [LanM]=100 μM. [Nd]=0 or 600 μM.
Figure 11B:
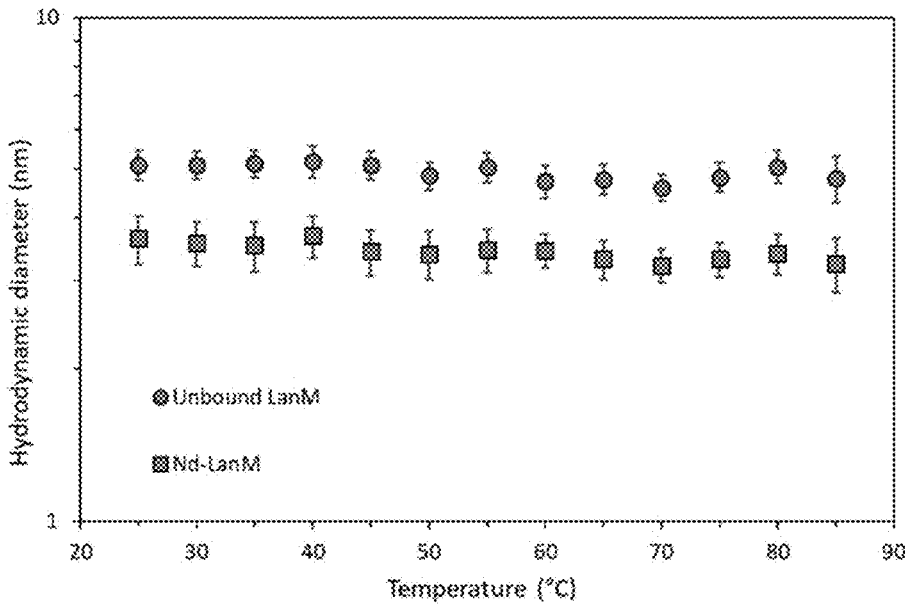

7 stability of the $Nd^{3+}$-LanM complex. FIG. 11B is a graph of the hydrodynamic diameter of unbound LanM and Nd-bound LanM at various temperatures.

Figure 12A:
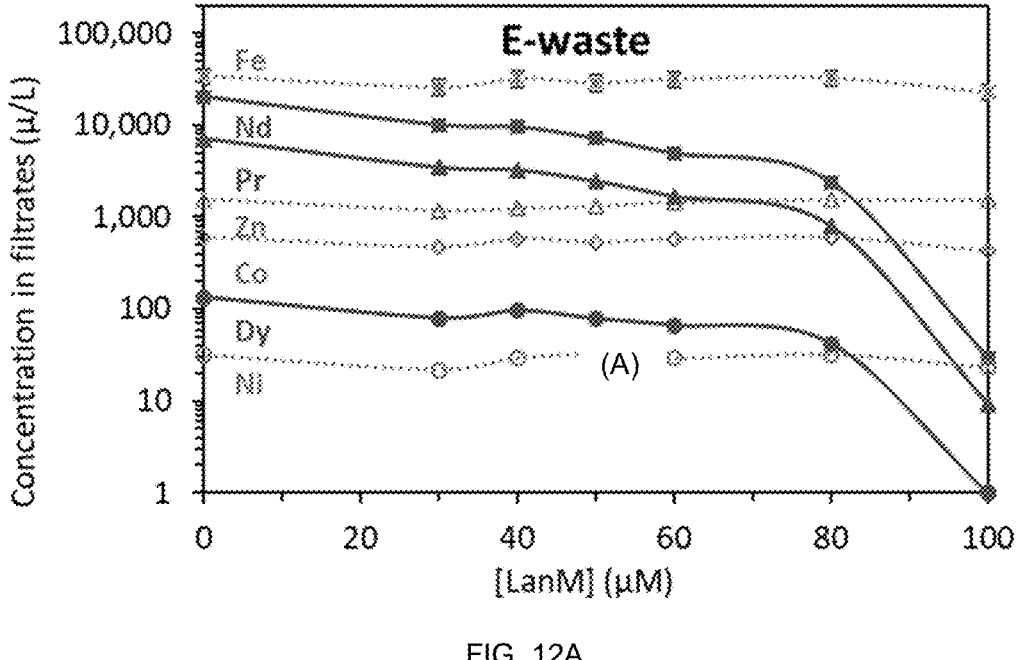
Figure 12B:
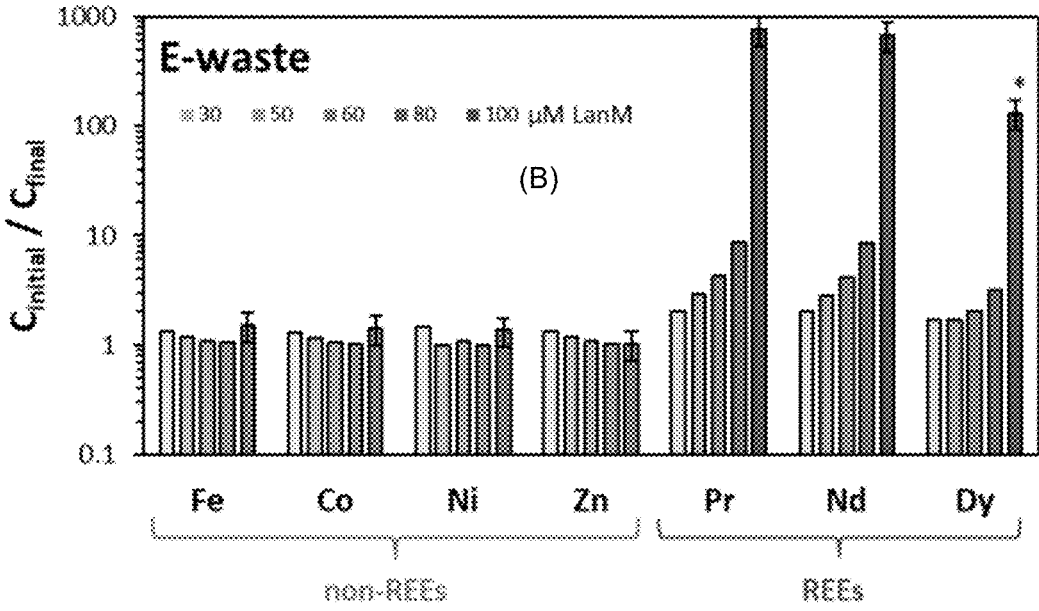

FIG. 12A-FIG. 12B shows the protein-based selective recovery of REEs from industrial feedstocks (E-waste). FIG. 12A is a graph of the concentrations of REEs and non-REE impurities in the low-molecular weight filtrates after addition of LanM to the electronic waste leachate, pH=3.9, [LanM]=0 to 100 M. FIG. 12B is a graph of the concentration ratios between the initial E-waste leachate solution and the filtrates.

Figures 13A, 13B:
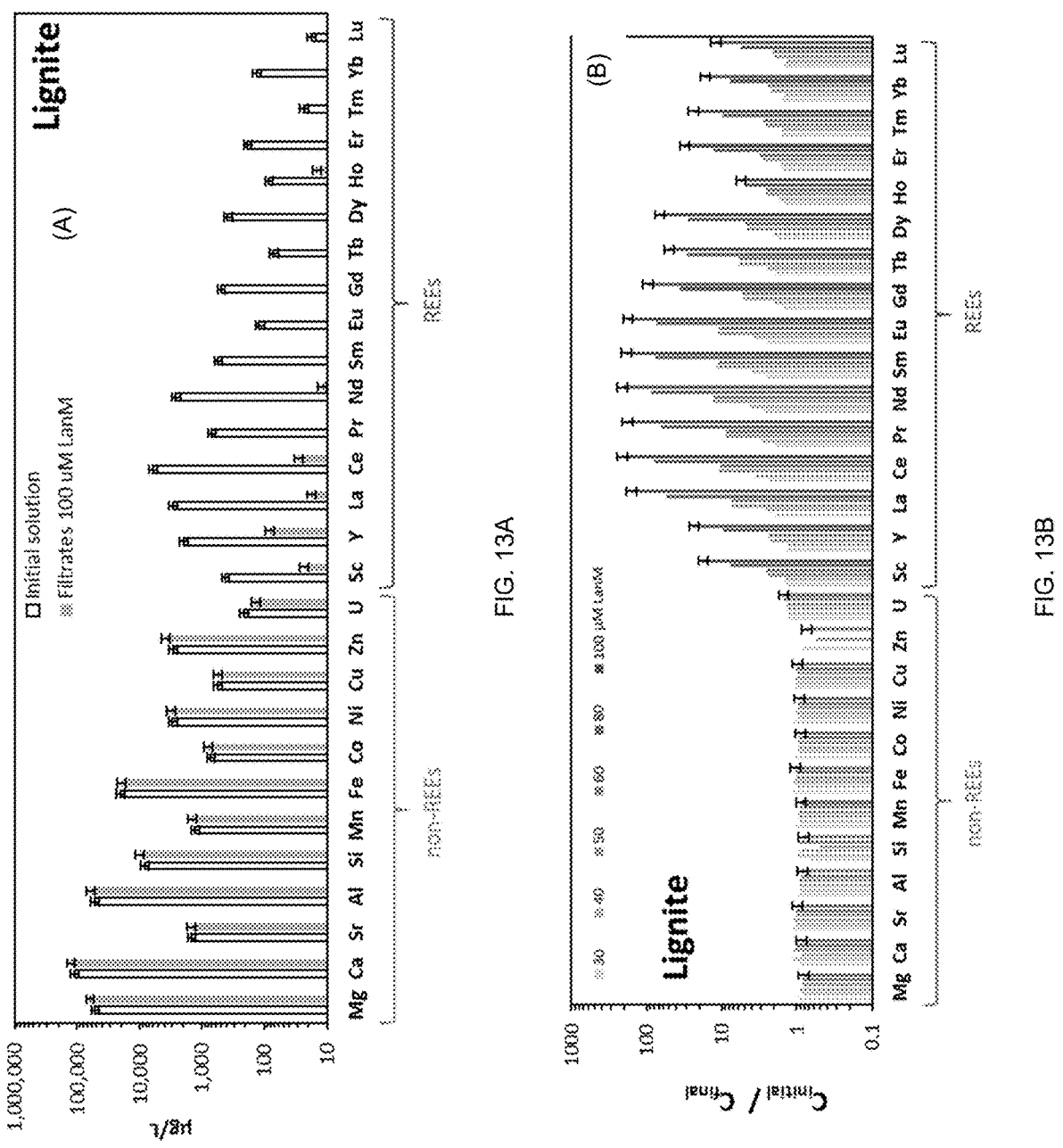

FIG. 13A-FIG. 13B shows the protein-based selective recovery of REEs from industrial feedstocks (lignite). FIG. 13A is a graph of the compositions of the initial lignite feedstock and the low-molecular weight filtrates. [LanM] =100 µM. pH=3.6. FIG. 13B is a graph of the concentration ratios between the initial lignite leachate solution and the filtrates.

Figure 14:
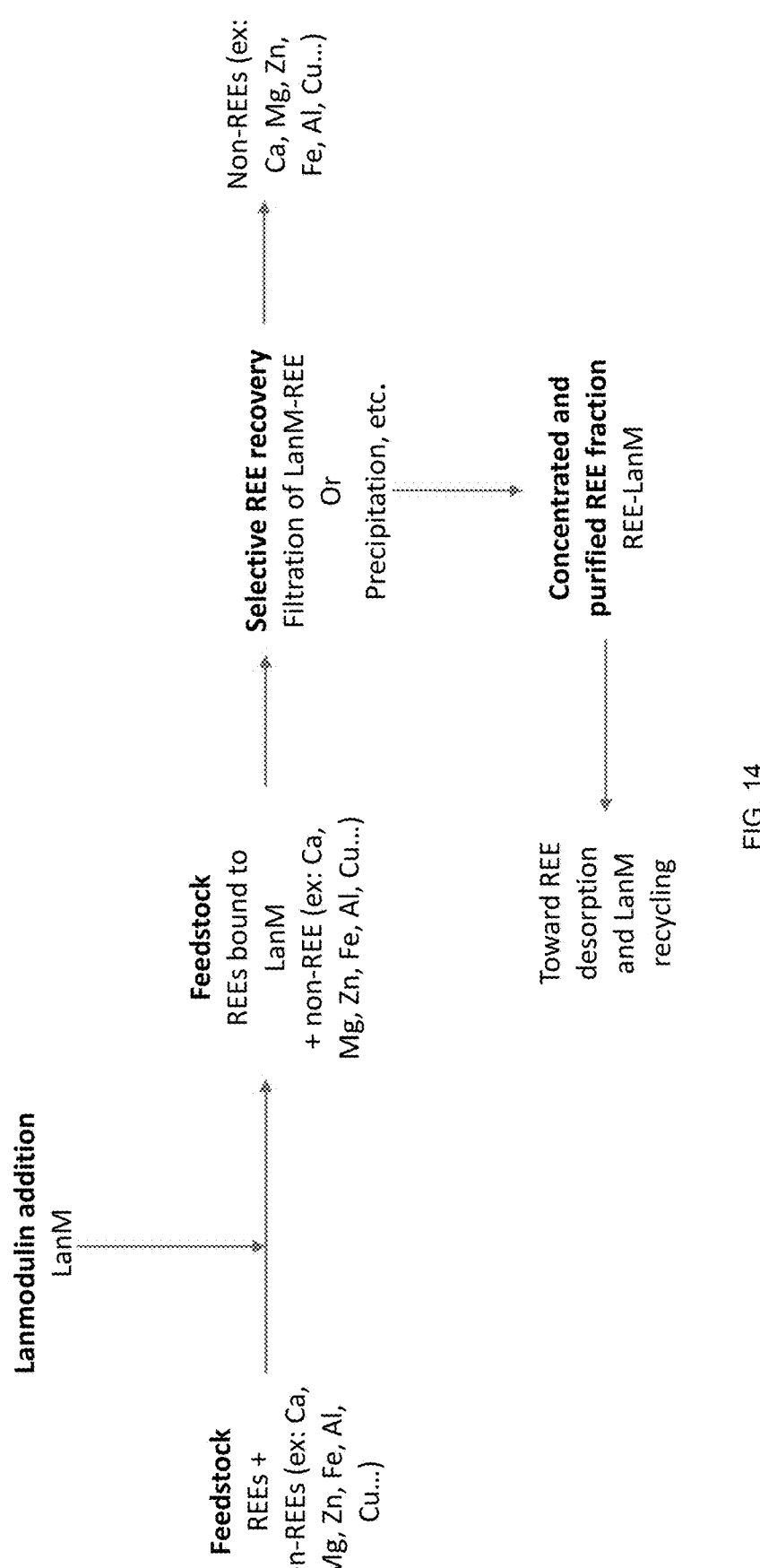

FIG. 14 shows an example process flow for the sequestration or purification of a feedstock comprising REEs and non-REEs with LanM as disclosed herein.

Figure 15:
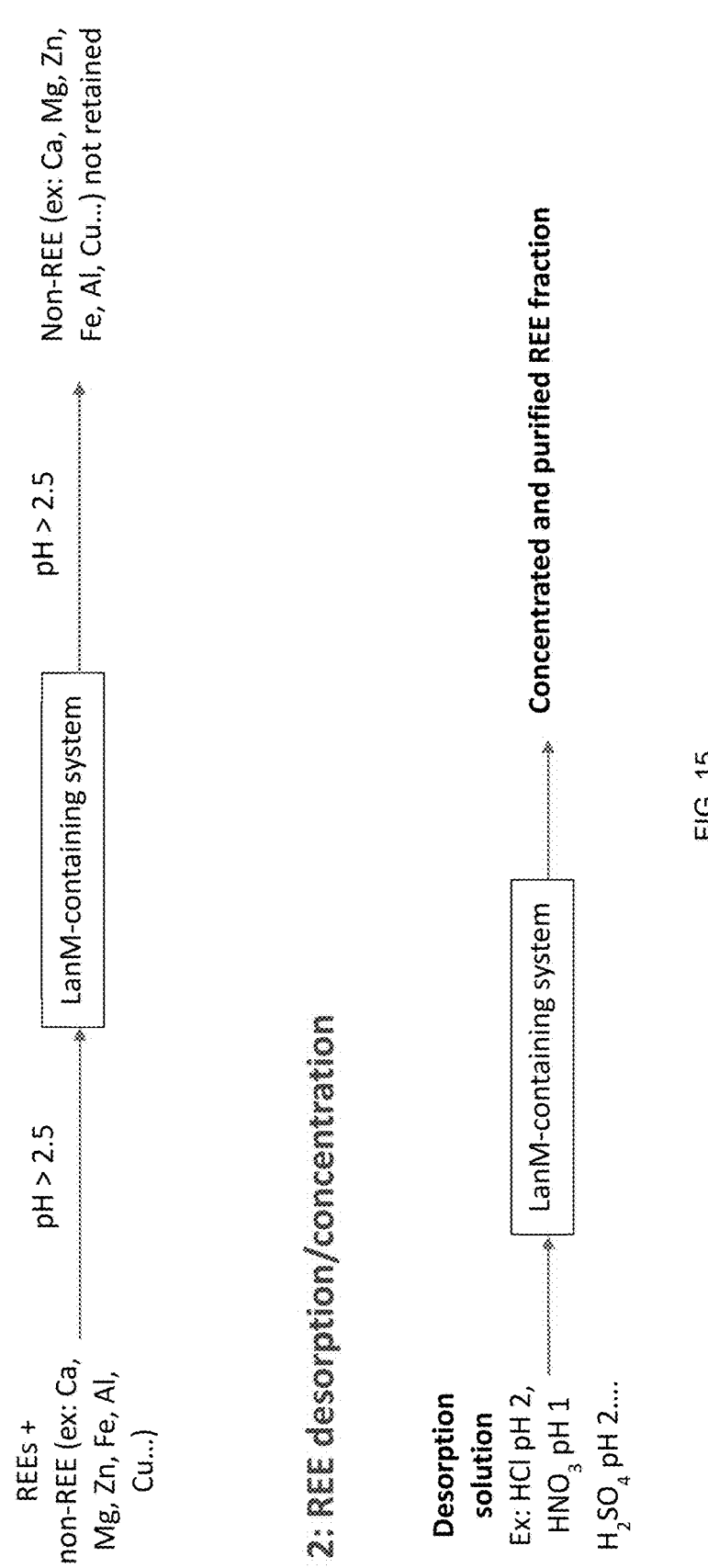

FIG. 15 shows an example of a pH controlled process flow for the sequestration or purification of a feedstock comprising REEs and non-REEs with LanM as disclosed herein.

Figure 16:
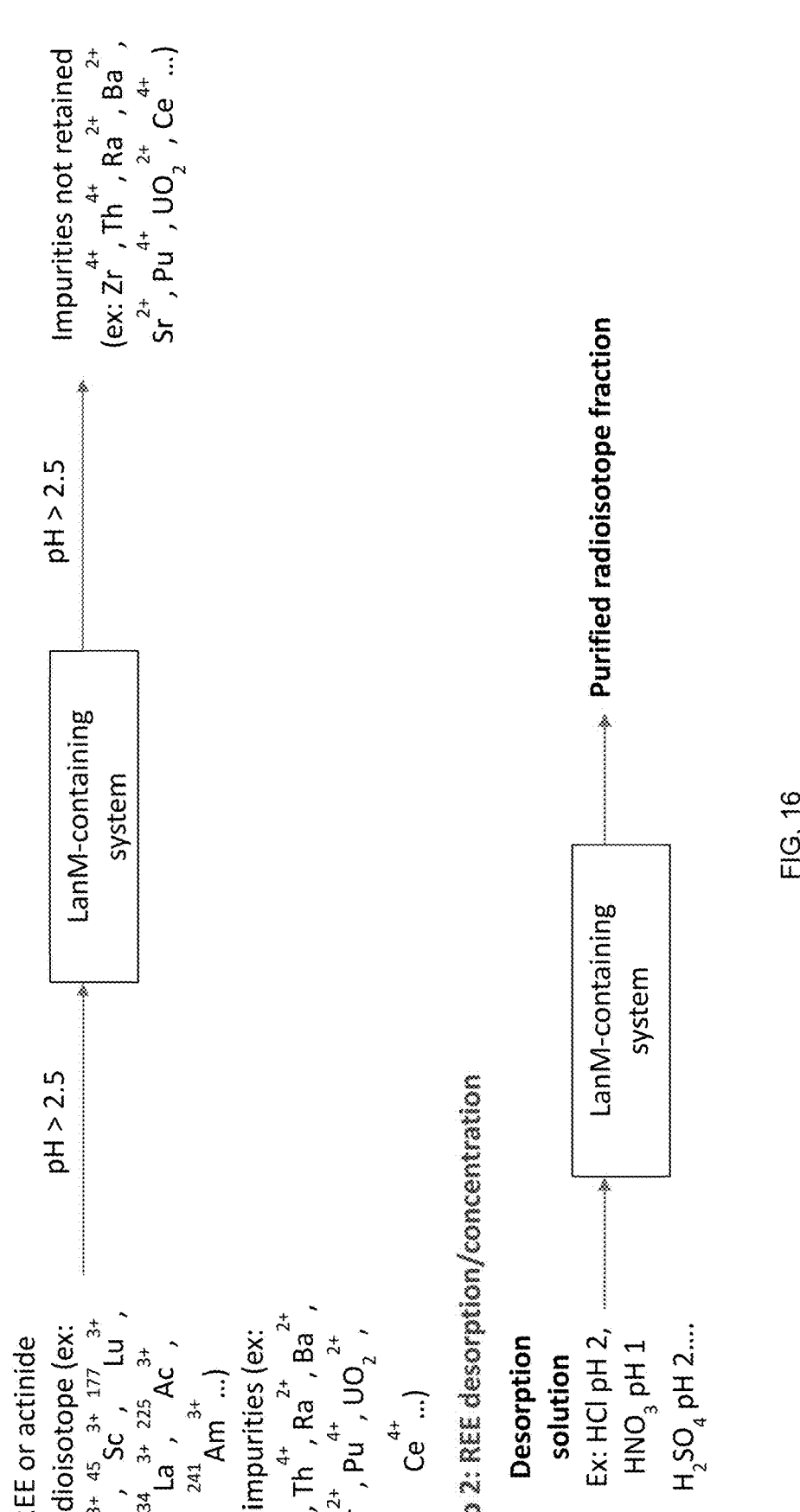

FIG. 16 shows an example of a pH controlled process flow for the sequestration or purification of a feedstock comprising radioactive isotopes and impurities.

Figure 17A:
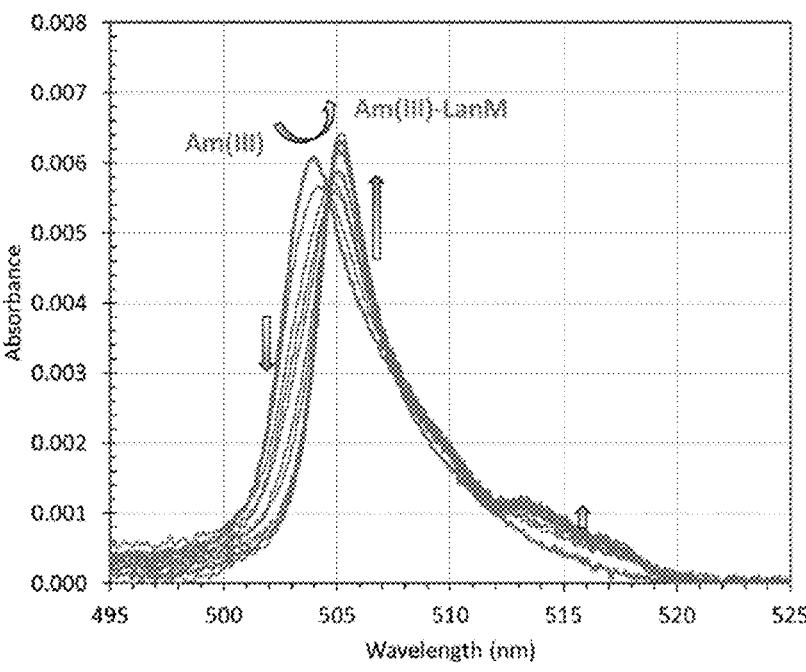

FIG. 17A is an absorbance spectra of free Am(III) and bound Am(III) (Am(III)-LanM) as disclosed herein.

Figure 17B:
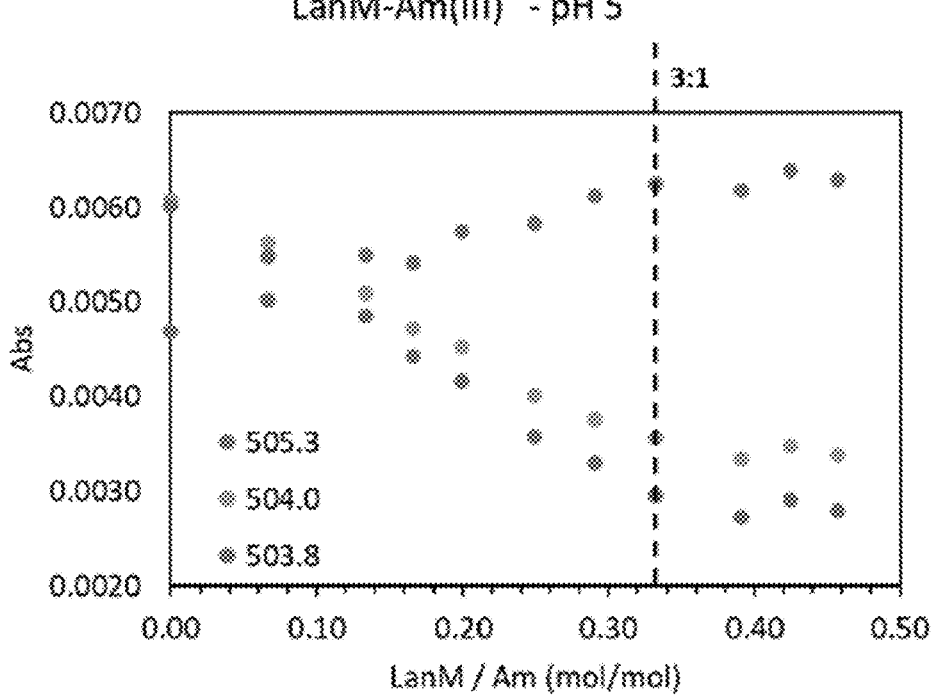

FIG. 17B is a graph of absorbance versus the molar ratio of LanM and Am at pH of 5.

Figure 18A:
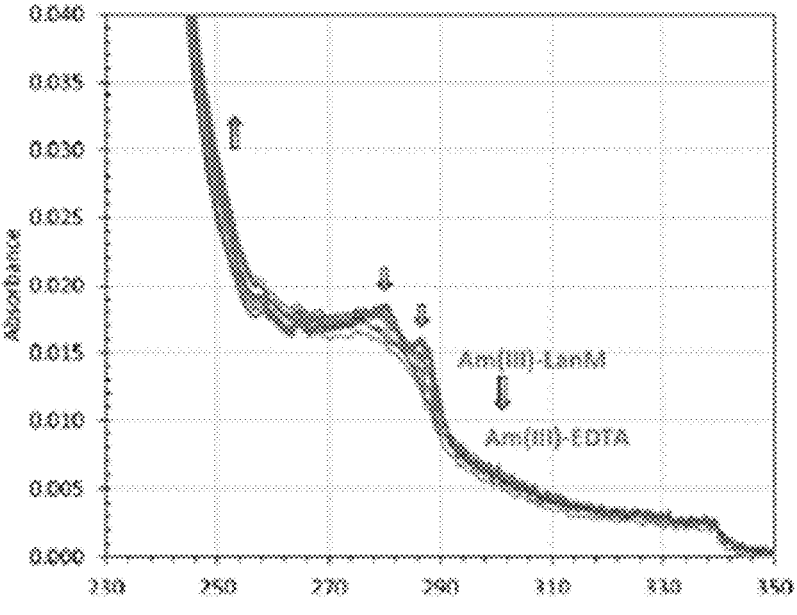
Figure 18B:
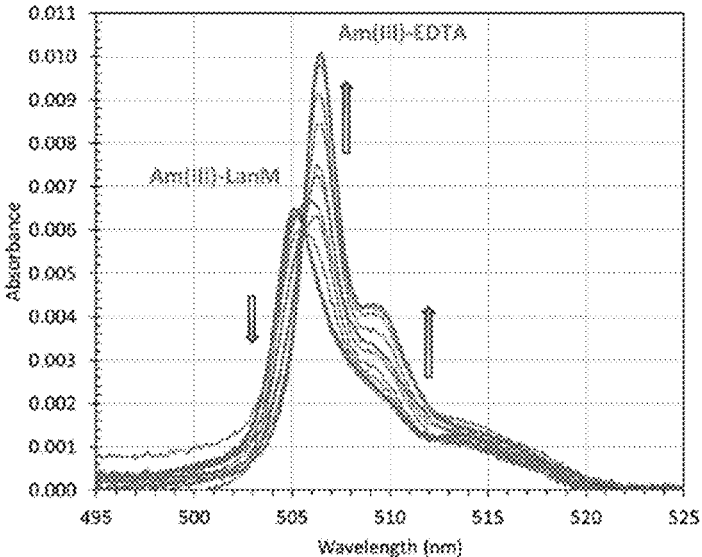
Figure 18C:
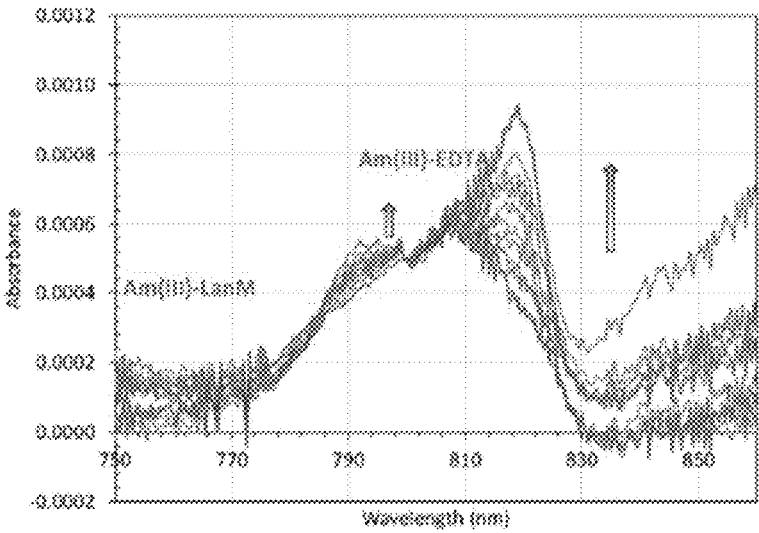
Figure 18D:
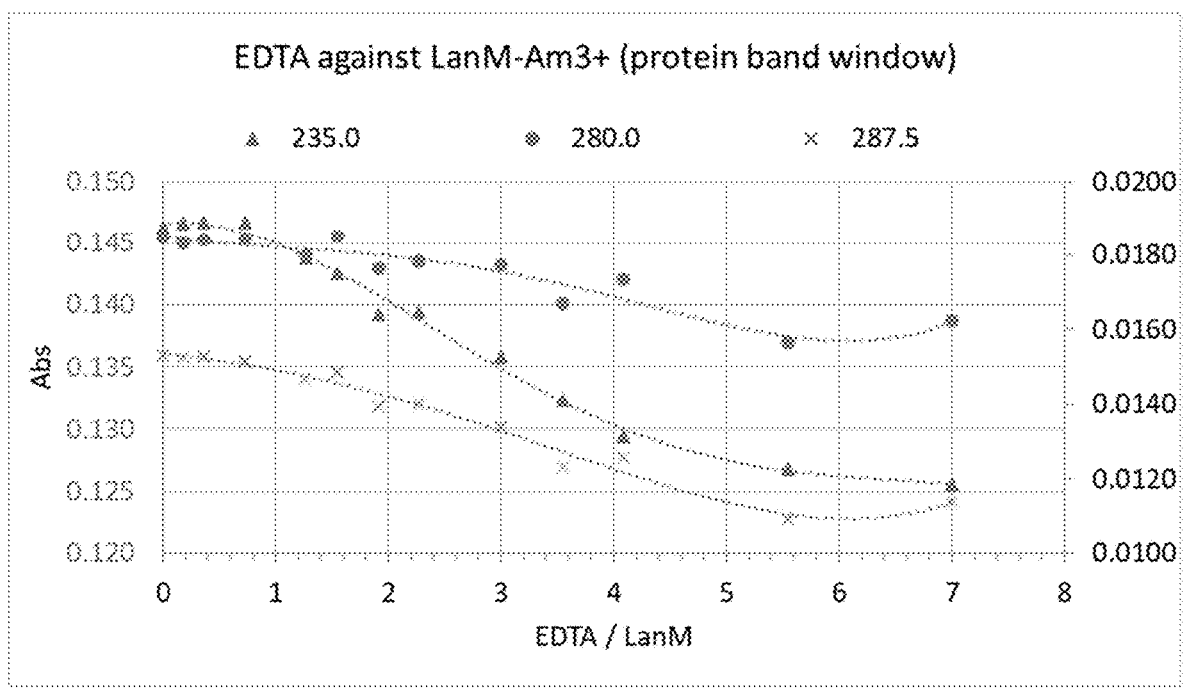
Figure 18E:
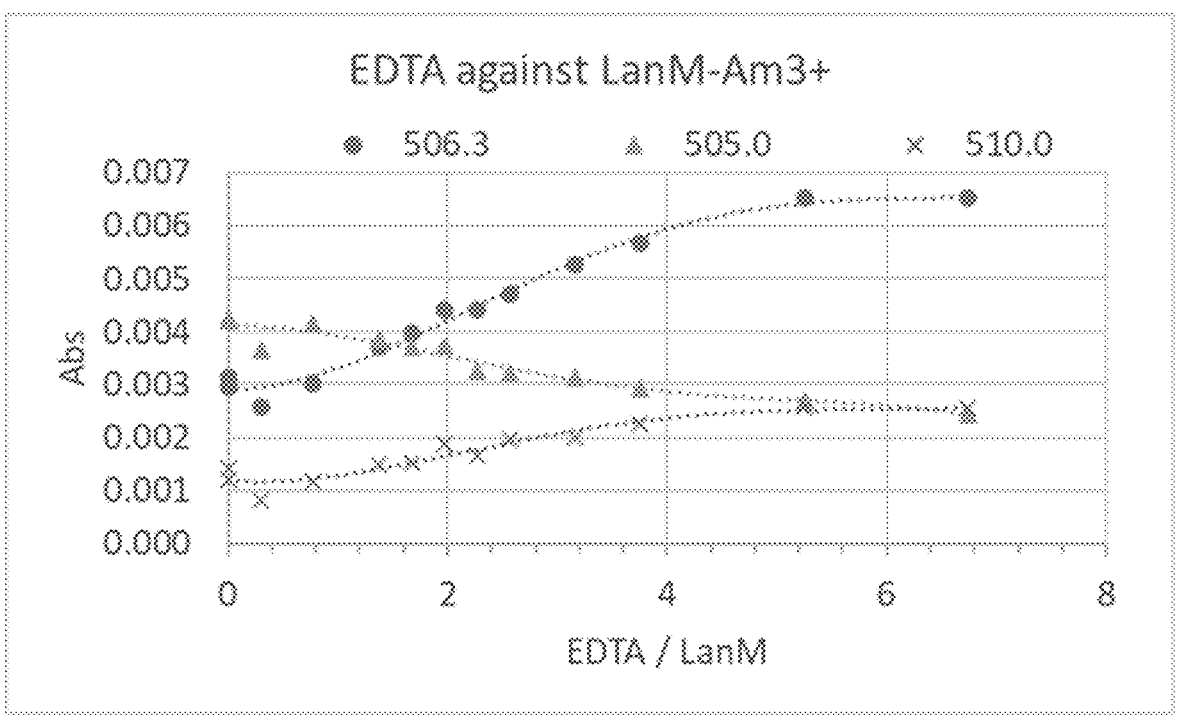
Figure 18F:
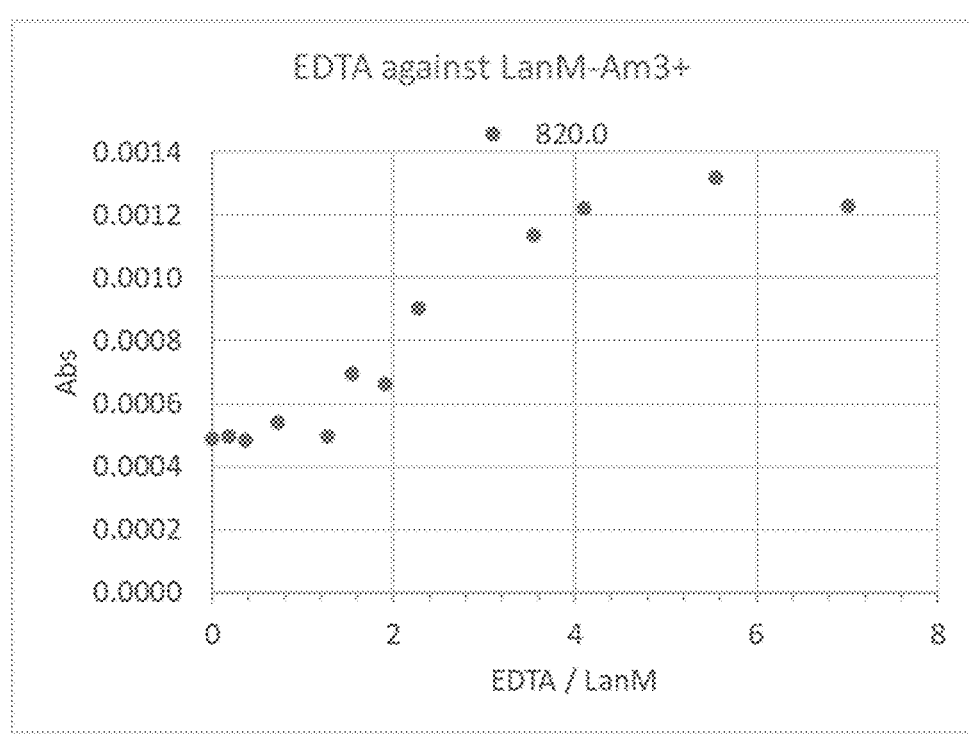

FIG. 18A-FIG. 18F is an example of a competition titration between LanM and EDTA for the binding to $Am^{3+}$. FIG. 18A shows a series of absorbance spectra of a competition titration between LanM and EDTA for the binding of Am(III). The absorbance band at ~270 nm is specific to the protein and corresponds to the bound LanM (Am(III)-LanM) and unbound LanM. FIG. 18B shows an absorbance spectrum of a competition titration between LanM and EDTA for the binding of Am(III). The absorbance band at ~505 nm is specific to Am(III) corresponds to the Am(III)-LanM and Am(III)-EDTA complexes. FIG. 18C shows an absorbance spectrum of a competition titration between LanM and EDTA for the binding of Am(III). The absorbance band at ~800 nm is specific to Am(III) corresponds to the Am(III)-LanM and Am(III)-EDTA complexes. FIG. 18D is a graph of the absorbance versus the molar ratio of EDTA/ LanM at various wavelengths of said competition titration. FIG. 18E is a graph of the absorbance versus the molar ratio of EDTA/LanM at various wavelengths (i.e., 235 nm, 280 nm, and 250 nm) of said competition titration. FIG. 18F is a graph of the absorbance versus the molar ratio of EDTA/ LanM at low absorbance of said competition titration.

Figure 19A:
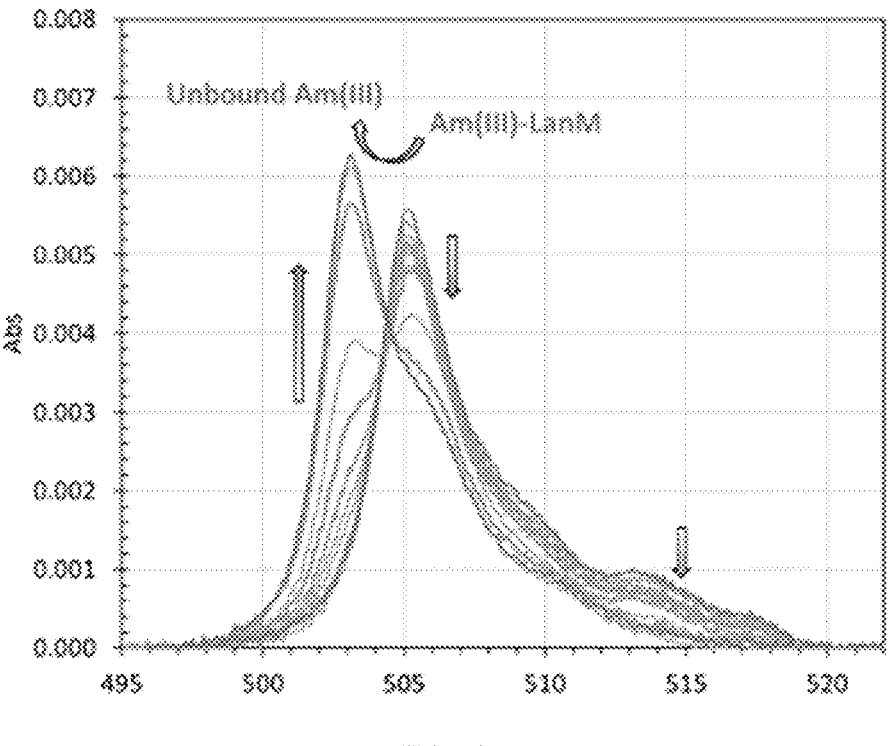

FIG. 19A is an absorbance spectrum of Am(III)-LanM and unbound Am(III) at low pH measured during a pH titration of Am(III)-LanM. The variations in the spectrum indicate that Am(III) is released from LanM as the pH decreases.

Figure 19B:
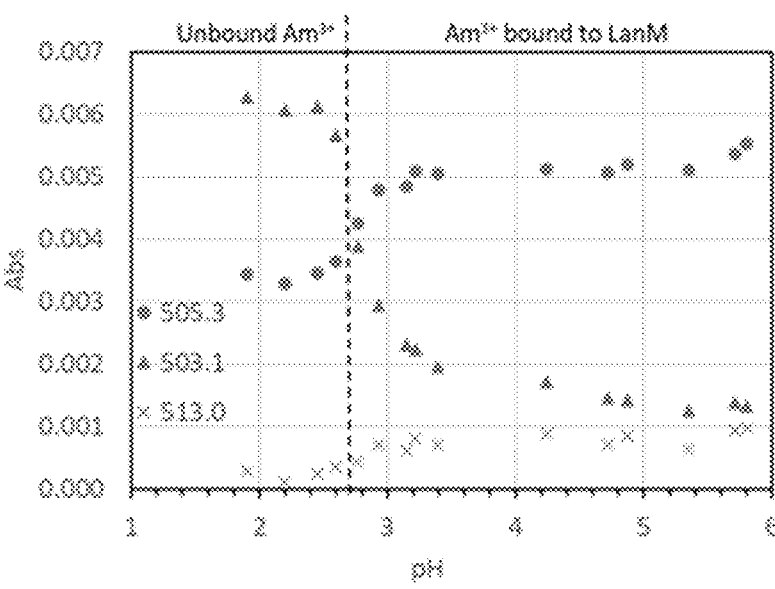

FIG. 19B is a graph of the absorbance of Am(III)-LanM and unbound Am(III) versus pH.

Figure 19C:
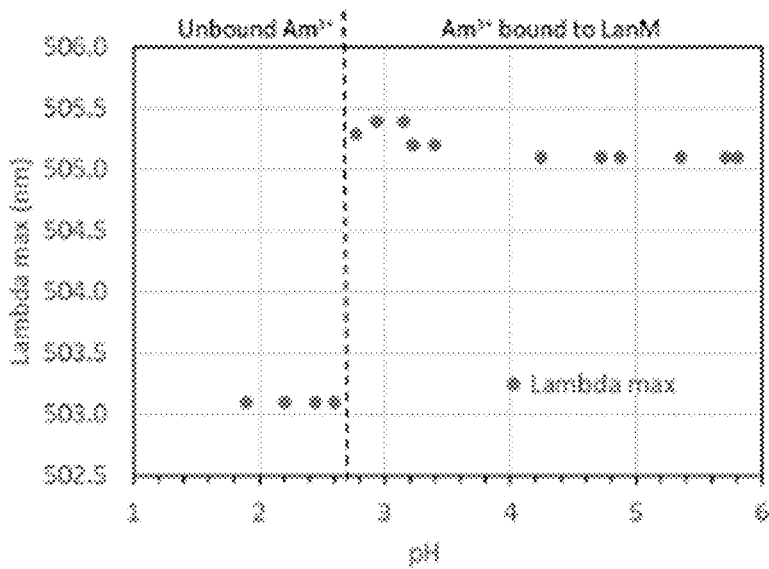

FIG. 19C is a graph of the lambda max (nm) of Am(III)-LanM and unbound Am(III) versus pH.

Figure 20:
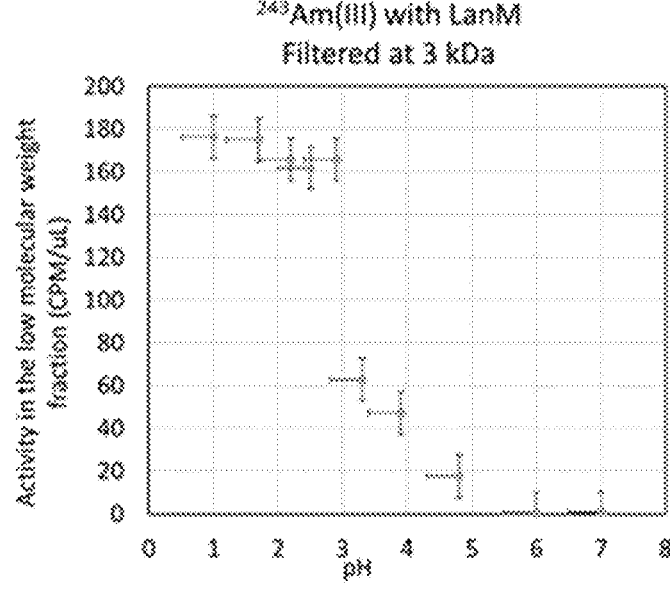

FIG. 20 is a graph of the activity in the low molecular weight fraction (CPM/µL) of a filtered solution of Am(III) with LanM at various pHs. The filter had a molecular weight cutoff of 3 kDa.

8

Figure 21:
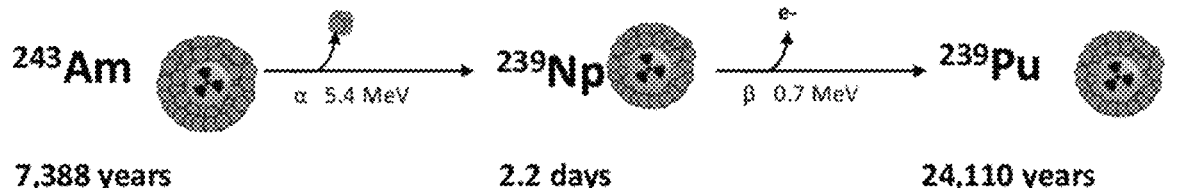

FIG. 21 is a depiction of the radioactivity of radiometal 243Am, its half-life and decay products.

Figure 22:
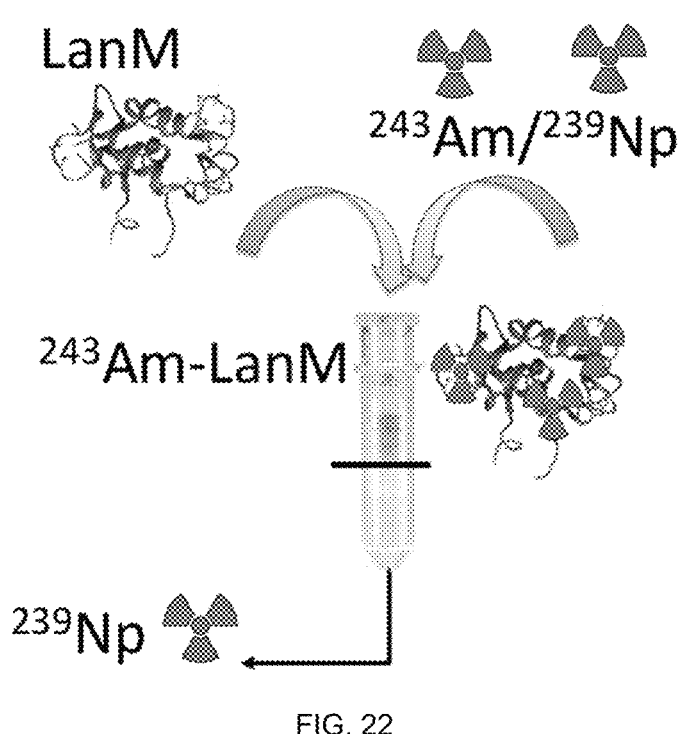

FIG. 22 is a schematic showing a method of purifying two radiometals (Am-243 and Np-239) using a spin filter as disclosed herein.

Figure 23:
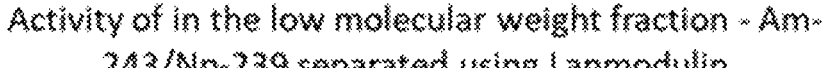
Figure 23:
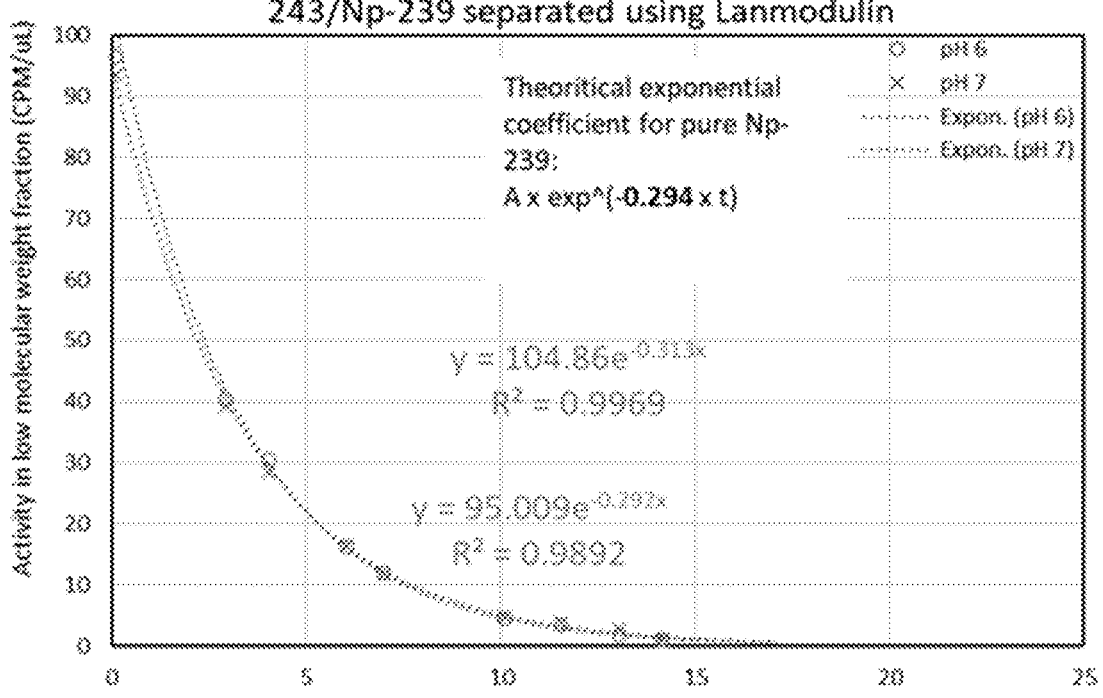

FIG. 23 is a graph of the radioactivity detected in the low molecular weight fractions versus time of a mixture of Am-243 and Np-239 separated by adding LanM at pH 6 and pH 7. The decay profile indicates that the low molecular weight fractions contain pure Np-239.

Figure 24:
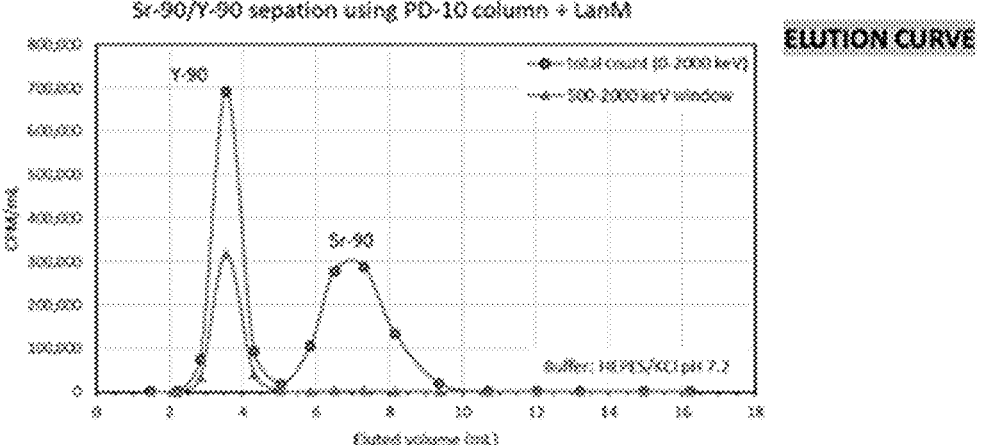

FIG. 24 is a graph of the elution curve of a Sr-90/Y-90 separation as disclosed herein using a PD-10 column with LanM.

Figure 25:
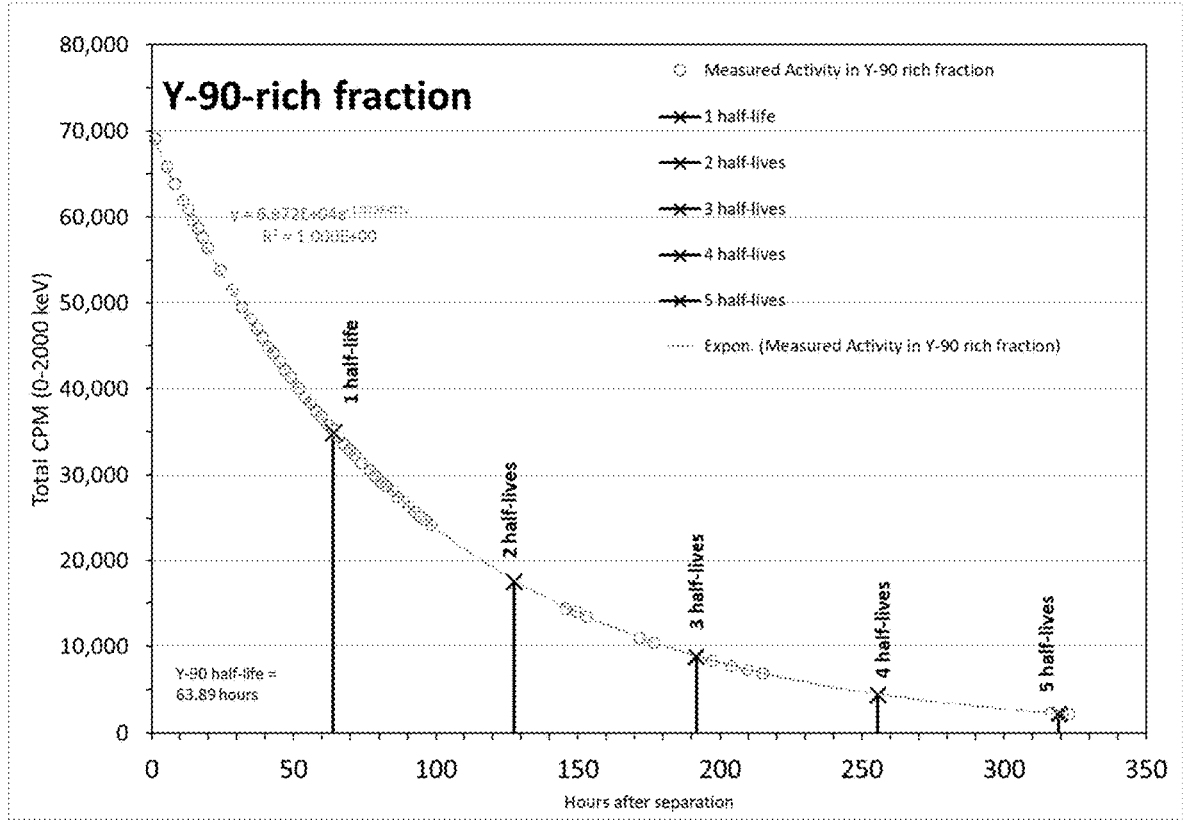

FIG. 25 is a graph of the decay profile over time of the Y-90 column elution fraction. The decay profile indicates that the LanM fraction contains pure Y-90.

Figure 26:
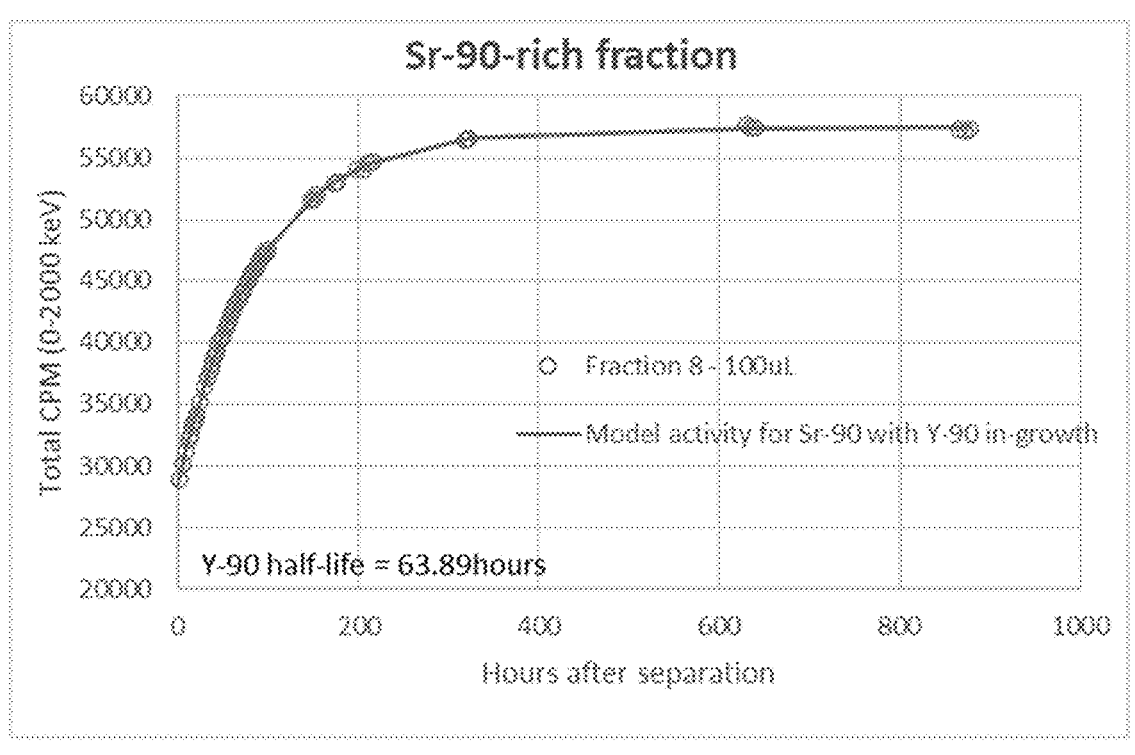

FIG. 26 is a graph of the radioactivity profile over time of the Sr-90 (and its natural regeneration of Y-90 due to secular equilibrium) column elution fraction. The decay profile over time indicates that the low molecular weight fractions contain pure Sr-90 just after separation using LanM.

Figure 27:
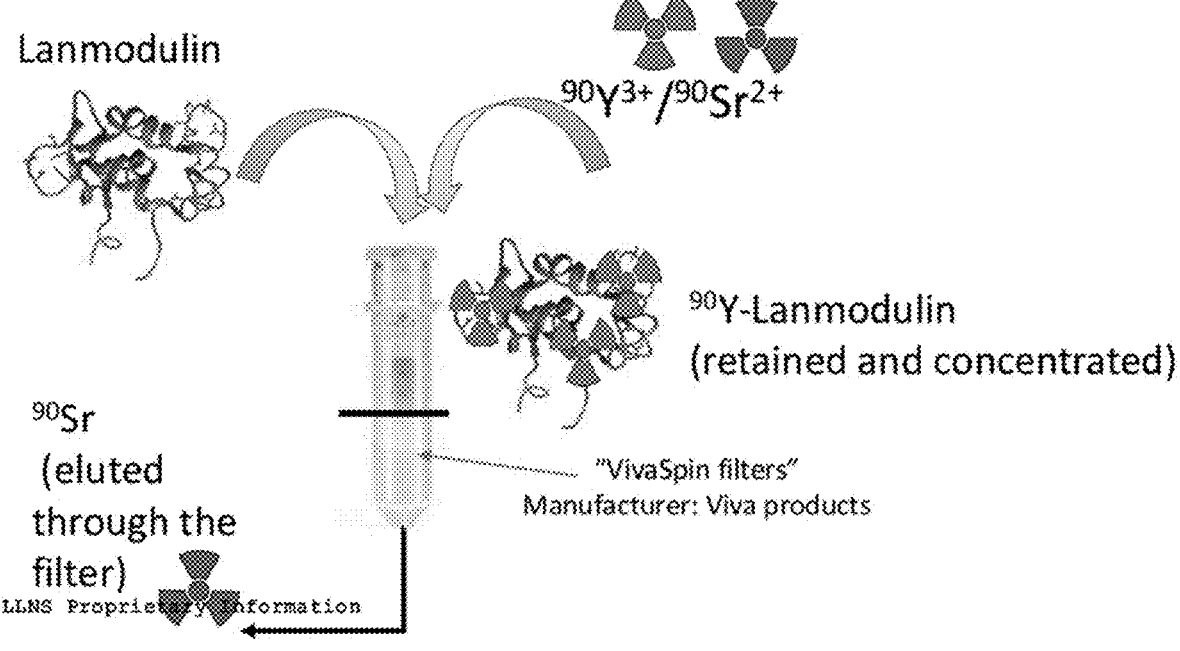

FIG. 27 is a schematic showing a method of purifying a radioactive rare-earth element (Y-90) and its radioactive daughter (Sr-90) using a spin filter as disclosed herein.

Figure 28:
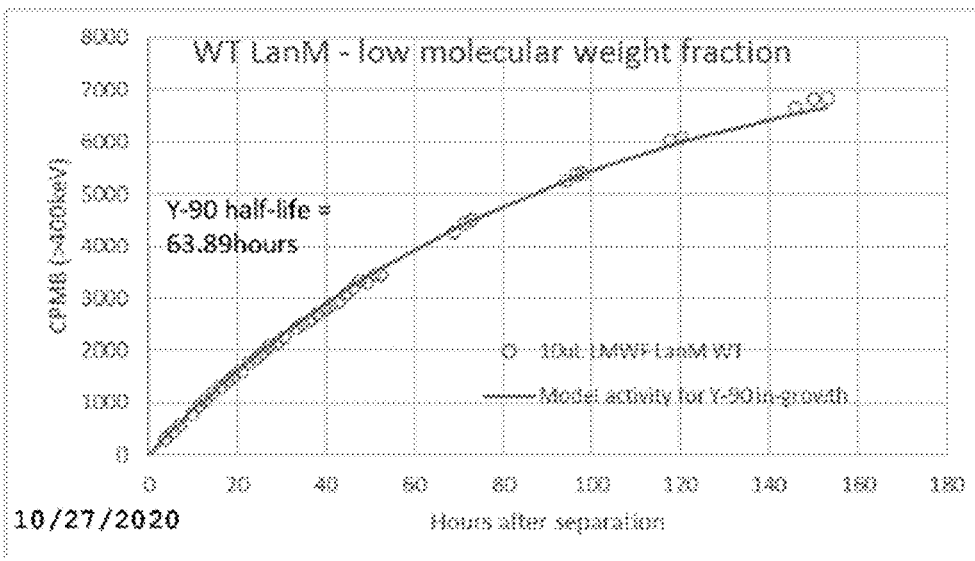

FIG. 28 is a graph of the radioactivity profile of the low molecular weight fraction obtained by spin filtration of a Sr-90/Y-90 solution initially at secular equilibrium. The decay profile over time indicates that the low molecular weight fraction contains pure Sr-90 just after separation using LanM.

Figure 29:
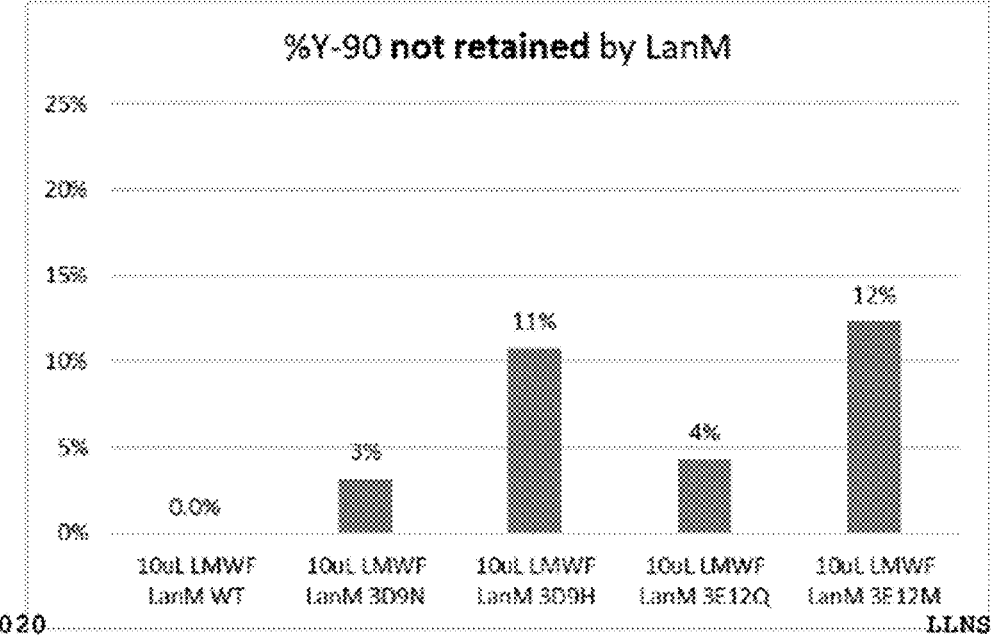

FIG. 29 is a graph of the % Y-90 not retained by LanM and its various mutants disclosed herein in the spin filter.

Figure 30:
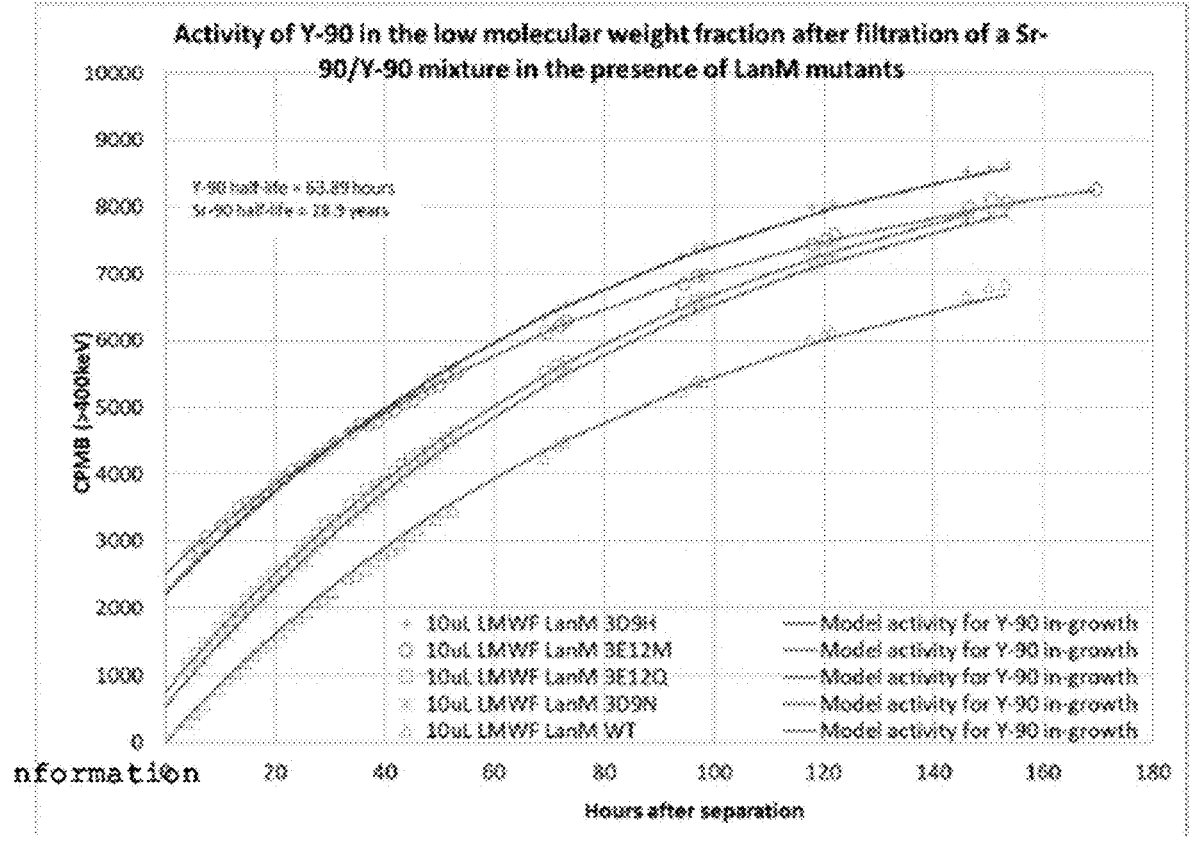

FIG. 30 is a graph of the activity of Y-90 from the low molecular weight fraction after filtration of a Sr-90/Y-90 mixture of metals in the presence of LanM mutants as disclosed herein.

Figure 31:
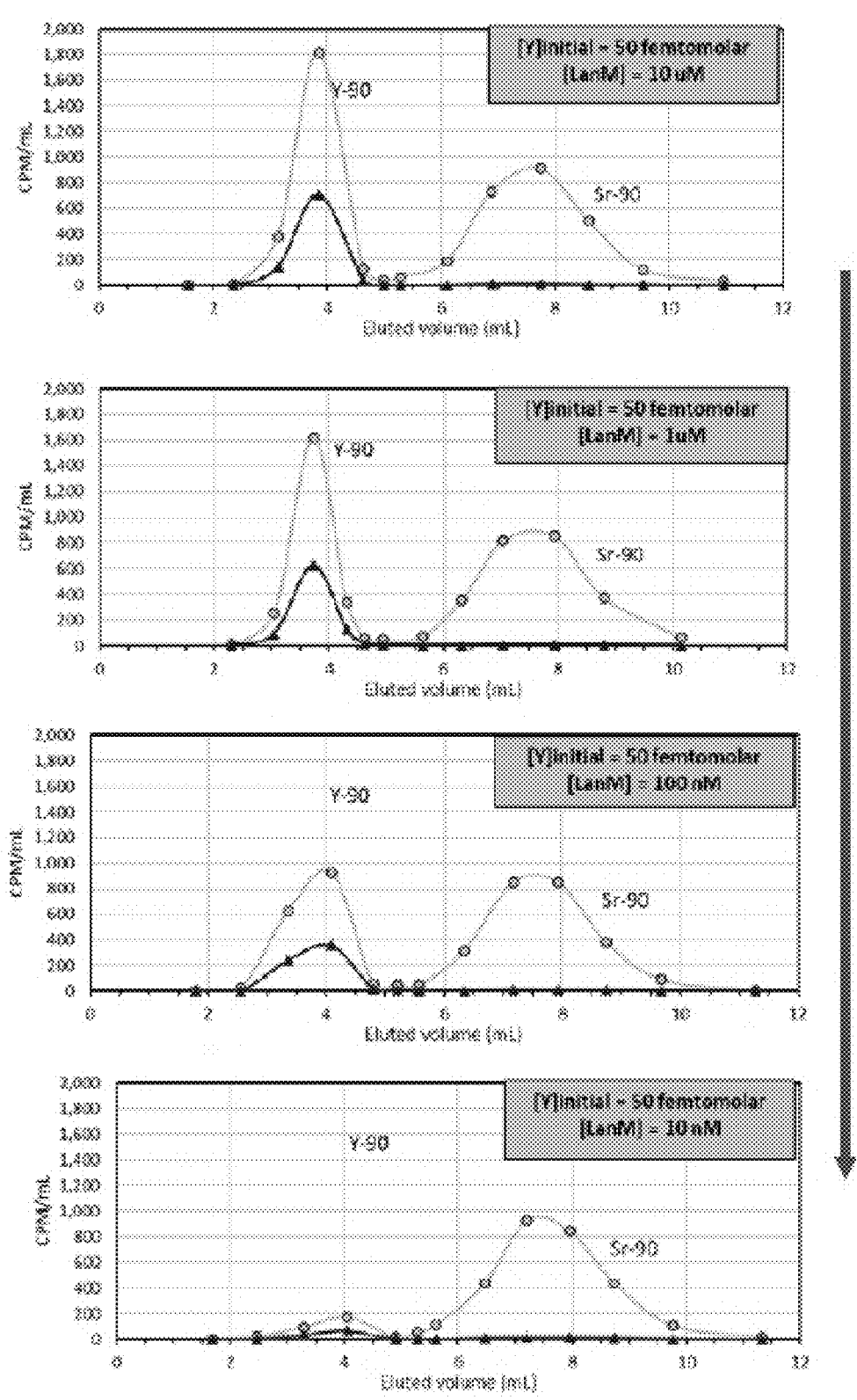

FIG. 31 shows multiple graphs of the elution curves of a Sr-90/Y-90 separation as disclosed herein with varying concentration of LanM using a PD-10 column.

Figure 32:
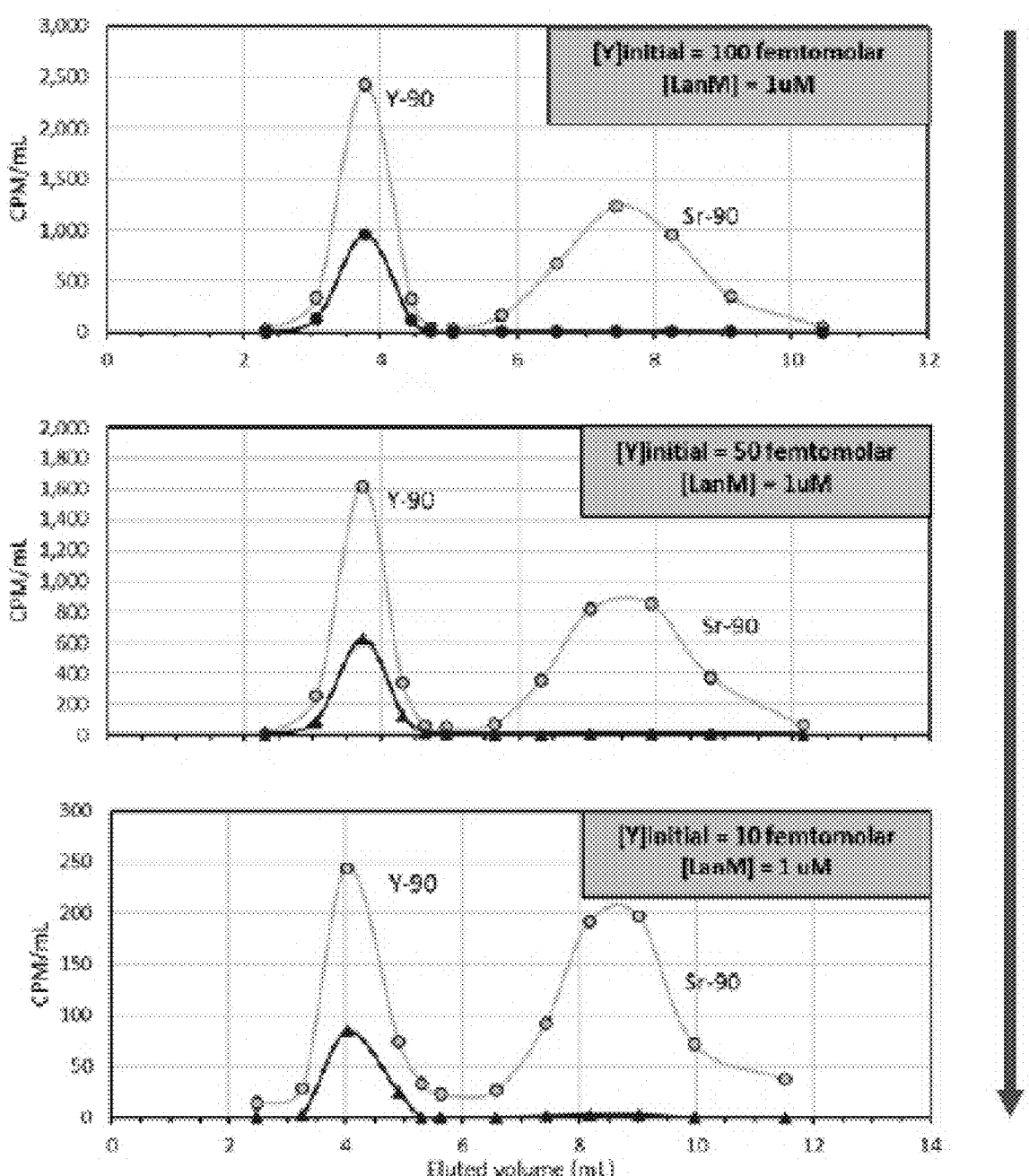

FIG. 32 shows multiple graphs of the elution curves of a Sr-90/Y-90 separation as disclosed herein with varying concentration of Y-90 using a PD-10 column.

Figure 33:
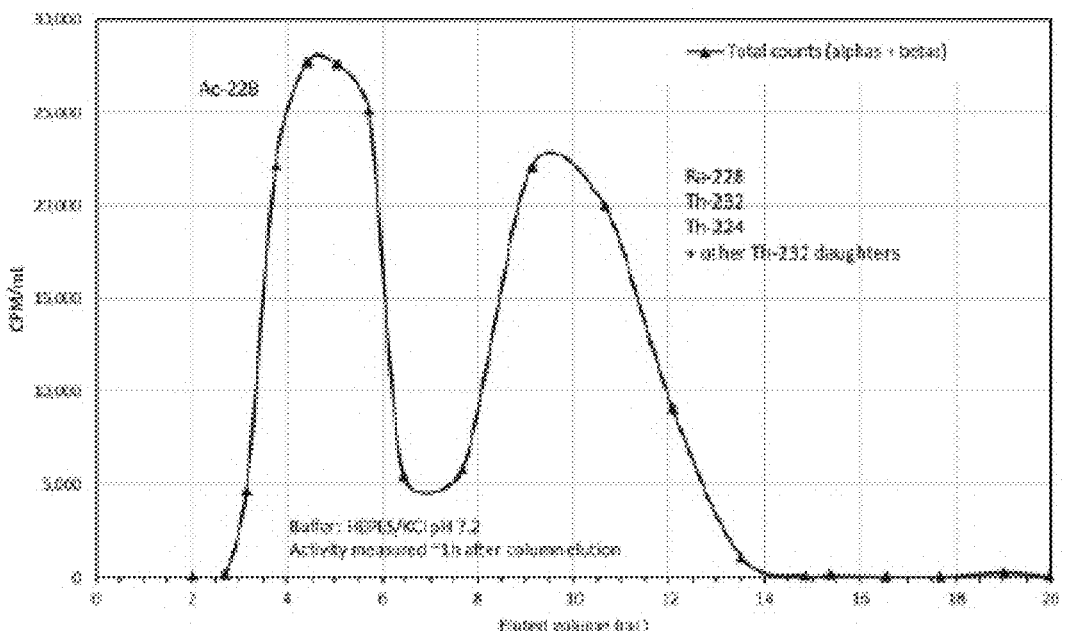

FIG. 33 is a graph of the elution curve of an Ac-228/Ra-228/Th-232/Th-228 separation as disclosed herein using a PD-10 column with LanM.

Figure 34:
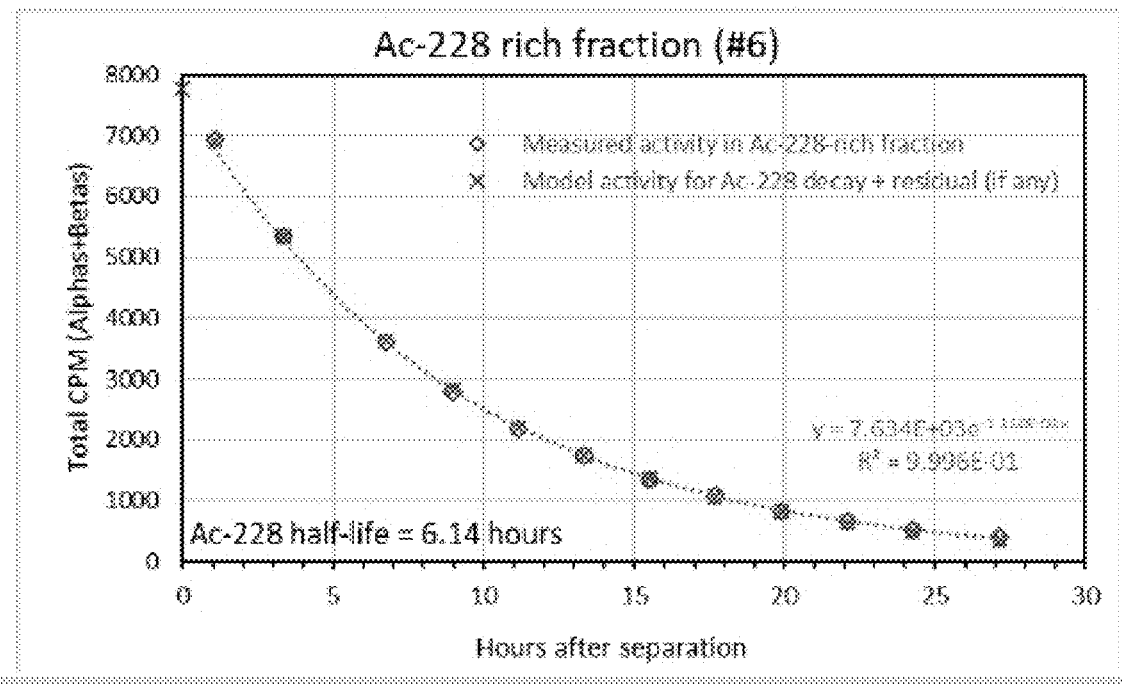

FIG. 34 is a graph of the decay profile over time of the Ac-228 column elution fraction. The decay profile indicates that the LanM fraction contains pure Ac-228.

Figure 35:
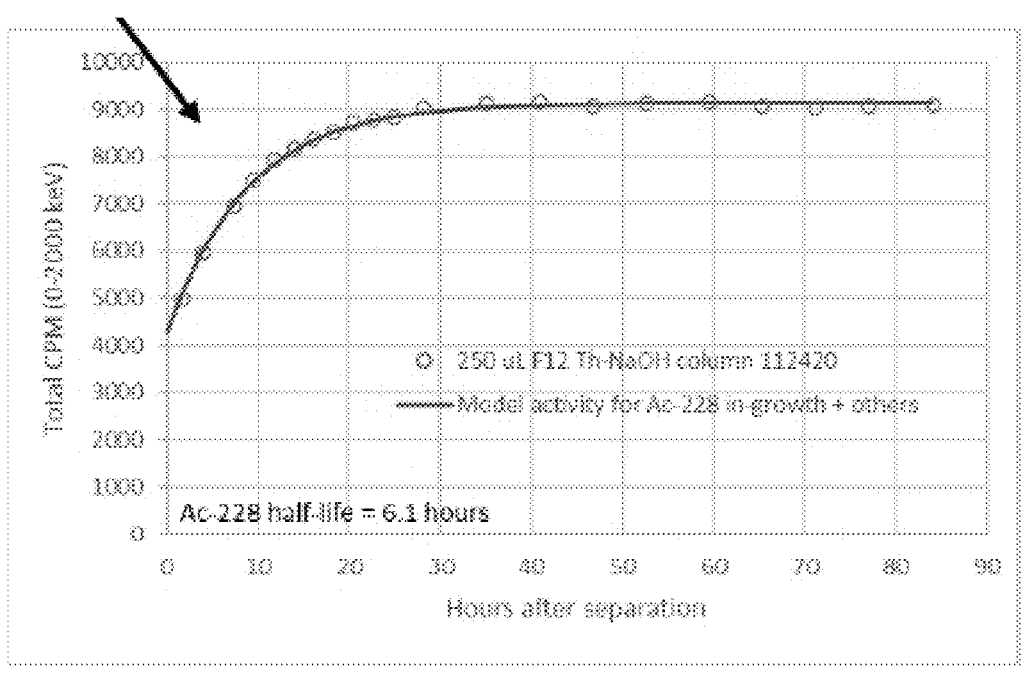

FIG. 35 is a graph of the radioactivity profile of the low molecular weight fraction obtained by spin filtration of an Ac-228/Ra-228/Th-232/Th-228 solution. The radioactivity profile over time indicates that the low molecular weight fraction contains the metals other than Ac-228 just after separation using LanM.

Figure 36:
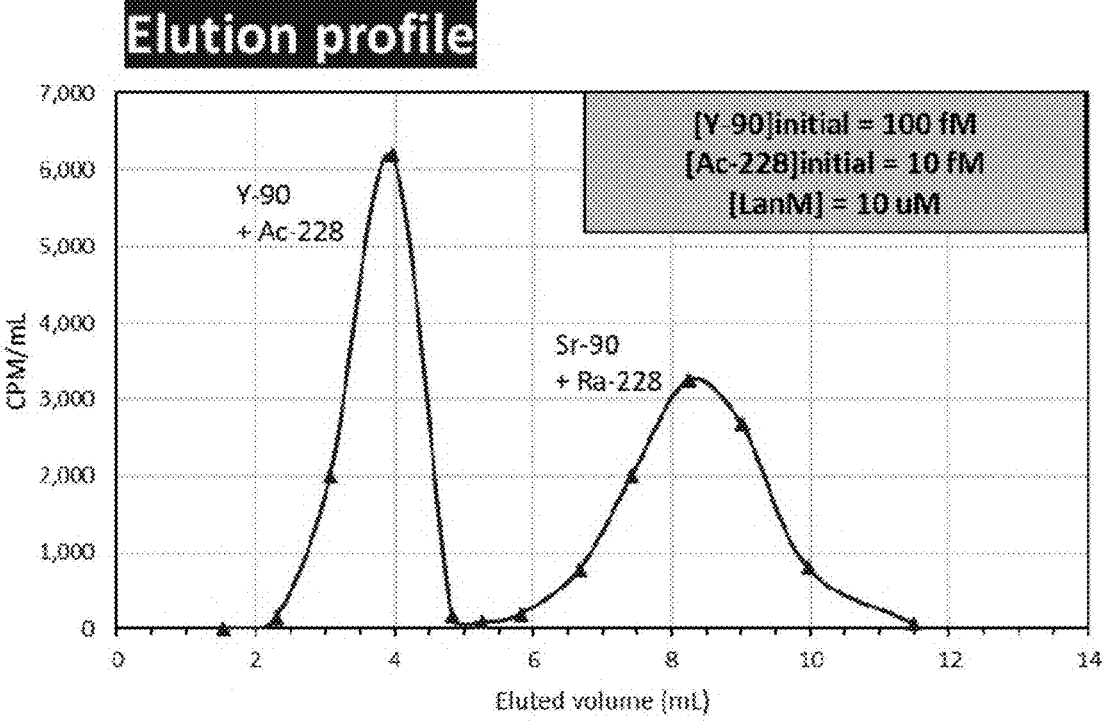

FIG. 36 is a graph of the elution curve of a Sr-90/Y-90/ Ac-228/Ra-228 separation as disclosed herein with LanM using a PD-10 column.

Figure 37:
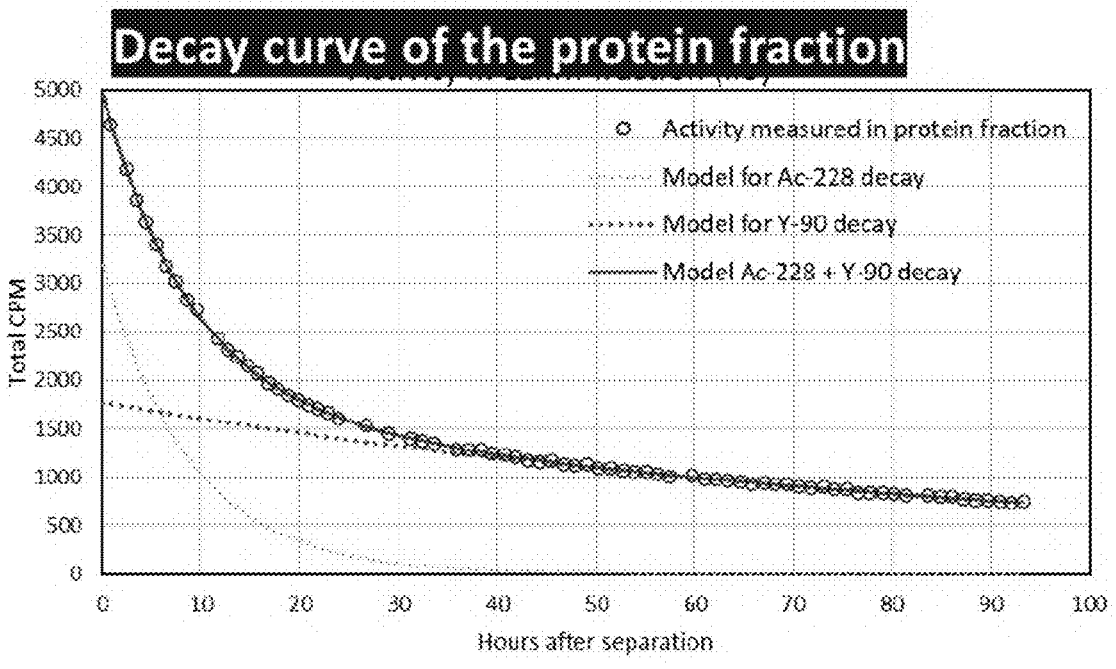

FIG. 37 is a graph of the decay profile over time of the Ac-228/Y-90 column elution fraction. The decay profile indicates that the LanM fraction contains only Ac-228/Y-90.

Figure 38:
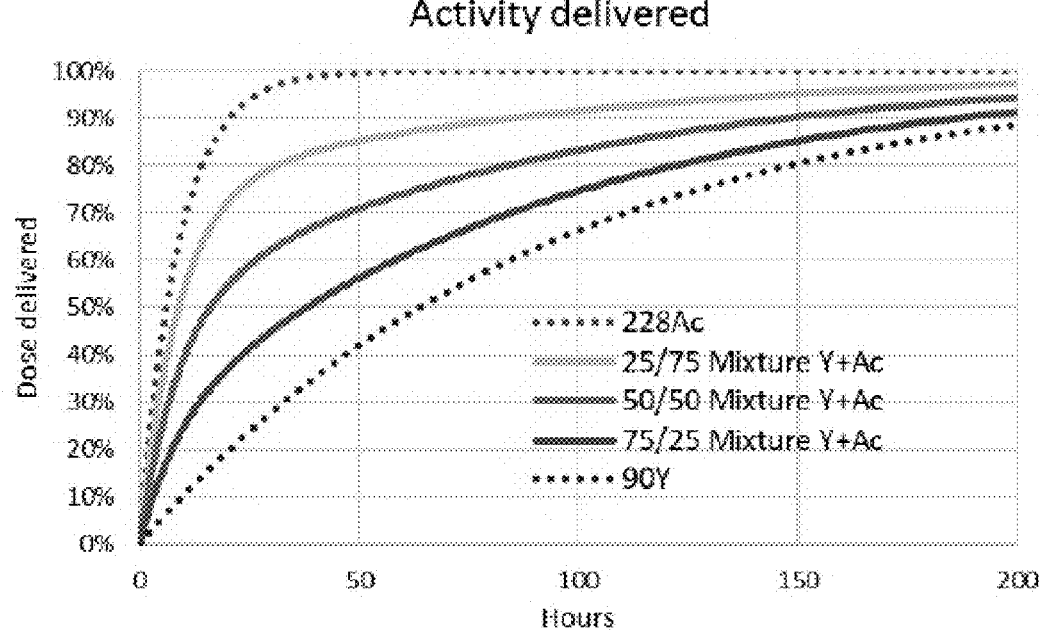

FIG. 38 is a graph of activity profile (in % of delivered dose) for a material initially containing a mixture of Ac-228 and Y-90. These calculated profiles show that the delivered dose profile (total dose, duration of the dose, and energy spectrum) can be modulated by varying the initial ratio between the two radioisotopes, such as what can be accomplished with using the methods disclosed herein with LanM, as it can bind two or more different radioisotopes simultaneously (see FIG. 37).

Figure 39:
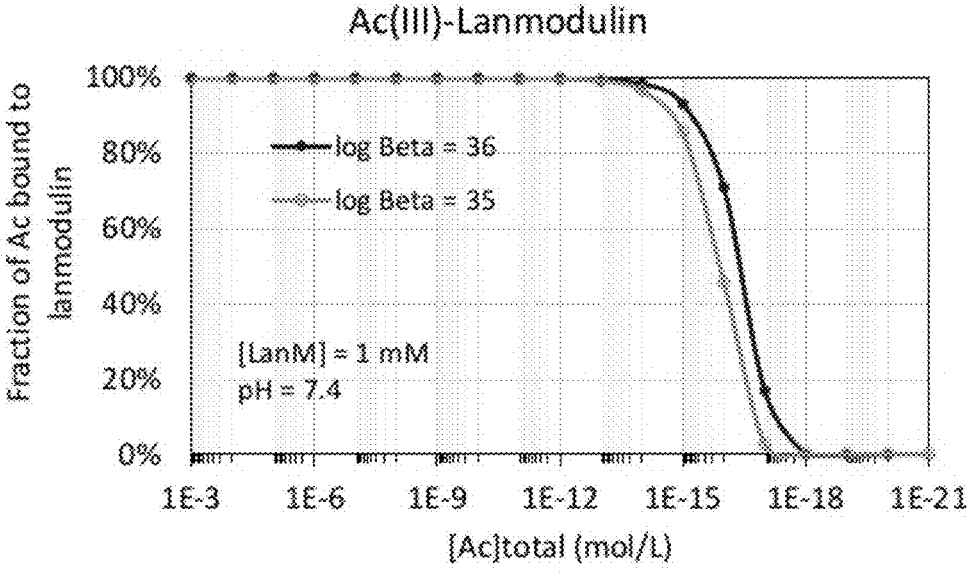

FIG. 39 is a graph of the amount of Ac-228 bound to LanM versus the total concentration of Ac-228 in the solution showing the unprecedented high affinity of LanM for radiometals, and in particular Ac (III).

Figure 40:
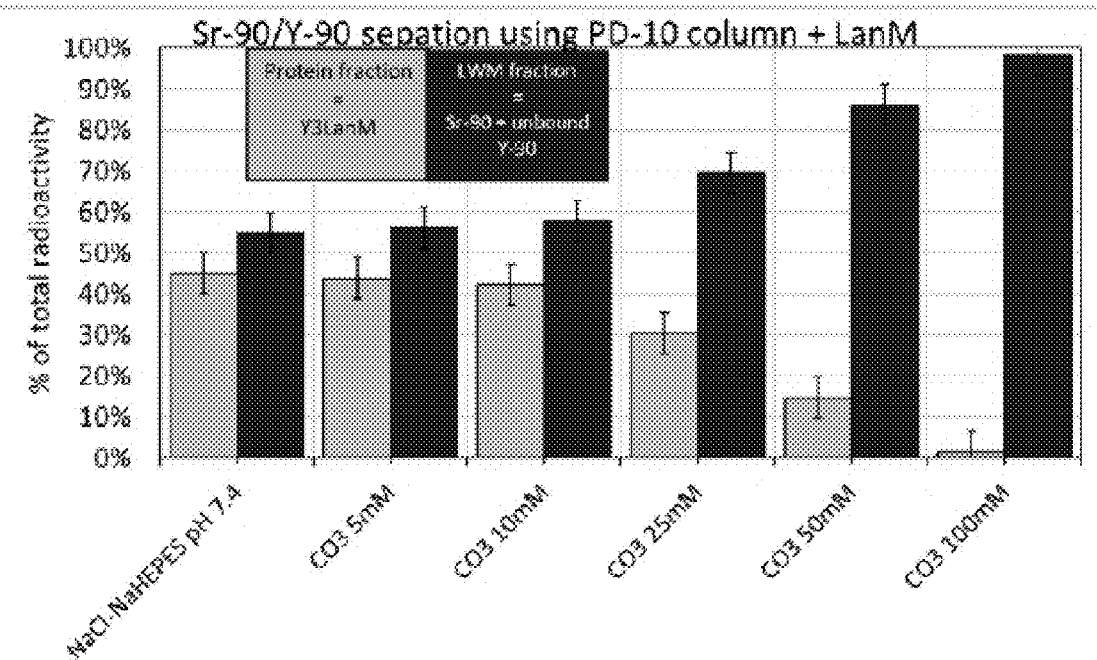

FIG. 40 is a graph of the radioactivity of the low molecular weight fraction (Sr-90) and the protein fraction (Y-LanM) with varying amounts of chelator in the aqueous solution as described herein.

Figure 41:
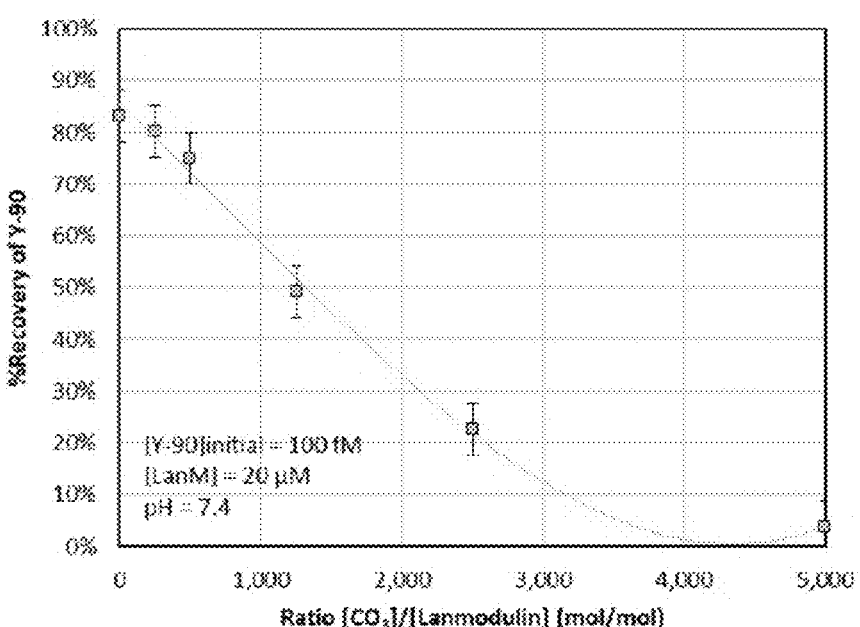

FIG. 41 is a graph of the recovery percentage of a Sr-90/Y-90 separation as disclosed herein with varying amounts of carbonate in the aqueous solution as described herein.

Figure 42:
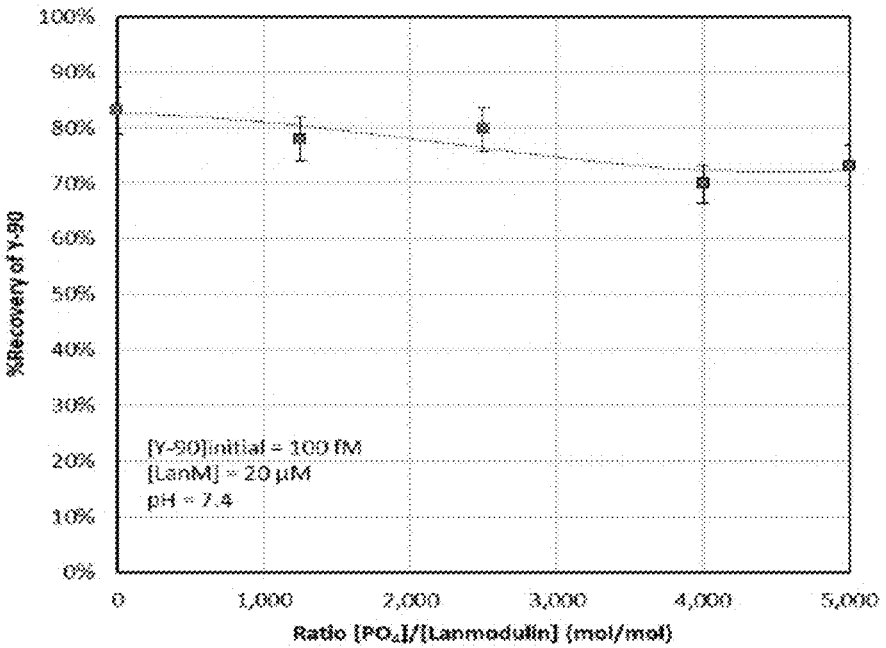

FIG. 42 is a graph of the recovery percentage of a Sr-90/Y-90 separation as disclosed herein with varying amounts of phosphate in the aqueous solution as described herein.

Figure 43:
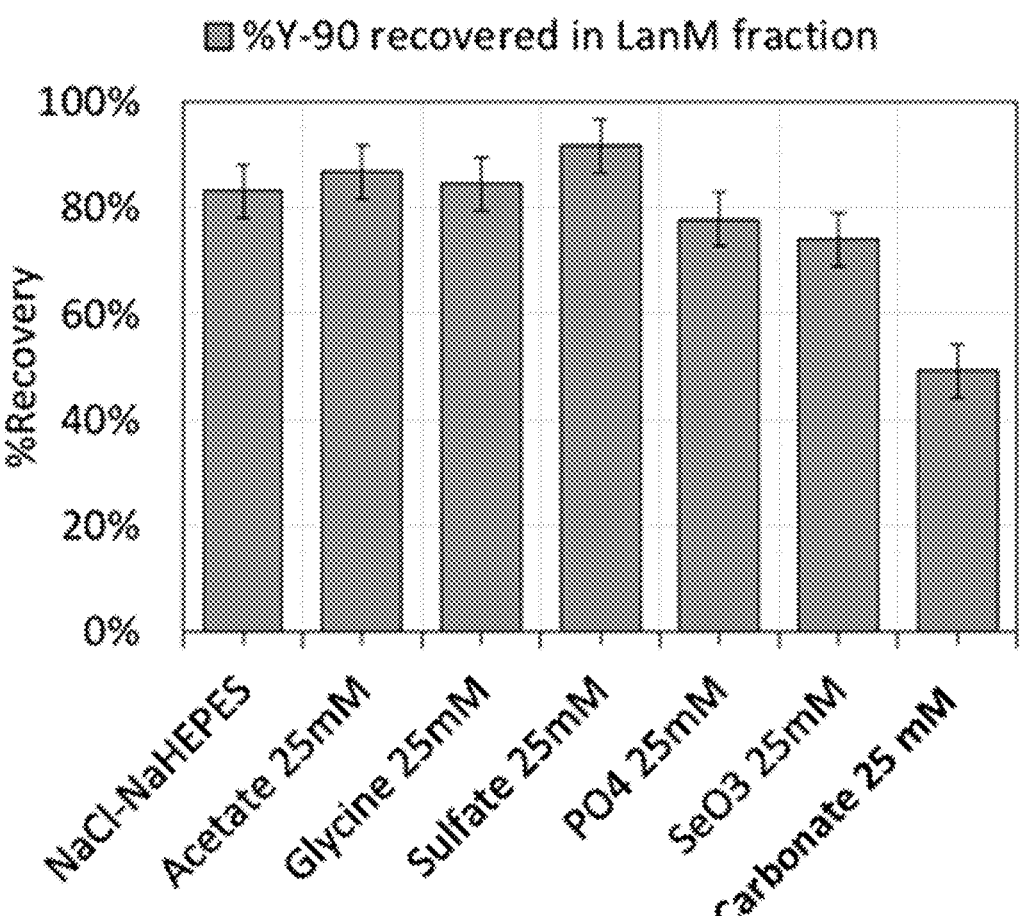

FIG. 43 is a graph of the recovery percentage of a Sr-90/Y-90 separation as disclosed herein with various chelators in the aqueous solution.

Figure 44:
Figure 44:
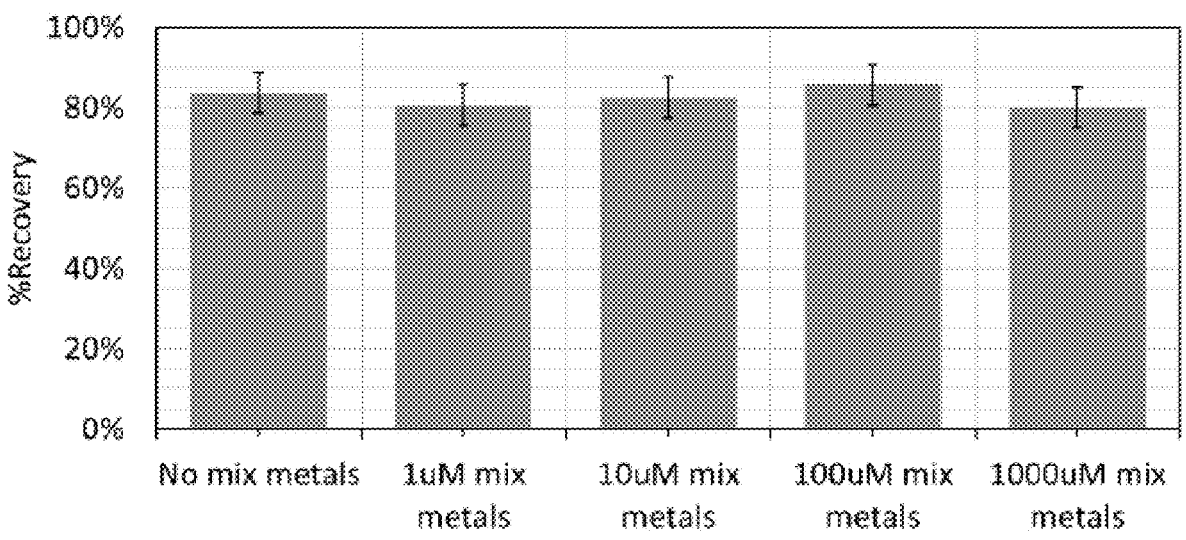

FIG. 44 is a graph of the recovery percentage of a Sr-90/Y-90 separation as disclosed herein with a mixture of metals (e.g., Mg2+, Ca2+, Mn2+, Zn2+, Cu2+) in the aqueous solution.

Figure 45:
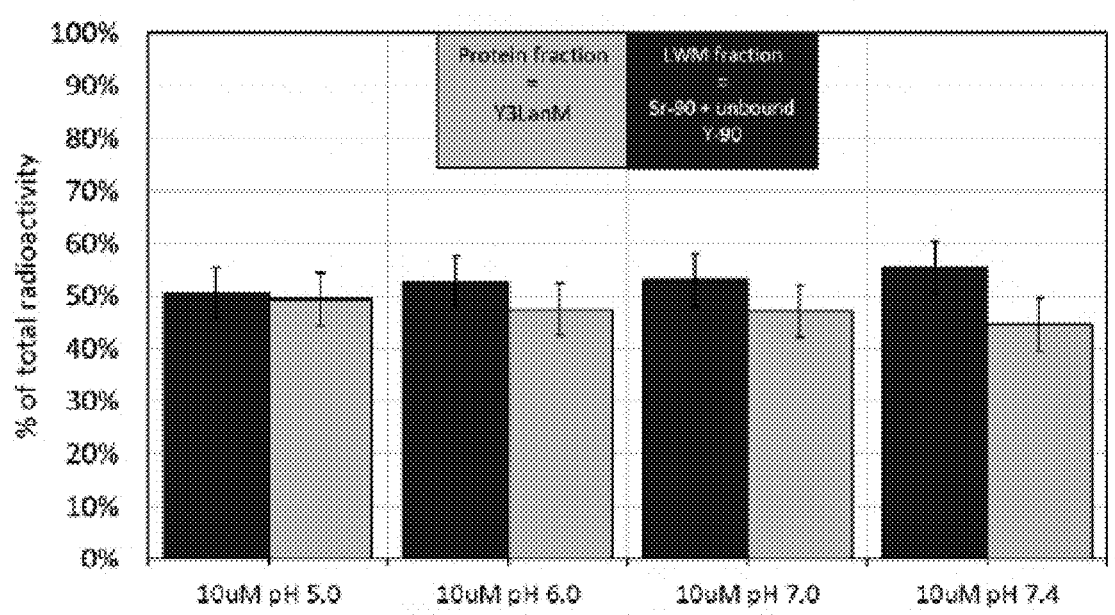

FIG. 45 graph of is a graph of the percentage of radioactivity of the protein fraction (Y-LanM) and the low molecular weight fraction (Sr-90) from a Sr-90/Y-90 separation as disclosed herein with a mixture of metals in the aqueous solution at varying pH levels.

Figure 46:
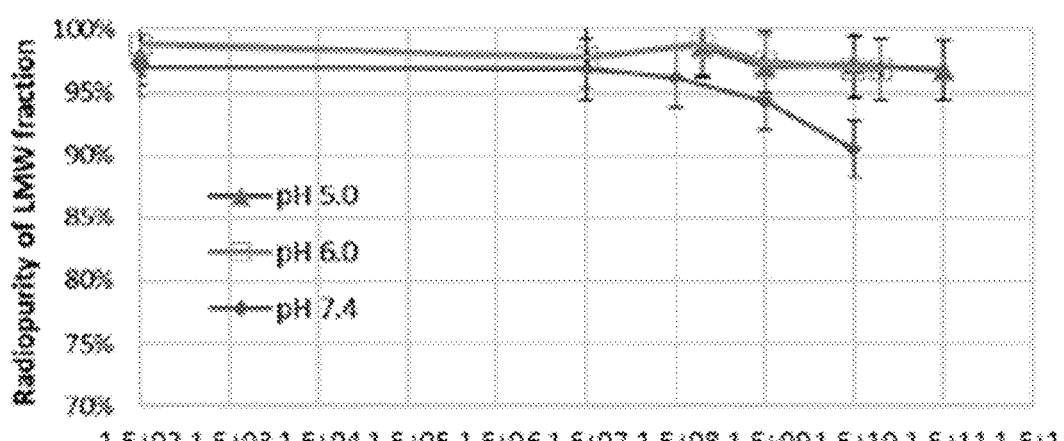

FIG. 46 is a graph of the radiopurity of the low molecular weight fraction from a Sr-90/Y-90 separation as disclosed herein with a mixture of metals in the aqueous solution at varying pH levels.

DETAILED DESCRIPTION

Provided herein are methods of sequestering a target element (e.g., one or more of a rare earth element (REE), Bi, Tl, In, and a radiometal) from a sample, methods of purifying an industrial feedstock or a pharmaceutical composition, methods of purifying a mixture of metals, methods of preparing a pharmaceutical composition, methods of treating cancer and methods of imaging a tumor, and a target element pharmaceutical composition using lanmodulin. In embodiments, the target element includes one or more of a rare earth element (REE), Bi, Tl, In, and a radiometal. In embodiments, the target element includes one or more of a rare earth element (REE), Bi, Tl, and In. In embodiments, the target element is one or more rare earth element. In embodiments, the target element is one or more radiometals. In embodiments, the target element is one or more of Bi, Tl, and In.

Lanmodulin (LanM) is a small protein of around 12 kDa produced by some methylotrophic organisms and is a natural lanthanide-modulated protein. Wild type *M. extorquens* LanM protein has a sequence of SEQ ID NO: 1, and can optionally be terminal His-tagged. Methods and composition of the disclosure utilize a LanM protein. Suitable LanM proteins include the wild type *M. extorquens* LanM protein, or homologs from other organism having at least two EF hand motifs, with at least one EF hand motifs having at least 3 carboxylate residues, and at least 2 of the EF hand motifs being separated by a space of 10-15 residues. Reference herein will be made generally to "lanmodulin," "LanM" or "LanM protein" and should be understood to include the wild type and homologs described herein. "LanM" can include full proteins having one or more LanM units or portions thereof comprising the one or more LanM units. LanM units include at least two EF hand motifs, with at least one EF hand motifs having at least 3 carboxylate residues, and at least 2 of the EF hand motifs being separated by a space of 10-15 residues. For ease of reference, discussion will be made with reference to lanmodulin, LanM or LanM protein and should be understood to include both the full proteins and portions of full proteins having the suitable LanM unit.

The unique features of the EF hands of this protein have been discussed previously in the initial characterization of the protein (Cotruvo et al., *J. Am. Chem. Soc.* 2018, 140, 44, 15056-15061). Based on biochemical and structural studies of the *M. extorquens* AM1 lanmodulin as well as homologs from other organisms, the lanmodulin protein domain has particular key characteristics. In many examples, at least one of the EF hands contained a proline residue at the second position. However, not all LanM homologs possess such a residue; yet they exhibit other key features of LanM that were identified, such as the spacing between at least 2 of the adjacent EF hands (10-15 residues, such as 12-13 residues) and additional carboxylate residues in the EF hands. In particular, the spacing between adjacent EF hands appears to be a hallmark of these proteins that sets them apart from traditional EF hand containing proteins, such as calmodulin. Even sequences with very low (<40%) identity to *M. extorquens* LanM can possess similar properties if the other general features mentioned above are conserved. In embodiments, the LanM is the *M. extorquens* wild type LanM having the sequence of SEQ ID NO:1, and can optionally be terminal His-tagged. In embodiments, the LanM can be a homolog of the wild type LanM. Suitable homologs have at least 2 EF hand motifs, with at least one EF hand motif having at least 3 carboxylate residues, and at least 2 of the EF hand motifs being separated by a spacer of 10-15 residues (including 12-13 residues). For example, the protein may include at least 1 and preferably at least 2 EF hand motifs of the form: (D/N)-X1-(D/N)-X2-(D/N)-X3-X4-X5-X6-X7-X8-(E/D) (SEQ ID NO: 2), wherein each numbered X is any residue (not necessarily the same residue in each position); X6 and/or X8 is a D or E, and glycine is preferred but not required at X3.

In embodiments, the LanM can include any natural or unnatural amino acid substituted into these EF hands, or elsewhere in the protein. In embodiments, the protein used in the methods of the disclosure can include any number of lanmodulin domains (referred to herein as LanM units) linked together with an appropriate amino acid spacer into a single polypeptide unit. In embodiments, the LanM includes only a single LanM unit. In embodiments, the LanM as used herein includes a proline residue at the second position. In embodiments, the LanM as used herein includes 10-15 residues between at least two adjacent EF hands, such as 12-13 residues. In embodiments, the LanM as used herein includes additional carboxylate residues in one or more of the EF hands, such as, 3 or more, 4 or more, or 5 or more, carboxylate residues.

wild-type *M. extorquens* LanM SEQ ID NO:1 (EF hand motifs underlined; sequence shown after removal of the predicted signal sequence)

PTTTTKVDIAAF<u>D</u>P<u>D</u>K<u>D</u>GTIDL<u>KE</u>ALAAGSAAFDKL<u>D</u>P<u>D</u>K<u>D</u>GTLDA<u>KE</u>L

KGRVSEADLKKL<u>D</u>P<u>D</u>N<u>D</u>GTLDK<u>KE</u>YLAAVEAQFKAAN<u>PD</u>N<u>D</u>GTIDA<u>RE</u>L

ASPAGSALVNLIREL

Some examples of homologs of the wild type include (note: sequences are shown after removal of the predicted signal sequence):

Example A: RH AL1 (SEQ ID NO: 3)

AKMDMKAI<u>D</u>P<u>D</u>S<u>D</u>GTVS<u>L</u>A<u>E</u>AQ<u>D</u>AAAKKFAAM<u>D</u>P<u>D</u>N<u>D</u>GTIDL<u>KE</u>AKGKM

AKAKFKK T<u>D</u>A<u>D</u>N<u>D</u>GTV<u>D</u>K<u>AE</u>YSALVESAFKAA<u>D</u>P<u>D</u>G<u>D</u>GTLDA<u>KE</u>LKTP

AGQKLLSLIQ

In this protein, one of the EF hands lacks a proline, and EF1 lacks a carboxylate at positions 9 and 11, but it still undergoes a conformational response at free concentrations of rare earth elements in the picomolar range.

Example B: *Hansschlegelia* sp. (SEQ ID NO: 4)

ASGADALKAL<u>NK</u>D<u>N</u>D<u>D</u>S<u>L</u>EIA<u>E</u>VIHAGATTFTAI<u>N</u>P<u>D</u>G<u>D</u>TTLESG<u>E</u>TKG

RLTEKDWARA <u>NK</u>D<u>GDQ</u>TLEMDEWLKILRTRFKRA<u>D</u>A<u>NK</u>DGKLTAAELD

SKAGQGVLVMIMK

In this protein (31% identity), only one of the EF hands has a proline at the second position, and only one has an Asp residue at the first position. However, it still undergoes a conformational response to free concentrations of rare earth elements in the picomolar range and much more weakly to other metals (e.g. calcium).

Example C: *Xanthomonas axonopodis* (SEQ ID NO: 5)

AQAQVQVQDSQQYLQRM<u>D</u>T<u>D</u>G<u>D</u>GRVS<u>LD</u>EYLAWMSYAFD<u>Q</u>R<u>D</u>T<u>D</u>H<u>D</u>GVL

QGDELPG RRGKPITRAAHRATLIARFAR<u>QD</u>A<u>N</u>G<u>D</u>GYLSAR<u>E</u>LLAPPR

This protein possesses ~33% sequence identity with *M. extorquens* LanM, it contains only 3 EF hands (underlined; referred to as EF1, EF2, and EF4 based on sequence alignment with the *M. extorquens* LanM), none of which have a proline, and yet it undergoes a conformational response to free concentrations of rare earth elements in the picomolar range and much more weakly to other metals (e.g. calcium). Note that, although EF1 and EF2 are only 13 residues apart, the distance between the adjacent EF2 and EF4 in this sequence is longer (25 amino acids) than in most lanmodulins because one of the EF hands (EF3) is missing.

Discussion of LanM can be found in Cotruvo et al., *Biochemistry* 58 (2), 120-125 (2019) and Cotruvo et al., *J. Am. Chem. Soc.* 2018, 140, 44, 15056-15061. LanM is more selective and robust than any known REE-binding macromolecules (e.g., proteins, synthetic peptides, etc.) and any known RM-binding macromolecules. LanM can maintain high activity and selectivity at low pH (i.e., from pH of 2.5 to 6.5) and/or high temperatures (e.g., 100° C.), whereas most proteins degrade in such harsh conditions. Industrial feedstocks and pharmaceutical compositions often have low pH's and/or are treated at high temperature and therefore, a protein that can sequester TEs from these sources without degrading in such conditions can be beneficial. Further, LanM will desorb a bound TE if the pH is lowered to less than 2.5, offering the ability of facile extraction of the TE atoms from the bound LanM-TE. As shown herein, LanM is resilient to repeated exposure to acidic conditions (e.g., a pH of less than 2.5, such as pH 2) and does not degrade for at least 7 repeated acid attacks. This allows the LanM to be recycled and used repeatedly, such as 10 times or more. In embodiments, the LanM can be used in the methods disclosed herein (e.g., the method steps can be repeated) with different samples at least two times, at least three times, at least ten times, e.g., 2, 3, 4, 5, 6, 7, 8, 9, 10, 15, 20, 25 or 30 times or more.

Provided herein are methods of sequestering a target element from a sample comprising contacting the sample and lanmodulin protein (LanM) in a first solution such that the target element (TE) binds to the lanmodulin to form TE-LanM, wherein the first solution is aqueous and has a pH of 2.5 to 6.5, the TE is one or more of a rare-earth element (REE), Bi, Tl, and In and the LanM protein comprises at least one LanM unit; recovering the TE-LanM from the first solution to form a second solution comprising the TE-LanM; adjusting the pH of the second solution to less than 2.5 such that the TE desorbs from the LanM; separating the LanM and the TE; and repeating the contacting, recovering, and adjusting steps with a second sample and the LanM at least once.

In embodiments, the target element is a rare-earth element (REE) such that the methods can comprise contacting the sample and lanmodulin protein (LanM) in a first solution such that the rare earth element (REE) binds to the lanmodulin to form REE-LanM, wherein the first solution is aqueous and has a pH of 2.5 to 6.5 and the LanM protein comprises at least one LanM unit; and recovering the REE-LanM from the first solution to form a second solution comprising the REE-LanM.

In some embodiments, it may be desired to isolate the TE from the sample, not simply remove it from the sample. As such, the methods disclosed herein can also comprise adjusting the pH of the second solution to less than 2.5 such that the TE desorbs from the LanM; and separating the LanM and the TE.

As used herein, the term "rare earth element" refers to elements that are relatively low in abundance on earth, including the elements: Sc, Y, La, Ce, Pr, Nd, Pm, Sm, Eu, Gd, Tb, Dy, Ho, Er, Tm, Yb, and Lu. The REEs that can bind to LanM include one or more of Sc, Y, La, Ce, Pr, Nd, Pm, Sm, Eu, Gd, Tb, Dy, Ho, Er, Tm, Yb, and Lu. In some cases, the REE is a radioactive isotope of a REE. For example, the radioactive isotope of a REE can include, but is not limited to, one or more of $^{44}$Sc, $^{47}$Sc, $^{90}$Y, $^{134}$Ce, $^{134}$La, $^{86}$Y, $^{88}$Y, $^{139}$Ce, $^{149}$Tb, $^{153}$Gd, $^{177}$Lu, $^{165}$Dy, $^{152}$Eu, $^{153}$Sm, $^{147}$Pm, $^{166}$Ho, $^{169}$Yb, $^{176}$Yb, $^{152}$Tb, $^{155}$Tb, and $^{161}$Tb.

In embodiments, the target element is a radioactive isotope. For example, the radioactive isotope of a target element can include, but is not limited to, $^{212}$Bi, $^{213}$Bi, $^{111}$In, and $^{201}$Tl.

Also provided herein are methods of sequestering a radiometal from a sample. The methods can comprise contacting the sample and lanmodulin protein (LanM) in a first solution such that the radiometal (RM) binds to the lanmodulin to form RM-LanM, wherein the first solution is aqueous and has a pH of 2.5 to 10 and the LanM protein comprises at least one LanM unit; and recovering the RM-LanM from the first solution to form a second solution comprising the RM-LanM. In embodiments, the method can include adjusting the pH of the second solution to less than 2.5 such that the RM desorbs from the LanM; separating the LanM and the RM; and repeating the contacting, recovering, and adjusting steps with a second sample and the LanM at least once. In embodiments, the first solution has a pH of 2.5 to 9, or 2.5 to 8, or 2.5 to 7, or 2.5 to 6.5. The methods of sequestering a radiometal disclosed herein can include higher pH conditions (e.g., higher than 6.5) compared to the methods disclosed of the target metals wherein the target metals are rare-earth elements and Bi, Tl, or In, because the concentration of radiometals is generally much lower in the sample and therefore, less hydrolysis occurs and there are no precipitation problems.

As used herein, the term "radiometal" refers to metals that are or can be radioactive, including the elements: Ac, Th, Pa, U, Np, Pu, Am, Cm, Bk, Cf, Es, Fm, Md, No, Lr, Ra, and Zr. In embodiments, the RMs can include one or more of Ac, Th, U, Np, Pu, Am, Cm, Bk, Cf, Es, Fm, Md, Lr, and Zr. In embodiments, the RMs that can bind to LanM include one or more of Ac, U, Np, Pu, Am, Cm, Bk, Cf, Es, Fm, Md, and Lr, in the +3 oxidation state. In embodiments, the radioactive isotope of the radiometals can include, but is not limited to, one or more of $^{225}$Ac, $^{226}$Ac, $^{228}$Ac, $^{227}$Ac, $^{233}$U, $^{235}$U, $^{239}$Pu, $^{240}$Pu, $^{241}$Pu, $^{244}$Pu, $^{241}$Am, $^{243}$Am, $^{244}$Cm, $^{246}$Cm, $^{247}$Cm, $^{248}$Cm, $^{250}$Bk, $^{249}$Bk, $^{248}$Bk, $^{247}$Bk, $^{252}$Cf, $^{249}$Cf, $^{253}$Es, $^{254}$Es, and $^{255}$Fm.

The methods disclosed herein can provide a recovery yield of TEs from a sample of 70% or more. In embodiments, the recovery yield can be from 70% to 100%, such as, 70%, 75%, 80%, 85%, 90%, 95%, 96%, 97%, 98%, 99%, 99.5%, 99.9%, or 100%. In embodiments, the recovery yield of TEs from a sample can 90% or more, such as, 90%, 95%, 96%, 97%, 98%, 99%, 99.5%, 99.9%, or 100%.

It is also contemplated herein for the LanM to be used for purification of a sample such that target elements are removed and the non-target elements are recovered. For example, the recovery of Np-239 in a mixture of Am-243 and Np-239. The LanM can be added to the mixture which will bind to Am-243 and the purified Np-239 can be recovered.

Lanmodulin Protein

The LanM protein, as described above, can be used in the methods disclosed herein in an aqueous solution. The aqueous solutions including the LanM protein and target elements, wherein the target elements are rare-earth metals, can have a pH of 2.5 to 6.5. In embodiments, the aqueous solution can have a pH of 2.5 to 6, or 2.5 to 5.5, or 2.5 to 5, or 3 to 5.5, or 4 to 5, such as, 2.5, 3, 3.5, 4, 4.5, 5, 5.5, or 6. The aqueous solution including the LanM protein and radiometals, can have a pH of 2.5 to 10. In embodiments, the aqueous solution can have a pH of 2.5 to 9, or 2.5 to 8, or 2.5 to 7.5, or 2.5 to 6.5, or 3 to 5.5, or 4 to 5, such as, 2.5, 3, 3.5, 4, 4.5, 5, 5.5, 6, 7, 7.5, 8, 8.5, 9, or 9.5. In embodiments, wherein the aqueous solution has a lower pH, such as 5 or less, the LanM may bind metals with a charge of +4.

In embodiments, the LanM can be bound to a support (LanM-support) and used in the disclosed methods. In embodiments, the support can comprise a sponge, a powder, a resin, a filter, a gel, or a combination thereof. For example, the LanM can be bound to a support, e.g., a resin, and placed in a column through which a sample comprising the TE can be flowed. Upon contact with the support bound LanM, the TE can bind to the LanM on the support (e.g., remain in the column) as the sample flows through. After contact with the sample, and binding of the TE to the LanM, the column can then be subjected to conditions to release the TE from the LanM in the column, e.g., adjusting the pH to less than 2.5, such as 2, conditions that are discussed in detail below.

The LanM protein in embodiments of the disclosure can include one or more LanM units. In embodiments, the LanM protein can include two or more LanM units linked by an appropriate spacer. Each LanM unit can bind up to four TEs per protein molecule. For example, each LanM unit can bind one, two, three, or four TEs per protein molecule, such that the TE-LanM can have one, two, three, or four TEs per unit. In embodiments, each LanM unit can bind up to four REEs. In embodiments, each LanM unit can bind up to four RMs. In embodiment's the LanM can include multiple LanM units and can bind up to four TEs per unit. For example, if 3 LanM units are linked, each LanM unit can bind up to four TEs, therefore a total of up to 12 TEs can be bound to the LanM protein having 3 linked LanM units.

In embodiments, the LanM has a TE selectivity of $10^3$ or more. As used herein, "TE selectivity" refers to $K_d Ca^{2+}/K_d TE^{3+}$, such that the binding of a TE to LanM is compared to the LanM's binding to $Ca^{2+}$, using a protocol as discussed in the examples below. In embodiments, the LanM has a TE selectivity of $10^5$ or more. In embodiments, the LanM has a TE selectivity of $10^7$ or more at a pH of 5. In embodiments, the LanM has a TE selectivity of $10^7$ or more at a pH of 7. For example, the LanM has a TE selectivity of $10^3$, $10^4$, $10^5$, $10^6$, $10^7$, $10^8$, $10^9$, or $10^{10}$. In embodiments, the LanM can have an affinity ($K_d$) to TEs per binding site of 0.01 pM to 30 pM or 0.1 pM to 25 pM, or 0.5 pM to 25 pM. For example, the LanM can have an affinity ($K_d$) to TEs per binding site of 0.1 pM, 0.5 pM, 1 pM, 1.5 pM, 2 pM, 5 pM, 10 pM, 15 pM, 20 pM, 25 pM, or 30 pM.

In embodiments, the LanM has a RM selectivity of $10^3$ or more. As used herein, "RM selectivity" refers to $K_d^{228}Ra/K_d RM^{3+}$ such that the binding of a RM to LanM is compared to the LanM's binding to $^{228}$Ra, using a protocol as discussed in the examples below. In embodiments, the LanM has a RM selectivity of $10^4$ or more. In embodiments, the LanM has a RM selectivity of $10^6$ or more. In embodiments, the LanM can have an affinity ($K_d$) to RMs per binding site of 1 nM or less, or 100 pM or less, or 10 pM or less, at a pH of about 5.0. In embodiments, LanM has an affinity ($K_d$) to RMs per binding site of 0.01 pM to 30 pM or 0.1 pM to 25 pM, or 0.5 pM to 25 pM, at a pH of about 5.0. For example, the LanM has an affinity ($K_d$) to RMs per binding site of about 0.1 pM, 0.5 pM, 1 pM, 1.5 pM, 2 pM, 3 pM, 4 pM, 4.5 pM, 5 pM, 6 pM, 7 pM, 10 pM, 15 pM, 20 pM, 25 pM, or 30 PM, at a pH of about 5.0. In embodiments, the methods herein can provide for the sequestration of an RM, wherein the RM has a concentration in the femtomolar range (e.g., $1 \times 10^{-15}$ M to about $1000 \times 10^{-15}$ M, or $1 \times 10^{-15}$ M to about $100 \times 10^{-15}$ M) in the sample.

Samples for TE Isolation and/or Sequestration

The sample of the methods disclosed herein can be any particular sample that comprises, or is suspected of comprising, a target element (e.g., one or more of a rare earth element, Bi, Tl, In, and a radiometal). In embodiments, the sample can further comprise other elements, such as non-rare earth elements, and other non-target elements (non-TEs). In embodiments, the sample can further comprise non-radiometal elements (non-RMs), e.g., an element that is not a radiometal. LanM is selective for binding to REEs, Bi, In, Tl, radiometals, or a combination thereof. Non-TEs do not bind to the LanM, see discussion about REE/RM selectivity herein. Non-limiting examples of non-TEs that can be present the sample for methods disclosed herein include Li, Na, K, Mg, Ca, Sr, Rb, Cs, Ba, Al, Si, Mn, Fe, Co, Ni, Cu, Zn, Ti, Sn, V, or a combination thereof. In some cases, the sample comprises Fe, Co, Cu, Ca, Mg, or a combination thereof. In embodiments, the non-TEs can include one or more radioisotopes that do not bind to LanM or LanM otherwise has a weak affinity for, such as Ra-224, Ra-228, Ti-44, Np-239, and Pa-231. Non-limiting examples of non-RMs that can be present the sample for methods disclosed herein include Li, Na, K, Mg, Ca, Sr, Rb, Cs, Ba, Al, Si, Mn, Fe, Co, Ni, Cu, Zn, Ti, Sn, V, or a combination thereof. In embodiments, the concentration of non-TEs in the sample or in the first solution is up to 3 M. In embodiments, the concentration of non-TEs in the sample or in the first solution is up to 1.5 M. For example, the concentration of non-TEs in the sample or in the first solution is up to 1.5 M, such as, 1.5 M, 1.4 M, 1.3 M, 1.2 M, 1.1 M, 1 M, 0.8 M, 0.5 M, 0.3 M, 0.1 M, 0.05 M, 10 mM, 5 mM, 1 mM, 0.1 mM, 0.05 mM. In embodiments, the concentration of non-TEs in the sample or in the first solution is at least 0.05 mM. In embodiments, the LanM is selective for binding to TEs even in environments (i.e., samples or solutions) with high concentrations of non-TEs (e.g. 1.5 M or more). In embodiments, the concentration of non-RMs in the sample or in the first solution is up to 3 M. In embodiments, the concentration of non-RMs in the sample or in the first solution is up to 1.5 M. For example, the concentration of non-RMs in the sample or in the first solution is up to 1.5 M, such as, 1.5 M, 1.4 M, 1.3 M, 1.2 M, 1.1 M, 1 M, 0.8 M, 0.5 M, 0.3 M, 0.1 M, 0.05 M, 10 mM, 5 mM, 1 mM, 0.1 mM, 0.05 mM. In embodiments, the concentration of non-RMs in the sample or in the first solution is less than 0.5 mM. In embodiments, the LanM is selective for binding to RMs even in environments (i.e., samples or solutions) with high concentrations of non-RMs (e.g. 1.5 M or more). In embodiments, the LanM is selective for binding RMs in environments with very low concentrations of both RMs and non-RMs (e.g. 1 nM or less).

In embodiments, the sample can comprise an industrial feedstock. In embodiments, the industrial feedstock can be non-combusted coal, electronic waste, natural waters (e.g., geothermal brine), waste streams, radioisotope production compositions, industrial effluents, ore deposits, or a combination thereof. In embodiments, the electronic waste can comprise electronic waste leachate or the like. In embodiments, the waste streams can be those waste streams from rare earth milling and processing, such as the tailing and its associated treatment and storage. In embodiments, the waste streams can be off-gases from dehydrogenation, spent hydroxide cake, spent monazite solids, spent off-gases from electrolytic reduction, spent sodium fluoride, waste filtrate, waste solvent, spent lead filter cake, lead backwash sludge, waste zinc contaminated with mercury, solvent extraction crud, or a combination thereof (EPA Publication: Rare Earth Elements: A Review of Production, Processing, Recycling, and Associated Environmental Issues (2012)). In embodiments, the industrial effluents can include effluents released into the environment, such as, water treatment plant effluents, hospital effluents, acid mine drainage or the like, or radioisotope facility effluents. In embodiments, the sample can comprise waste streams such as from a patient following medical procedures, wherein the waste stream ends up in sewage. In embodiments, the hospital effluents can include, but are not limited to, MRI contrast agents. In embodiments, the ore deposits comprise one or more rare-earth elements. In embodiments, the ore deposits comprise one or more of bastnaesite, monazite, allanite, and the like.

In embodiments, the industrial feedstock described herein can have a concentration of TEs and non-TEs, independently, of 1 parts per billion (ppb) to 500,000,000 ppb. For example, the concentration of TEs and non-TEs, independently, can be 10 ppb to 300,000,000 ppb, or 100 ppb to 150,000,000 ppb, or 1000 ppb to 120,000,000 ppb, or 1000 ppb to 10,000,000 ppb, or 100 ppb to 1,000,000 ppb, or 1 ppb to 500,000 ppb. In embodiments, the feedstock can include one or more rare earth elements as the target elements. In embodiments, the feedstock can include one or more of Bi, In, and Tl. In embodiments the feed stock can include one or more rare earth elements and one or more of Bi, In, and Tl.

In embodiments, the industrial feedstocks described herein can have a concentration of RMs and non-RMs, independently, of 0.000,001 ppb to 500,000,000 ppb. For example, the concentration of RMs and non-RMs, independently, can be 0.000,001 ppb to 1000 ppb, 0.000,01 ppb to 1000 ppb, 0.0001 ppb to 1000 ppb, 0.001 ppb to 1000 ppb, 0.01 ppb to 1000 ppb, 0.1 ppb to 1000 ppb, 1 ppb to 1000 ppb, 1 ppb to 300,000,000 ppb, or 100 ppb to 150,000,000 ppb, or 1000 ppb to 120,000,000 ppb, or 1000 ppb to 10,000,000 ppb, or 100 ppb to 1,000,000 ppb, or 1 ppb to 500,000 ppb.

In embodiments, the sample can comprise a pharmaceutical composition. In embodiments, the pharmaceutical composition can be medical waste effluents, medical waste ash, medical device leachate, or waste from the production and processing of drug synthesis. In embodiments, the pharmaceutical composition can comprise waste from medical isotope generators, for example, compositions containing radioactive $^{177}Lu^{3+}$, compositions containing radioactive $^{47}Sc^{3+}$ and its non-radioactive daughter $^{47}Ti$, compositions containing radioactive $^{47}Ca^{2+}$ and its radioactive daughter $^{47}Sc^{3+}$, compositions containing radioactive $^{90}Sr^{2+}$ and $^{90}Y^{3+}$, compositions containing radioactive $^{86}Sr^{2+}$ and $^{86}Y^{3+}$, compositions containing radioactive $^{225}Ac^{3+}$ and other metal ions such as $^{233}UO_2^{2+}$, $^{227}Ac^{3+}$, $^{226/223}Ra^{2+}$, $^{226}Ac^{3+}$ and $^{226}Ra^{2+}$, or $^{228}Ac^{3+}$ and $^{228/224}Ra^{2+}$. In embodiments, the pharmaceutical compositions can include an aqueous solution at about physiological pH (e.g., 7.4).

In embodiments, the sample can comprise a mixture of metals, including mixtures of radioactive and non-radioactive metals. In embodiments, the mixture of metals can include one or more of $^{90}Y^{3+}$ and $^{90}Sr^{2+}$: $^{44}Sc^{3+}$ and $^{44}Ti^{4+}$; $Nd^{3+}$ and $^{241}Pu^{4+}$; $^{17}Lu$ and $Hf^{4+}$; $^{243}Am^{3+}$ and $^{239}Np$; $^{241}Am^{3+}$ and $^{237}Np$; $^{227}Ac^{3+}$ and $^{231}Pa$; $^{225}Ac^{3+}$ and $^{29}Th^{4+}$; $^{227}Ac^{3+}$ and $^{235}UO_2^{2+}$: $^{227}Ac^{3+}$ and $^{226}Ra^{2+}$: $^{228}Ac^{3+}$ and $^{228}Ra^{2+}$; $^{225}Ac^{3+}$ and $^{233}UO_2^{2+}$; $^{247}Cm^{3+}$ and $^{243}Pu^{4+}$. $^{247}Cm^{3+}$ and $^{243}PuO^{2+}$; $^{249}BK^{3+}$ and $^{249}Cf^{3+}$: $^{239}Pu^{3+}$ and $^{235}UO^{4+}$; $^{239}Pu^{3+}$ and $^{235}UO_2^{2+}$. $^{242}Pu^{3+}$ and $^{238}U^{4+}$, $^{242}Am^{3+}$ and $^{242}Pu^{4+}$; $^{242}Am^{3+}$ and $^{242}PuO^{2+}$.

In embodiments, the mixture of metals can comprise, a radiometal (RM), as disclosed herein, having a +3 oxidation state [RM (III)] and a metal having an oxidation state other than +3 [M (III*)] as disclosed above. In embodiments, the mixture of metals includes non-rare earth elements as disclosed above. In embodiments, the mixture of metals includes one or more radioactive elements having an oxidation state other than +3. For example, the mixture of metals can include one or more of: $^{243}Am$ and $^{239}Np$; $^{241}Pu$ and $^{241}Am$; $^{243}Pu$, $^{243}Am$, and $^{247}Cm$; $^{227}Ac$, $^{227}Th$, and $^{223}Ra$; $^{228}Ac$, $^{228}Th$, $^{228}Ra$, and $^{232}Th$; $^{225}Ac$ and $^{233}U$; $^{240}Pu$ and $^{244}Cm$; $^{225}Ac^{3+}$, $^{233}UO_2^{2+}$, $^{229}Th^{4+}$, and $^{225}Ra^{2+}$; and, $^{249}Bk^{4+}$ and $^{249}Cf^{3+}$.

Sample and LanM Contacting

Contacting of the LanM and the sample having the TE can be performed at a temperature of 0° C. to 100° C. For example, the contacting can be performed at a temperature of 4° C. to 95° C., or 10° C. to 95° C., or 20° C. to 90° C., or 20° C. to 60° C., such as, 0° C., 4° C., 10° C., 20° C., 25° C., 30° C., 40° C., 50° C., 60° C., 70° C., 80° C., 90° C., 95° C., or 100° C. In some cases, the contacting can be performed at 50° C. to 95° C. or 60° to 95° C.

The contacting can be performed at a pressure of 0.01 atm to 10 atm. For example, the contacting can be performed at a pressure of 0.1 atm to 5 atm, or 0.5 atm, to 4 atm, or 1 atm to 3 atm, such as, 0.1 atm, 0.5 atm, 0.7 atm, 0.8 atm, 0.9 atm, 1 atm, 1.1 atm, 2 atm, 3 atm, 4 atm, or 5 atm. In embodiments, contacting can be performed at atmospheric pressure, e.g., 1 atm.

Recovery of TE-Bound to LanM

The TE and LanM, once bound together (as TE-LanM) can be recovered from the sample and LanM mixture (the first solution). Recovery of the TE-LanM (e.g., REE-LanM or RM-LanM) can be performed by any method suitable, as determined by one of ordinary skill in the art. For example, recovery can be by size-exclusion filtration, size-exclusion chromatography, protein affinity chromatography, ion-exchange chromatography, hydrophobic interaction chromatography, affinity chromatography, desalting column chromatography, centrifugation, reverse osmosis, nanofiltration, electrophoresis, protein precipitation, or a combination thereof.

The recovered TE-LanM is present in a second solution. In embodiments, the second solution is aqueous. In embodiments, the second solution has a pH of at least 2.5 in the recovering step, for example, 2.5 to 6.5, or 2.5 to 5.5, or 2.5 to 5, or 3 to 5.5, or 3.5 to 5, or 2.5 to 4.5, such as 2.5, 3, 3.5, 4, 4.5, 5, 5.5, 6, 7, 7.2, or 7.5. The aqueous solution including the RM-LanM, can have a pH of 2.5 to 10. In embodiments, the aqueous solution can have a pH of 2.5 to 9, or 2.5 to 8, or 2.5 to 7.5, or 2.5 to 6.5, or 3 to 5.5, or 4 to 5, such as, 2.5, 3, 3.5, 4, 4.5, 5, 5.5, 6, 7, 7.5, 8, 8.5, 9, or 9.5.

In embodiments, the second solution can further comprise a chelator suitable to one of ordinary skill in the art.

Desorption of TE from TE-LanM

The TE can be desorbed from the TE-LanM to obtain free TE. In embodiments, the REE can be desorbed from the REE-LanM to obtain free REE. In embodiments, the RM can be desorbed from the RM-LanM to obtain free RM. This desorption can be achieved by exposing the TE-LanM to a pH less than 2.5. In embodiments, the RM can be desorbed from the RM-LanM to obtain free RM. This desorption can be achieved by exposing the RM-LanM to a pH less than 2.5. In embodiments, the pH of the second solution (the solution of the recovered TE-LanM) is adjusted to a pH less than 2.5. In embodiments, the adjusting can be performed by the addition of any acid suitable, as determined by one of ordinary skill in the art to lower the pH to less than 2.5. For example, the acid can comprise a strong acid, such as, HCl, $HNO_3$, $H_2SO_4$, HBr, HI, $HClO_4$, $HClO_3$, or a combination thereof. In embodiments, the adjusting can be performed by the addition of any low-pH buffered solution, as determined by one of ordinary skill in the art to lower the pH to less than 2.5. For example, the low-pH buffered solution can comprise a glycine, formic acid, acetic acid, citric acid, dihydrogen phosphate, alanine, leucine, valine, proline solution, or a combination thereof. Further, once the pH is less than 2.5, the TE desorbs from the LanM. In embodiments, the pH is adjusted to 1 to 2, or 1.5 to 2.4, or 1.5 to 2, or 2 to 2.3.

Once desorbed from the LanM, the TE can be separated from the LanM. Separating can be performed by any suitable method, as determined by one of ordinary skill in the art. For example, separating the LanM and the TE can be performed by centrifugation, filtration, reverse osmosis, nanofiltration, chromatography (e.g., desalting column chromatography, gel filtration column chromatography, ion exchange chromatography, hydrophobic interaction chromatography, affinity chromatography), electrophoresis, protein precipitation, or a combination thereof. Non-limiting examples of viable commercially available filtration systems include: "PD-10 desalting column G-25, PD-10 SpinTrap™ G-25, PD-10 MultiTrap™ G-25, PD-10 MiniTrap™ G-25, PD-10 HiTrap™ G-25, PD-10 MiniTrap™ G-10, PD-10 MidiTrap™ G-10" manufactured by Cytiva, "Amicon® Pro or Ultra Filters" manufactured by Millipore Sigma, "Spin-X® UF concentrators" manufactured by Corning®, "Pierce™ Protein Concentrators" manufactured by Thermo Scientific, "VivaSpin Filters" manufactured by Viva products, "Nanosep®, Macrosep®, Jumbosep™, and MiniMate™ manufactured by PALL, and "Dialysis tubing" Sigma Aldrich.

In the alternative or in combination to lowering the pH to less than 2.5, the TE can be desorbed and/or recovered by the addition of one or more chelators suitable to one of ordinary skill in the art.

Pharmaceutical Compositions with Te-LanM

In embodiments, a target element (TE) pharmaceutical composition can include (i) a TE bound to a LanM or modified lanmodulin protein (LanM) and (ii) at least one pharmaceutically acceptable excipient, wherein the modified LanM is LanM modified with a targeting moiety. In embodiments, the target element (TE) pharmaceutical composition includes one or more rare-earth metals, Bi, Tl, and In. In embodiments, the TE pharmaceutical composition include one or more rare-earth metals. In embodiments, the TE pharmaceutical composition includes one or more radio-metals. In embodiments, the REE can comprise one or more of Sc, Y, La, Ce, Pr, Nd, Pm, Sm, Eu, Gd, Tb, Dy, Ho, Er, Tm, Yb, and Lu. In some cases, the REE includes one or more radioactive isotope, e.g., one or more of $^{44}$Sc, $^{47}$Sc, $^{90}$Y, $^{134}$Ce, $^{134}$La, $^{86}$Y, $^{88}$Y, $^{139}$Ce, $^{149}$Tb, $^{153}$Gd, $^{177}$Lu, $^{165}$Dy, $^{152}$Eu, $^{153}$Sm, $^{147}$Pm, $^{166}$Ho, $^{169}$Yb, $^{176}$Yb, $^{152}$Tb, $^{155}$Tb, and $^{161}$Tb. In embodiments, the pharmaceutical compositions can include an aqueous solution at about physiological pH (e.g., 7.4).

The TE pharmaceutical composition comprising (i) a TE bound to a LanM protein or modified lanmodulin protein (LanM) and (ii) at least one pharmaceutically acceptable excipient, as described herein, can be prepared by contacting a TE and LanM) in a first solution such that the target element (TE) binds to the lanmodulin or modified LanM to form TE-LanM. The method further includes recovering the TE-LanM from the first solution; and admixing the TE-LanM with a pharmaceutically acceptable excipient to form the TE pharmaceutical composition. In embodiments, the first solution can be an aqueous solution having a pH in a range of 2.5-10. In embodiments, it can be advantageous for pharmaceutical applications to maintain the pH of the first solution at or around physiological pH (about 7.4). In embodiments, the first solution can be prepared at below physiological pH, such as a pH of 2.5 to 6.5 and the pH of the recovered TE-LanM can be adjusted if needed to physiological pH.

The modified LanM can comprise any suitable targeting moiety, as determined by one of ordinary skill in the art. The targeting moiety allows for the TE bound LanM to be directed to a desired area within a subject. In embodiments, the targeting moiety can comprise an antibody, a peptide, a small organic molecule, or a combination thereof. In embodiments, the small organic molecule can have molecular weight of less than 1500 Da, less than 1200 Da, less than 1000 Da, or less than 800 Da. The targeting moiety can be specific for a tumor associated antigen, such that the TE bound LanM is directed to a tumor in the subject. Discussion and design of antibody-drug conjugates (ADCs) are prevalent, including suitable targeting moieties and linkers for attaching a targeting moiety to a drug (here, the TE bound LanM). See, e.g., U.S. Pat. Nos. 10,537,644; 10,442,860; 10,413,621.

In embodiments, the TE pharmaceutical composition can further comprise non-TEs and/or contact non-TEs when administered to a subject. For example, the subject likely has circulating Ca, Fe, Cu, Mg, Zn, Mn, or the like, but the selectivity of the LanM for the TE is such that the TE will not be displaced by these other non-TEs in the subject. This REE-selectivity of the LanM can ensure the TE stays bound to the LanM and will circulate to the desired area within the subject for the desired end use (e.g., as a therapeutic or for imaging). Non-limiting examples of non-TEs that can be present in the REE pharmaceutical composition disclosed herein or in the subject include one or more of Li, Na, K, Mg, Ca, Sr, Rb, Cs, Ba, Al, Si, Mn, Fe, Co, Ni, Cu, Zn, Ti, Sn, and V. In some cases, the TE pharmaceutical composition or the subject comprises one or more of Fe, Co, Cu, Ca, and Mg.

In embodiments, a radiometal (RM) pharmaceutical composition can include (i) a RM bound to a modified lanmodulin protein (LanM) and (ii) at least one pharmaceutically acceptable excipient, wherein the modified LanM is LanM modified with a targeting moiety. In embodiments, the RM can comprise one or more of Ac, Th, Pa, U, Np, Pu, Am, Cm, Bk, Cf, Es, Fm, Md, No, Lr, Ra, and Zr. In some cases, the RM is a radioactive isotope, e.g., one or more of $^{225}$Ac, $^{226}$Ac, $^{228}$Ac, $^{227}$Ac, $^{233}$U, $^{235}$U, $^{239}$Pu, $^{240}$Pu, $^{241}$Pu, $^{244}$Pu, $^{241}$Am, $^{243}$Am, $^{244}$Cm, $^{246}$Cm, $^{247}$Cm, $^{248}$Cm, $^{250}$Bk, $^{249}$Bk, $^{248}$Bk, $^{247}$Bk, $^{252}$Cf, $^{249}$Cf, $^{253}$Es, $^{254}$Es, and $^{255}$Fm.

The RM pharmaceutical composition comprising (i) a RM bound to a LanM or modified lanmodulin protein (LanM) and (ii) at least one pharmaceutically acceptable excipient, as described herein, can be prepared by contacting a RM and LanM in a first solution such that the RM binds to the lanmodulin to form RM-LanM; recovering the RM-LanM from the first solution; and admixing the RM-LanM with a pharmaceutically acceptable excipient to form the RM pharmaceutical composition. In embodiments, the first solution can be an aqueous solution having a pH in a range of 2.5-10. In embodiments, it can be advantageous for pharmaceutical applications to maintain the pH of the first solution at or around physiological pH (about 7.4). In embodiments, the first solution can be prepared at below physiological pH, such as a pH of 2.5 to 6.5 and the pH of the recovered TE-LanM can be adjusted if needed to physiological pH.

The modified LanM can comprise any suitable targeting moiety, as determined by one of ordinary skill in the art. The targeting moiety allows for the RM bound LanM to be directed to a desired area within a subject. In embodiments, the targeting moiety can comprise an antibody, a peptide, a small organic molecule, or a combination thereof. The targeting moiety can be specific for a tumor associated antigen, such that the RM bound LanM is directed to a tumor in the subject. Discussion and design of antibody-drug conjugates (ADCs) are prevalent, including suitable targeting moieties and linkers for attaching a targeting moiety to a drug (here, the RM bound LanM). See, e.g., U.S. Pat. Nos. 10,537,644; 10,442,860; 10,413,621.

In embodiments, the RM pharmaceutical composition can further comprise non-RMs and/or contact non-RMs when administered to a subject. For example, the subject likely has circulating Ca, Fe, Cu, Mg, Zn, Mn, or the like, but the selectivity of the LanM for the RM is such that the RM will not be displaced by these other non-RMs in the subject. This RM-selectivity of the LanM can ensure the RM stays bound to the LanM and will circulate to the desired area within the subject for the desired end use (e.g., as a therapeutic or for imaging). Non-limiting examples of non-RMs that can be present in the RM pharmaceutical composition disclosed herein or in the subject include one or more of Li, Na, K, Mg, Ca, Sr, Rb, Cs, Ba, Al, Si, Mn, Fe, Co, Ni, Cu, Zn, Ti, Sn, and V. In some cases, the RM pharmaceutical composition or the subject comprises one or more of: Fe, Co, Cu, Ca, and Mg.

Many target elements described herein can be useful in pharmaceutical applications (e.g., imaging a tumor, treating cancer, etc.). The methods of the disclosure can advantageously provide improved purity of the TE by purification of the TE using LanM.

Pharmaceutical Composition with Purified TE

In embodiments, a method of preparing a target element (TE) pharmaceutical composition with a purified TE can include purifying the TE by contacting the TE or a source containing the TE and a lanmodulin protein (LanM) such that the TE binds to the lanmodulin to form TE-LanM, wherein the TE is one or more of a rare-earth element (REE), Bi, Tl, and In and the LanM protein comprises at least one LanM unit; recovering the TE-LanM to form a solution comprising the TE-LanM; adjusting the pH of the solution comprising the TE-LanM to less than 2.5, such that the TE desorbs from the LanM; isolating the desorbed TE; and admixing the desorbed TE and at least one pharmaceutically acceptable excipient to provide the TE pharmaceutical composition.

In embodiments, the TE pharmaceutical compositions as disclosed herein having purified TEs (not including a LanM) can include the TEs purified by the methods of preparing a target element pharmaceutical composition, and a pharmaceutically acceptable excipient.

In any of the foregoing embodiments, as used herein, the term "excipient" means any pharmaceutically acceptable additive, carrier, diluent, adjuvant, or other ingredient, other than the TE bound to the modified LanM, or the RM bound to the modified LanM. As used herein, the term "pharmaceutically acceptable" means that the referenced substance, such as a particular excipient, is safe and suitable for administration to a subject.

The compositions of the disclosure can be administered to a subject in a therapeutically effective amount. As used herein, the term "therapeutically effective amount" means an amount of a composition or combination of therapeutically active compounds that ameliorates, attenuates or eliminates one or more symptoms of a particular disease or disorder (e.g., macular edema), or prevents or delays the onset of one of more symptoms of a particular disease or disorder. As used herein, the term "subject" means animals, such as dogs, cats, cows, horses, and sheep (i.e., non-human animals) and humans. In embodiments, the subject is a mammal (e.g., human).

The compositions disclosed herein and other pharmaceutically active compounds, if desired, can be administered to a subject by any suitable route, e.g. orally, rectally, parenterally, (for example, intravenously, intramuscularly, or subcutaneously) intracisternally, intravaginally, intraperitoneally, intravesically, or as a buccal, inhalation, or nasal spray. The administration can be to provide a systemic effect (e.g. enteral or parenteral). All methods that can be used by those skilled in the art to administer a pharmaceutical composition are contemplated.

Compositions suitable for parenteral injection may comprise physiologically acceptable sterile aqueous or nonaqueous solutions, dispersions, suspensions, or emulsions, and sterile powders for reconstitution into sterile injectable solutions or dispersions. Examples of suitable aqueous and nonaqueous carriers, diluents, solvents, or vehicles include water, ethanol, polyols (propylene glycol, polyethylene glycol, glycerol, and the like), suitable mixtures thereof, vegetable oils (such as olive oil) and injectable organic esters such as ethyl oleate. Proper fluidity can be maintained, for example, by the use of a coating such as lecithin, by the maintenance of the required particle size in the case of dispersions, and by the use of surfactants.

Microorganism contamination can be prevented by adding various antibacterial and antifungal agents to a pharmaceutical composition as disclosed herein, for example, parabens, chlorobutanol, phenol, sorbic acid, and the like. It may also be desirable to include isotonic agents, for example, sugars, sodium chloride, and the like. Prolonged absorption of injectable pharmaceutical compositions can be brought about by the use of agents delaying absorption, for example, aluminum monostearate and gelatin.

Methods of Treating Cancer

In embodiments, provided herein are methods of treating cancer in a subject suffering therefrom, comprising administering a TE pharmaceutical composition including TE-LanM, to the subject. In embodiments, provided herein are methods of treating cancer in a subject suffering therefrom, comprising administering a TE pharmaceutical composition including a TE purified by the methods of preparing a target element pharmaceutical composition disclosed herein.

Also provided herein are methods of treating cancer in a subject suffering therefrom, comprising administering the RM pharmaceutical composition disclosed herein, to the subject.

As used herein, the terms "treat," "treating," "treatment," and the like refer to eliminating, reducing, or ameliorating a disease or condition, and/or symptoms associated therewith. Although not precluded, treating a disease or condition does not require that the disease, condition, or symptoms associated therewith be completely eliminated. As used herein, the terms "treat," "treating," "treatment," and the like may include "prophylactic treatment," which refers to reducing the probability of redeveloping a disease or condition, or of a recurrence of a previously-controlled disease or condition, in a subject who does not have, but is at risk of or is susceptible to, redeveloping a disease or condition or a recurrence of the disease or condition. The term "treat" and synonyms contemplate administering a therapeutically effective amount of a compound of the disclosure to an individual in need of such treatment. Within the meaning of the disclosure, "treatment" also includes relapse prophylaxis or phase prophylaxis, as well as the treatment of acute or chronic signs, symptoms and/or malfunctions. The treatment can be orientated symptomatically, for example, to suppress symptoms. It can be effected over a short period, be oriented over a medium term, or can be a long-term treatment, for example within the context of a maintenance therapy.

In embodiments, the cancer is liver cancer, skin cancer, bone metastases, brain cancer glioblastoma, lymphoma, colon cancer, prostate cancer, leukemia, or a combination thereof. In embodiments, the targeting moiety is specific for the cancer to be treated.

Methods of Imaging a Tumor

In embodiments, provided herein are methods of imaging a tumor in a subject, comprising administering the TE pharmaceutical composition including a TE-LanM, to the subject and performing an imaging modality on the subject. In embodiments, provided herein are methods of imaging a tumor in a subject, comprising administering the TE pharmaceutical composition including a TE pharmaceutical composition including a TE purified by the methods of preparing a target element pharmaceutical composition disclosed herein, to the subject and performing an imaging modality on the subject. In embodiments, the REE of the TE pharmaceutical composition used in the imaging methods comprises Gd, $^{44}$Sc, $^{47}$Sc, $^{90}$Y, $^{134}$Ce, $^{134}$La, $^{86}$Y, $^{149}$Tb, $^{152}$Tb, $^{155}$Tb, $^{161}$Tb, $^{153}$Sm, $^{169}$Yb, or a combination thereof.

In embodiments, the imaging modality is selected from the group consisting of magnetic resonance imaging (MRI), positron emission tomography (PET), positron emission tomography/computed tomography (PET/CT), positron emission tomography/magnetic resonance imaging (PET/MRI), and single-photon emission computerized tomography (SPECT).

Methods of Sequestering TE In Vivo

In some cases, pharmaceutical compositions of LanM and a pharmaceutically acceptable excipient are contemplated that are initially free of TE (i.e., no TE is present). Such compositions can be useful upon administration to a subject to selectively remove and/or sequester TEs from the subject in vivo, such as detoxification, removal of radionuclides following accidental internal contamination, or chelation therapy, without depleting the subject's essential nutrients, such as Mg, Ca, Fe, Zn, Cu, or the like. In embodiments, a method of sequestering and/or removing a target element from a subject in vivo comprising administering a lanmodulin protein (LanM), wherein upon administration and/or circulation in vivo, the LanM contacts the TE present in the subject such that the target element (TE) binds to the lanmodulin to form TE-LanM. As detailed above the TE can be one or more of a rare-earth element (REE), Bi, Tl, and In, and the LanM protein comprises at least one LanM unit; recovering the TE-LanM from the sample. In embodiments, following recovery of the TE-LanM. In embodiments, the TE-LanM can be cleared by the body through natural processes, thereby removing the TE from the subject. In any of the embodiments of this method of removing TE from a patient, the LanM can be a modified LanM having a targeting moiety as detailed above.

In embodiments, compositions of LanM and a pharmaceutically acceptable excipient are contemplated that are initially free of RM (i.e., no RM is present). Such compositions can be useful upon administration to a subject to selectively remove RMs from the subject's body, such as detoxification or chelation therapy, without depleting the subject's essential nutrients, such as Mg, Ca, Fe, Zn, Cu, or the like. In embodiments, a method of sequestering and/or removing a radiometal in a subject in vivo can include administering the pharmaceutical composition to the subject, wherein upon administration and/or circulation within the subject in vivo, the LanM contacts the RM present in vivo such that the radiometal binds to the lanmodulin to form RM-LanM, wherein the LanM protein comprises at least one LanM unit. In embodiments, the RM-LanM can be cleared by the body through natural processes, thereby removing the RM from the subject. In any of the embodiments of this method of removing RM from a patient, the LanM can be a modified LanM having a targeting moiety as detailed above.

EXAMPLES

Materials and Methods

Chemicals—All solutions were prepared using deionized water purified by a Millipore Milli-Q reverse osmosis cartridge system. REE chloride salts, analytical reagents and buffer reagents (>99.9%) were purchased from Millipore Sigma. VivaSpin® 500 and VivaSpin® 2 centrifugal concentrators (Molecular weight cut-off of 3,000 g/mol) were purchased from GE Healthcare. Am-243 stock solutions were obtained from the inventory of Lawrence Livermore National Laboratory. An aged Th-232 starting material (i.e. Th-232 containing also Ra-228, Ac-228, Ra-224) was obtained from the inventory of Lawrence Livermore National Laboratory. A carried-free stock solution of Sr-90 was purchased from Eckert and Ziegler (USA).

E-Waste solutions were provided by Idaho National Laboratory.

Non-combusted coal leachate solutions were provided by the University of North Dakota.

C-terminally His-tagged lanmodulin (12,500 kDa) was isolated and described in Cotruvo et al., *Biochemistry* 58 (2), 120-125 (2019).

Ultrafiltration procedures—Filtration experiments were performed using centrifugal concentrators (referred hereafter as "filters") with a molecular weight cut-off of 3,000 g/mol. Typically, the filters were first rinsed with Milli-Q water and then rinsed with the appropriate buffer by passing the maximum volume of solution (500 µL for VivaSpin® 500 and 2 mL for VivaSpin® 2) via centrifugation. No difference was observed between the two models of filters. After preparation of the samples and equilibration for 10 min, the samples were loaded in the filters and centrifuged for about 60 min at 12,000 rpm. Finally, the filtrates were recovered and analyzed by Arsenazo III titration or inductively coupled plasma (ICP-MS). For synthetic samples and E-waste samples, ICP-MS analyzes were performed at University of California Santa Cruz. In the case of lignite samples, ICP-MS analyses were performed at Duke University.

Industrial feedstock experiments—For a better comparison between industrial feedstocks and synthetic REE mixtures, experiments were performed with a total REE concentration of ~200 UM by diluting the feedstocks prior to adding LanM. Solutions were diluted in 25 mM glycine, 25 mM KCH₃COO buffer at pH 1.5 to 6. Tests were also conducted with undiluted solution for the non-combusted coal leachate feedstock and similar results were obtained. After addition of LanM, the samples were centrifugated (12,000 rpm) and passed through a 3 KDa molecular weight cut-off filter. The low-molecular weight fraction was recovered and analyzed by ICP-MS.

Radiometal separation experiments—Solutions containing LanM and radioactive isotopes (ex: Am-243 in equilibrium with its daughter Np-239; Th-232 and its decay products; Sr-90 in equilibrium with its daughter Y-90) were prepared in the desired buffer (examples of buffers include: HEPES/NaCl solutions at pH ~7, Acetate buffer at PH ~5, NaCl/Na2SO4/HEPES buffer at PH ~7, NaCl/MES buffer at pH ~6). The samples were injected into a size exclusion column (ex: Sephadex G25 PD-10 from Cytivia; PD Spin Trap from Cytivia; Econo Pac 10-DG from Bio-Rad) and then eluted by addition of buffer. The molecular weight cut-off of these systems was 5 kDa (manufacturer specifications). The elution was performed by gravity, at room temperature and ambient pressure. The typical sample volume was less than 1 mL and the total volume eluted through the column was ~10 mL. Fractions were collected, weighed for mass balance purposes, and the radioactivity in each fraction was determined by liquid scintillation counting and gamma spectroscopy. The nature of the isotope(s) present in each fraction after elution was determined based on the emission spectra and by evolution of the radioactivity over time (i.e., decay curves). Radioisotope separations were also performed using size exclusion filters (ex: Vivaspin 500 with a molecular weight cut-off of 3 kDa).

UV-vis-NIR spectrophotometric titrations—Absorbance spectra were measured using a high-performance Cary 6000i UV-vis-NIR spectrophotometer (Agilent Technologies). The path length was 10 mm. Spectra were blank corrected by measuring the absorbance of the corresponding buffer prior to each titration. The initial sample volume was 400 µL. Typically the initial sample contained 1 mM of REE in the desired buffer. Incremental additions of LanM were performed and at least 1 spectrum was recorded after each addition. The duration between each addition was at least 10 min even though it was noted that equilibrium was reached within less than 1 min. A minimum of ten points were collected and LanM was added up to 0.33 eq relative to the REE. One hour after the last addition of LanM, incremental additions of EDTA solution were performed and at least 1 spectrum was recorded after each addition. The added EDTA solution was pH-adjusted to the same pH value as the titration buffer prior to the titration. The exchange between LanM and EDTA was found to be fast (<1 min) but a conservative 10-15 min interval was left between EDTA additions. At least ten points were collected for each LanM-EDTA exchange titration. Spectra were also collected for solutions containing 1 mM of REE and 10 mM of EDTA in the titration buffer before each titration and were used in the data fitting to determine the formation constants of the REE-LanM complexes. All spectra were collected for dilution (due to reagent additions) and background absorbance.

Data fitting-Spectrophotometric titration datasets were imported into the refinement program HypSpec (Gans et al., *Talanta* 43, 1739-1753 (1996)) and analyzed by nonlinear least-squares refinement. All equilibrium constants were defined as cumulative formation constants, $\beta_{mlh}$, according to the following equations, where the metal and ligand were designated as M and L, respectively.

$$mM + hH + lL \rightleftharpoons [M_mH_hL_l] \qquad \text{Equation 1}$$

$$\beta_{mlh} = \frac{[M_mH_hL_l]}{[M]^m[H]^h[L]^l} \qquad \text{Equation 2}$$

In the frame of these studies, the metal was a REE and the ligand was either LanM or EDTA. For species that contained hydroxides, the h value was negative as required by the formalism of the HypSpec program. The chemical equilibria taken into account were as follows: autoprotolysis of water, EDTA protonation, ligand-metal complexation, and metal hydroxide formation. The metal hydroxide formation was included in the speciation model for consistency even though it had negligible effects on the refined $\beta_{mlh}$ values since the metals were fully complexed (by LanM or EDTA) under the experimental conditions herein. Known stability constants (i.e. metal hydroxide species, EDTA protonation, and metal-EDTA complexes) were taken from the peer-reviewed literature (Johnson, S. G. NIST46. NIST https://www.nist.gov/srd/nist46 (2013)) and fixed during the refinement processes. All stability constants were known except that of the REE-LanM complexes. The species that had absorbance significant enough to be observed and quantified by UV-vis-NIR spectrophotometry under experimental conditions herein were the REE-EDTA complexes and the REE-LanM complexes. The experimental setup and data treatment used in the present study was applied successfully to a wide range of metal/small-molecule systems (Deblonde et al., *Inorg. Chem.* 52, 8805-8811 (2013) and Pham et al., *J. Am. Chem. Soc.* 136, 9106-9115 (2014)) but it was extended here to metalloproteins. To comply with the usual formalism used in biology for protein binding, the equilibrium constant was reported in terms of averaged $K_d$ per site, as defined by the following equations (charges are omitted for clarity):

$$MLanM = M + LanM; K_d^{11} = \frac{1}{\beta_{11}} = \frac{[LanM][M]}{[MLanM]} \quad \text{Equation 3}$$

$$M_mLanM = M + M_{m-1}LanM; K_a^{m1} = \frac{[M_{m-1}LanM][M]}{[M_mLanM]} \quad \text{Equation 4}$$

$$\beta_{31} = \frac{1}{K_d^{11}K_d^{21}K_d^{31}} \quad \text{Equation 5}$$

$$-\log \beta_{31} = \log K_d^{11} + \log K_d^{21} + \log K_d^{31} = 3\log K_d^{average} \quad \text{Equation 6}$$

$$K_d^{average} = \frac{1}{\sqrt[3]{\beta_{31}}} \quad \text{Equation 7}$$

ICP-Mass spectrometry analysis-Samples were analyzed by ICP-MS at the University of California Santa Cruz and Duke University. Samples were diluted in % 5 $HNO_3$ prior to analysis. $^{103}Rh$ was used as an internal standard. The following isotopes were used: $^{24}Mg$, $^{27}Al$, $^{28}Si$, $^{4}Ca$, $^{45}Sc$, $^{5}Mn$, $^{56}Fe$, $^{59}Co$, $^{60}Ni$, $^{63}Cu$, $^{66}Zn$, $^{8}Sr$, $^{89}Y$, $^{139}La$, $^{140}Ce$, $^{141}Pr$, $^{146}Nd$, $^{147}Sm$, $^{153}Eu$, $^{157}Gd$, $^{159}Tb$, $^{163}Dy$, $^{165}Ho$, $^{166}Er$, $^{169}Tm$, $^{172}Yb$, $^{175}Lu$, $^{238}U$.

Dynamic light scattering (DLS)-DLS measurements were performed using Zetasizer Nano ZS instrument (Malvern Instruments) in backscatter detection mode. Samples were prepared in 10 mM glycine, 10 mM acetate buffer. Samples were filtered at 0.2 µm prior to measurement. LanM concentration was ~100 UM (1.2 mg/mL). At least 8 acquisitions were performed for each data point. The hydrodynamic diameters reported in this study were calculated based on the volume distribution using the zetasizer explorer software (Malvern).

Liquid scintillation counting (LSC)—The radioactivity of the RM-containing samples was measured using a TRI-CARB 4910TR Liquid Scintillation counting instrument (PerkinElmer) equipped with an alpha/beta discriminator. Samples were diluted in a scintillation cocktail (Ultima Gold™) prior to counting. The LSC instrument was calibrated daily. The measured activities were background corrected. Radioisotope decay curves were determined by repeated LSC measurements over an extended period of time (typically corresponding to at least 10 half-lives of the studied isotope).

Example 1—Solution Thermodynamics of the LanM-REE Systems

The binding of trivalent REE ions to LanM was investigated under mild acidic conditions and by directly monitoring the 4f-4f absorbance bands of the selected lanthanide ions using UV-visible-near-infrared spectrophotometry. Indeed, typical REE-protein systems are constrained by the low availability of the macromolecule, the low solubility of the REE-protein species, as well as the low extinction coefficients of the REE absorbance bands (<20 $M \cdot cm^{-1}$) which prevent spectrophotometric investigations. Unlike most proteins, the combined ease of synthesis, high solubility of its REE complexes and the presence of multiple binding sites which inherently decreases the protein consumption, were taken advantage of to carry out the experiments herein.

Upon addition of LanM to solutions of $Pr^{3+}$, $Nd^{3+}$, $Sm^{3+}$, $Dy^{3+}$, $Ho^{3+}$, $Er^{3+}$, or $Tm^{3+}$, significant changes in the absorbance spectra were observed (FIG. 1 and Table 2). Since absorbance spectrophotometry probes the coordination sphere of the metal center in contrast to the commonly used protein conformational change or protein fluorescence signals, these spectral perturbations are direct evidence of metal-protein binding. The absorbance bands of the LanM-bound REEs were red shifted compared to the free ions by several nanometers indicating a strong stabilization of the $Ln^{3+}$ ions by the protein (Table 1). A general broadening of the absorbance bands was also observed which corroborates the presence of multiple metal centers with similar coordination environment and lower symmetry compared to the free ions. This is supported by the solution state NMR structure determined for the $Y^{3+}$-LanM system at neutral pH where three metal binding sites were observed.

The formation constants corresponding to the three tight binding sites of LanM (REE₃-LanM) were determined under mild acidic conditions relevant to industrial REE extraction processes (pH 5). The REE-EDTA complexes have spectral signatures sufficiently distinct from their LanM counterparts to accurately monitor the ligand-exchange reaction, as exemplified for the $Nd^{3+}$-LanM-EDTA system on FIG. 1. Excess EDTA (5-10 eq relative to LanM) was found necessary to completely displace the $Ln^{3+}$ ions from the protein highlighting its strong affinity for the REEs.

The kinetics of the ligand-exchange reactions were fast (second to minute scale), allowing the systematic investigation of the REE-LanM systems observable by UV-vis-NIR spectrophotometry i.e. with trivalent Pr, Nd, Sm, Dy, Ho, Er, and Tm. Using the previously established stability constants of the REE-EDTA species as a reference (Johnson et al., NIST46. NIST https://www.nist.gov/srd/nist46 (2013)), refinement of the spectrophotometric data revealed that LanM forms extremely stable complexes across the REE series with global formation constants β31 between $10^{+32}$ and $10^{+37}$ which corresponds to an averaged $K_d$ of 0.5 to 25 pM (when considering 3 equivalent metal binding sites).

Table 1 shows a comparison of LanM to other metalloproteins previously studied for REE complexation, namely calmodulin (CaM), cadherin (Cad), S100β, ferritin (Ft), transferrin (Tf), and siderocalin (Scn), as well as synthetic lanthanide-binding peptides (LBT and dLBT). The strongest REE-binding macromolecules reported before LanM were mutants of human lipocalin 2 (Lcn2) that have been obtained by random mutagenesis to recognize a synthetic REE-DTPA derivative with a $K_d$ of 400 to 90,000 µM (Kim et al., *J. Am. Chem. Soc.* 131, 3565-3576 (2009)). Further, one of the binding sites in dLBT, which exhibited a $K_d$ of 2,500 µM for $Tb^{3+}$ (Martin et al., *J. Am. Chem. Soc.* 129, 7106-7113 (2007)). As shown in Table 1, the affinity of LanM towards REEs was orders of magnitude higher than any lanthanide-binding macromolecule reported to date.

Moreover, mammalian proteins like Tf, Son and CaM exhibited affinity toward the REEs far lower than for the elements they are meant to transport in nature ($Fe^{3+}$, $Ca^{2+}$, $Cu^{2+}$ . . . ) which would translate to very poor efficiency and selectivity for technologies aiming at REEs. On the other hand, LanM is REE-specific and its relative binding affinity REE/non-REE was about $10^{+8}$ and $10^{+15}$ times higher than that of CaM and Tf, respectively (Table 1). It should also be noted that Tf, Lcn2, and Son are unable to bind directly to the metal ions and require a co-chelator (also known as "synergistic anion"). For example, Tf only complexed with metal ions in the presence of excess bicarbonate, citrate, oxalate, or nitrilotriacetate whereas Son only bound cations that were already complexed to bacterial siderophore ligands such as enterobactin, catechols and hydroxamates which drastically restricted their potential use outside laboratory conditions. The binding mode of LanM is straightforward and therefore more suitable for applications as it doesn't depend on the presence of another specific chelator.

Table 1 shows a comparison of metalloprotein affinities for REEs. Formation constants ($\log \beta_{ML}$) and dissociation constants ($K_d$) determined for various REE-LanM complexes and comparison with other known REE-binding natural proteins, calmodulin (CaM), S100β, ferritin (Ft), transferrin (Tf), siderocalin (Scn), and synthetic lipocalin mutants (Lcn2) and lanthanide-binding peptides (LBT and dLBT, also known as lanthanide-binding tag). Binding constants for non-REE ions and corresponding REE selectivity were also given for comparison.

TABLE 1

| Macromolecular system | $\log \beta_{ML}$ | $K_d$ | REE selectivity | |
|---|---|---|---|---|
| Lanmodulin | | | $K_d\ Ca^{2+}/K_d\ REE^{3+}$ | |
| 3 $Pr^{3+}$ + LanM = $Pr_3$LanM | 32.9 ± 0.1[a] | 10.6 pM | 6.7*10[+7] | |
| 3 $Nd^{3+}$ + LanM = $Nd_3$LanM | 32.0 ± 0.1[a] | 22.2 pM | 3.2*10[+7] | |
| 3 $Sm^{3+}$ + LanM = $Sm_3$LanM | 31.9 ± 0.3[a] | 24.2 pM | 2.9*10[+7] | |
| 3 $Dy^{3+}$ + LanM = $Dy_3$LanM | 32.5 ± 0.3[a] | 14.9 pM | 4.8*10[+7] | |
| 3 $Ho^{3+}$ + LanM = $Ho_3$LanM | 33.2 ± 0.2[a] | 8.58 pM | 8.3*10[+7] | |
| 3 $Er^{3+}$ + LanM = $Er_3$LanM | 35.6 ± 0.2[a] | 1.39 pM | 5.1*10[+8] | |
| 3 $Tm^{3+}$ + LanM = $Tm_3$LanM | 37.2 ± 0.4[a] | 0.41 pM | 1.7*10[+9] | |
| 3 $Ca^{2+}$ + LanM = $Ca_3$LanM | 9.4 | 710 μM[a'] | | |
| Calmodulin | | | $K_d\ Ca^{2+}/K_d\ REE^{3+}$ | |
| $La^{3+}$ + CaM = LaCaM | 4.9 | 12 μM[b] | 0.03-2.8 | |
| 2 $La^{3+}$ + CaM = $La_2$CaM | 9.4 | 32 μM[b] | 0.01-7.7 | |
| 3 $La^{3+}$ + CaM = $La_3$CaM | 13.8 | 40 μM[b] | 0.04-4.6 | |
| 4 $La^{3+}$ + CaM = $La_4$CaM | 17.7 | 120 μM[b] | 0.07-6.8 | |
| $Tb^{3+}$ + CaM = TbCaM | 5.3 | 5 μM[b] | 0.07-6.8 | |
| 2 $Tb^{3+}$ + CaM = $Tb_2$CaM | 9.9 | 25 μM[b] | 0.02-9.8 | |
| 3 $Tb^{3+}$ + CaM = $Tb_3$CaM | 14.6 | 20 μM[b] | 0.08-9.25 | |
| 4 $Tb^{3+}$ + CaM = $Tb_4$CaM | 18.7 | 72 μM[b] | 0.1-11.3 | |
| $Ca^{2+}$ + CaM = CaCaM | 4.5 | 34 μM[b'] | | |
| | 6.4 | 0.37 μM[b"] | | |
| 2 $Ca^{2+}$ + CaM = $Ca_2$CaM | 8.1 | 245 μM[b'] | | |
| | 12.8 | 0.46 μM[b"] | | |
| 3 $Ca^{2+}$ + CaM = $Ca_3$CaM | 11.8 | 185 μM[b'] | | |
| | 18.6 | 1.6 μM[b"] | | |
| 4 $Ca^{2+}$ + CaM = $Ca_4$CaM | 14.9 | 814 μM[b'] | | |
| | 23.6 | 8.5 μM[b"] | | |
| S100β | | | | |
| $Eu^{3+}$ + S100β = EuS100β | 6.2[c] | 660 ± 20 nM | | |
| Cadherin | | | | |
| $Tb^{3+}$ + Cad = TbCad | 3.8[d] | 143 μM | | |
| Ferritin | | | | |
| $Tb^{3+}$ + Ft = TbFt | 3.2-5.7[e] | 2-666 μM | | |
| Transferrin | | | $K_d\ Fe^{3+}/K_d\ REE^{3+}$ | $K_d\ Cu^{2+}/K_d\ REE^{3+}$ |
| $Nd^{3+}$ + Tf = NdTf | 6.09[f] | 813 nM | 2.6*10[−15] | 6.2*10[−7] |
| 2 $Nd^{3+}$ + Tf = $Nd_2$Tf | 11.13[f] | 9,120 nM | 4.6*10[−15] | 8.7*10[−7] |
| $Sm^{3+}$ + Tf = SmTf | 7.13[f] | 74 nM | 2.8*10[−14] | 6.8*10[−6] |
| 2 $Sm^{3+}$ + Tf = $Sm_2$Tf | 12.52[f] | 4,074 nM | 1.0*10[−14] | 1.9*10[−6] |
| $Gd^{3+}$ + Tf = GdTf | 7.96[f] | 11 nM | 1.9*10[−13] | 4.6*10[−5] |
| 2 $Gd^{3+}$ + Tf = $Gd_2$Tf | 13.9[f] | 1,148 nM | 3.7*10[−14] | 6.9*10[−6] |
| $Yb^{3+}$ + Tf = YbTf | 5.4[g] | 4,170 nM | 5.0*10[−16] | 1.2*10[−7] |
| 2 $Yb^{3+}$ + Tf = $Yb_2$Tf | 10.1[g] | 18,500 nM | 2.3*10[−15] | 4.3*10[−7] |
| $Fe^{3+}$ + Tf = FeTf | 20.7[h] | 2.1*10[−21] M | | |
| 2 $Fe^{3+}$ + Tf = $Fe_2$Tf | 40.1[h] | 4.2*10[−20] M | | |
| $Cu^{2+}$ + Tf = CuTf | 12.3[i] | 0.50 pM | | |
| 2 $Cu^{2+}$ + Tf = $Cu_2$Tf | 23.4[i] | 7.9 pM | | |
| $Zn^{2+}$ + Tf = ZnTf | 5.7[i] | 2.0 μM | | |
| 2 $Zn^{2+}$ + Tf = $Zn_2$Tf | 10.0[i] | 50 μM | | |
| Siderocalin | | | $K_d\ Fe^{3+}/K_d\ REE^{3+}$ | |
| $[Sm(Ent)]^{3-}$ + Scn = [Sm(Ent)]Scn | 8.2[j] | 7 nM | 0.06 | |
| $[Eu(Ent)]^{3-}$ + Scn = [Eu(Ent)]Scn | 8.1[j] | 8 nM | 0.02 | |
| $[Gd(Ent)]^{3-}$ + Scn = [Gd(Ent)]Scn | 8.3[j] | 5 nM | 0.08 | |
| $[Fe(Ent)]^{3-}$ + Scn = [Fe(Ent)]Scn | 9.4[j] | 0.4 nM | | |

TABLE 1-continued

| Macromolecular system | $\log \beta_{ML}$ | $K_d$ | REE selectivity |
|---|---|---|---|
| Lipocalin 2 mutants | | | |
| $[Y(DTPA)]^{x-}$ + Lcn2 = [Y(DTPA)]Lcn2 | $7.0\text{-}9.4^k$ | 0.4-90 nM | |
| LBT peptide | | | |
| $La^{3+}$ + LBT = LaLBT | $5.5^l$ | 3500 nM | |
| $Ce^{3+}$ + LBT = CeLBT | $6.0^l$ | 950 nM | |
| $Nd^{3+}$ + LBT = NdLBT | $6.6^l$ | 270 nM | |
| $Eu^{3+}$ + LBT = EuLBT | $7.2^l$ | 62 nM | |
| $Gd^{3+}$ + LBT = GdLBT | $7.1^l$ | 84 nM | |
| $Tb^{3+}$ + LBT = TbLBT | $7.2^l$ | 57 nM | |
| $Dy^{3+}$ + LBT = DyLBT | $7.1^l$ | 71 nM | |
| $Er^{3+}$ + LBT = ErLBT | $7.1^l$ | 78 nM | |
| $Yb^{3+}$ + LBT = YbLBT | $7.0^l$ | 100 nM | |
| $Lu^{3+}$ + LBT = LuLBT | $6.9^l$ | 128 nM | |
| Double LBT peptide | | | |
| $Tb^{3+}$ + dLBT = TbdLBT | $8.0\text{-}8.6^m$ | 2.5-10 nM | |
| $2 Tb^{3+}$ + dLBT = Tb$_2$dLBT | $15.5\text{-}16.2^m$ | 23-62 nM | |

[a]pH 5.0, 0.1M KCl/KCH$_3$COO buffer, 25° C. (This work).
[a']pH 7.2 (Cotruvo et al., *J. Am. Chem. Soc.* 140, 15056-15061 (2018)).
[b]pH 6.8, 20 mM PIPES, 10 mM KCl and
[b']pH 7.4, 10 mM TRIS, 10 mM KCl (Ye et al, *J. Am. Chem. Soc.* 127, 3743-3750 (2005)).
[b"]pH 7.55, 10 mM HEPES, 20 mM KCl (Haiech et al., *Biochemistry* 20, 3890-3897 (1981)).
[c]pH 7.0, 50 mM HEPES buffer. S100β is a calcium-binding protein similar to CanM (Chaudhuri, et al., *Biochemistry* 36, 9674-9680 (1997))
[d]Number of binding sites unknown. pH 7.4m 10 mM Tris, 100 mM KCl, 120 mM NaCl (Brayshaw et al., *Metallomics* 11, 914-924 (2019)).
[e]pH 6.5, 25° C. (Calisti, L. et al. PLOS ONE 13, e0201859 (2018)).
[f]pH 7.4 in the presence of 0.2 mM of synergistic bicarbonate, 0.1M HEPES buffer, 25° C. (Harris et al., *Inorg. Chem.* 25, 2041-2045 (1986) and Harris et al., *Inorg. Chem.* 31, 5001-5006 (1992)).
[g]pH 7.4 in the presence of 5 mM of synergistic bicarbonate, 0.1M HEPES buffer, 25° C. (Du et al., *European Journal of Biochemistry* 269, 6082-6090 (2002)).
[h]pH 7.4 and atmospheric pCO$_2$, 25° C. (Aisen et al., *J. Biol. Chem.* 253, 1930-1937 (1978)).
[i]15 mM HCO$_3^-$ (Sun et al., *Chem. Rev.* 99, 2817-2842 (1999)).
[j]pH 7.4, HEPES buffer (Allred et al., *PNAS* 112, 10342-10347 (2015)). Ent = Enterobactin.
[k]pH 8.8, 100 mM Tris, 100 mM NaCl, 5 mM MgCl2. DTPA = Me•DTPA-RNase-DIG conjugate (Kim et al., *J. Am. Chem. Soc.* 131, 3565-3576 (2009)).
[l]pH 7, 10 mM HEPES + 100 mM NaCl. Nitz et al., *Angewandte Chemie International Edition* 43, 3682-3685 (2004).
[m]pH 7.0, 0.1M NaCl, 10 mM HEPES (Martin et al., *J. Am. Chem. Soc.* 129, 7106-7113 (2007)).

Table 2 shows the wavelength of maximum absorbance of the REE-LanM species compared to the unbound REE ions, wherein M (III) is the unbound metal in the 3+ oxidation state and M$_4$LANM is the metal bound to LanM. Buffer: 25 mM KCH$_3$COO and 75 mM KCl at pH 5.

TABLE 2

| REE | M(III) in buffer | M4LanM |
|---|---|---|
| Pr(III) | 444.3 | 444.5 |
| | 468.5 | 470.3 |
| | 481.8 | 483.5 |
| | 589.0 | 592.5 |
| Nd(III) | 511.6 | 511.8 |
| | 521.8 | 525.0 |
| | 576.4 | 581.8 |
| | 740.8 | 744.4 |
| | 794.6 | 800.8 |
| | 865.2 | 872.2 |
| Sm(III) | 374.3 | 375.3 |
| | 402.0 | 403.0 |
| Dy(III) | 757.0 | 754.3 |
| | 807.0 | 803.8 |
| Ho(III) | 361.2 | 360.8 |
| | 416.6 | 417.0 |
| | 450.6 | 450.6 |
| | 485.0 | 485.0 |
| | 537.2 | 537.2 |
| | 641.2 | 644.2 |
| Er(III) | 364.4 | 364.4 |
| | 378.8 | 378.0 |
| | 487.0 | 487.6 |
| | 522.4 | 520.6 |
| | 652.4 | 652.4 |

TABLE 2-continued

| REE | M(III) in buffer | M4LanM |
|---|---|---|
| Tm(III) | 661.2 | 660.4 |
| | 683.8 | 686.0 |
| | 779.4 | 793.0 |

Example 2—Selectivity Across the REE Series

Figure 1A:
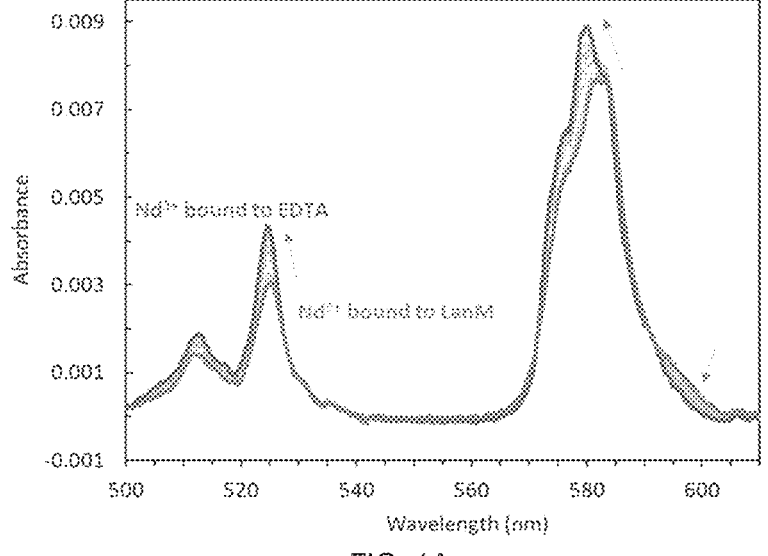
FIG. 1A-FIG. 1D shows an example of a competition titration between LanM and EDTA for the binding to $Nd^{3+}$ followed by UV-vis-NIR spectrophotometry. [Nd]=1 mM. [LanM]=0.31 mM. [EDTA]=0 to 4.1 mM. pH=5.0 (25 mM $KCH_3COO$, 75 mM KCl). The lower curve corresponds to the initial sample (no EDTA) and the upper corresponds to the final sample (excess of EDTA). Arrows indicate the main spectral changes.
Figure 1B:
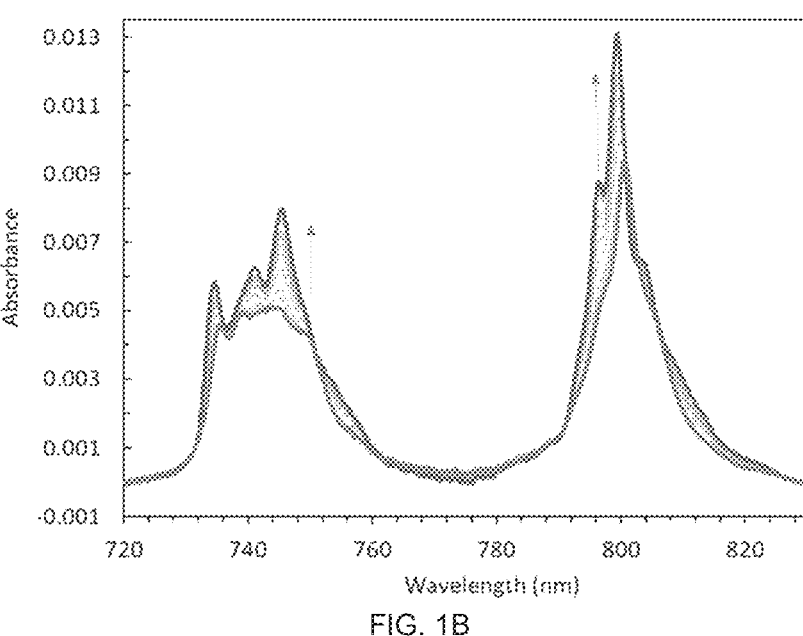
Figure 1C:
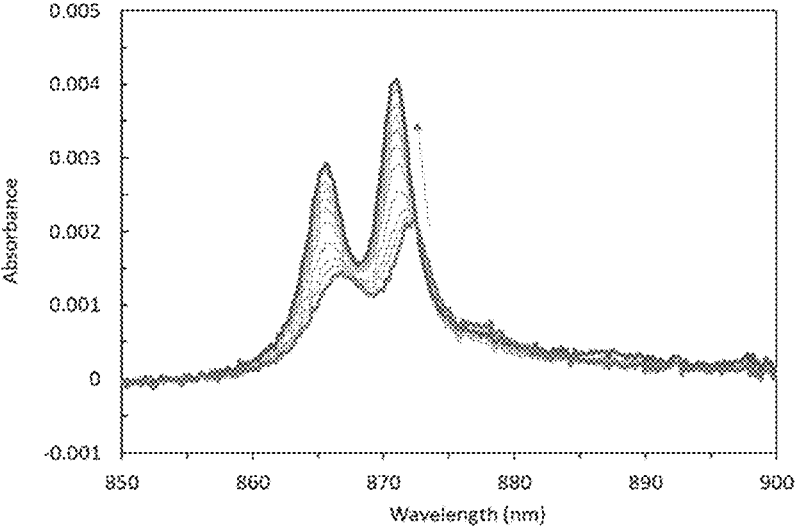
Figure 1D:
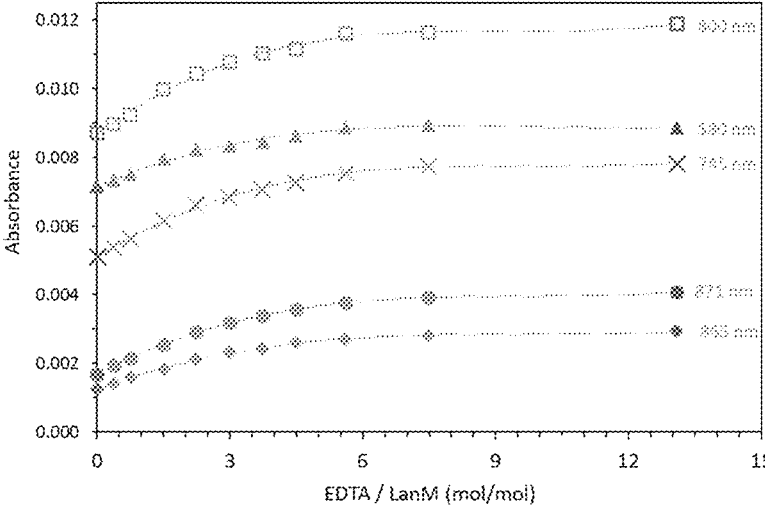
Figure 2A:
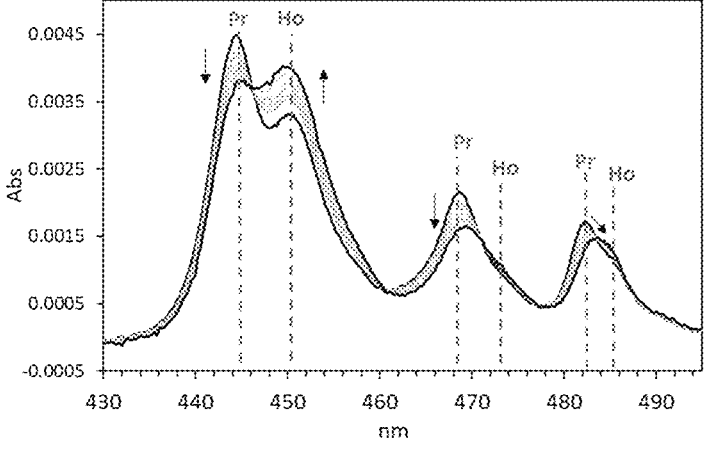
FIG. 2A-FIG. 2D shows the simultaneous uptake of light and heavy REEs by LanM. Spectral changes upon addition of LanM to solutions containing simultaneously light REE ($Pr^{3+}$) and heavy REEs ($Ho^{3+}$ or $Er^{3+}$). [Pr]=[Ho]=[Er]=0.5 mM. [LanM]=0 to 0.15 mM. The contribution of individual REE were determined based on reference spectra of pure $REE^{3+}$ and REE-LanM samples.
Figure 2B:
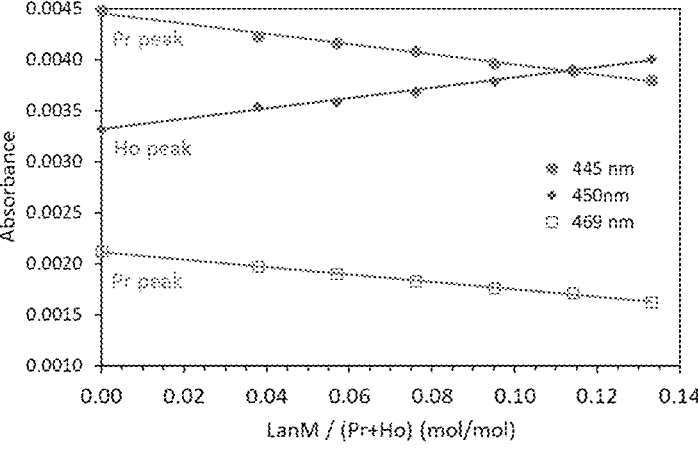
Figure 2C:
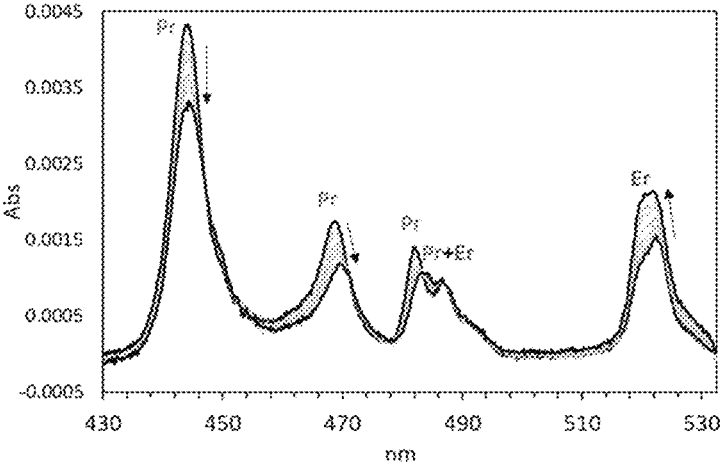
Figure 2D:
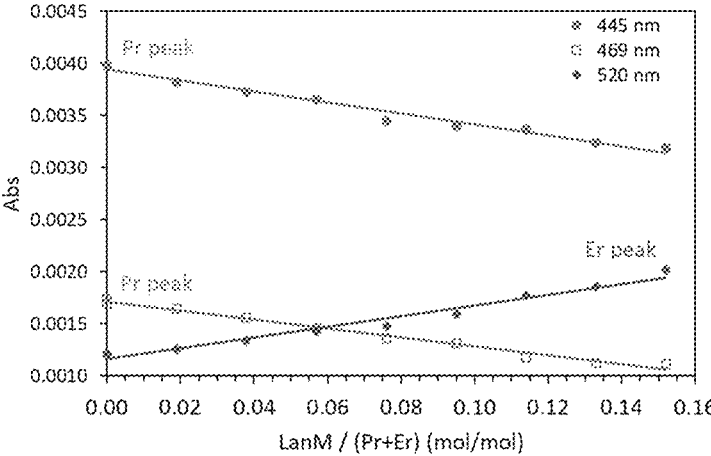
Figure 3A:
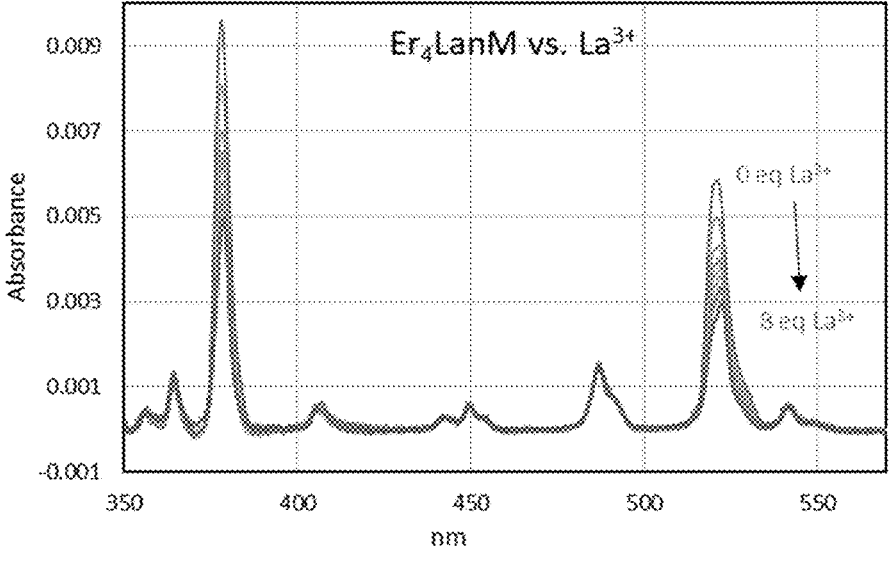
FIG. 3A-FIG. 3B shows the REE-REE substitution within the LanM system, e.g., $Er_4LanM$ exchanged with $La^{3+}$ and $Er_4LanM$ exchanged with $Yb^{3+}$. pH=5.0 (25 mM $KCH_3COO$, 75 mM KCl). [Er]=1 mM. [LanM]=0.25 mM. [La]=0 to 7.70 mM. [Er]=0 to 6.75 mM. Spectra are corrected for dilution.
Figure 3B:
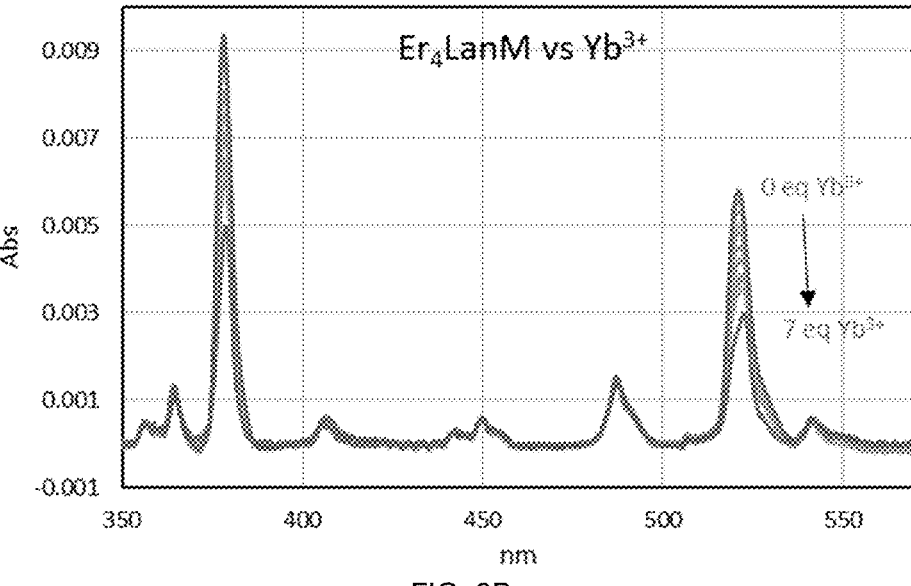
Figure 4:
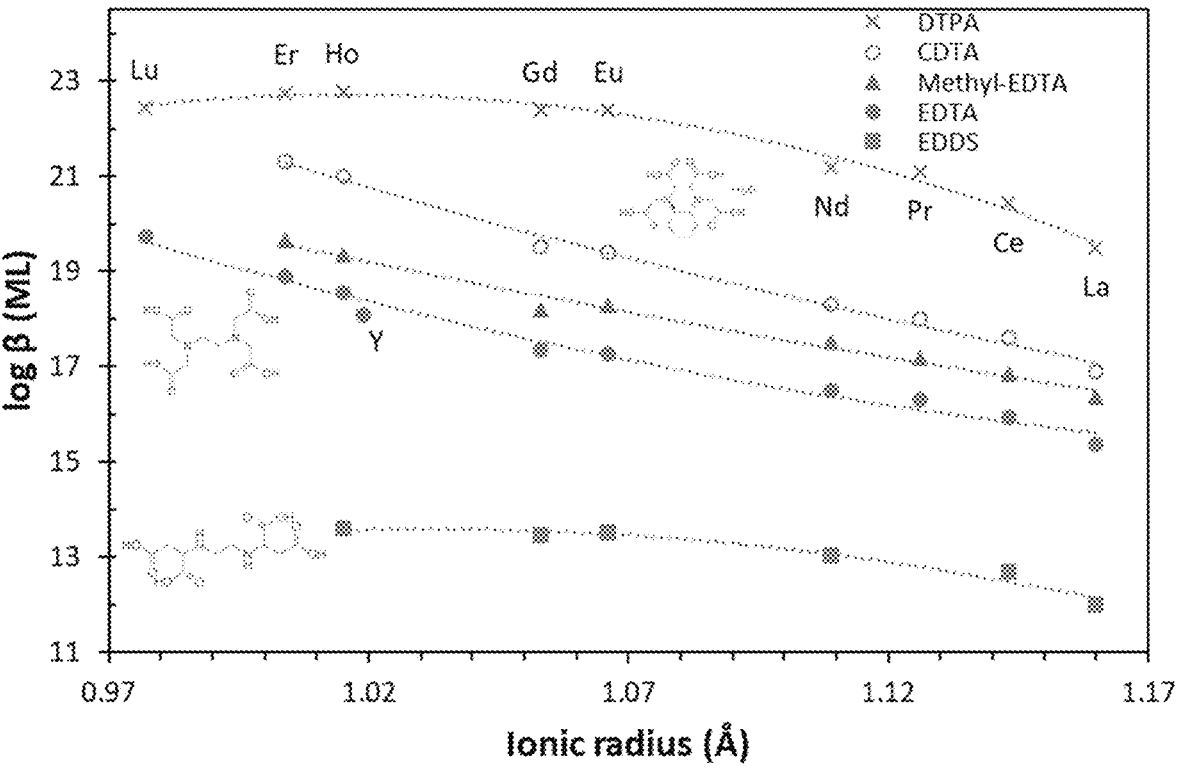
FIG. 4 shows stability constants (log (11) reported for common $REE^{3+}$-chelator complexes. Log $\beta_{11}$ taken from the NIST Critical database. DTPA=diethylenetriaminepentaacetic acid. EDTA=ethylenediaminetetraacetic acid. CDTA=(1,2-Cyclohexylenedinitrilo)tetraacetic acid. Methyl-EDTA=1,2-Diaminopropane-N, N,N',N'-tetraacetic Acid. EDDS=Ethylenediamine-N, N'-disuccinic acid.
Figure 5A:
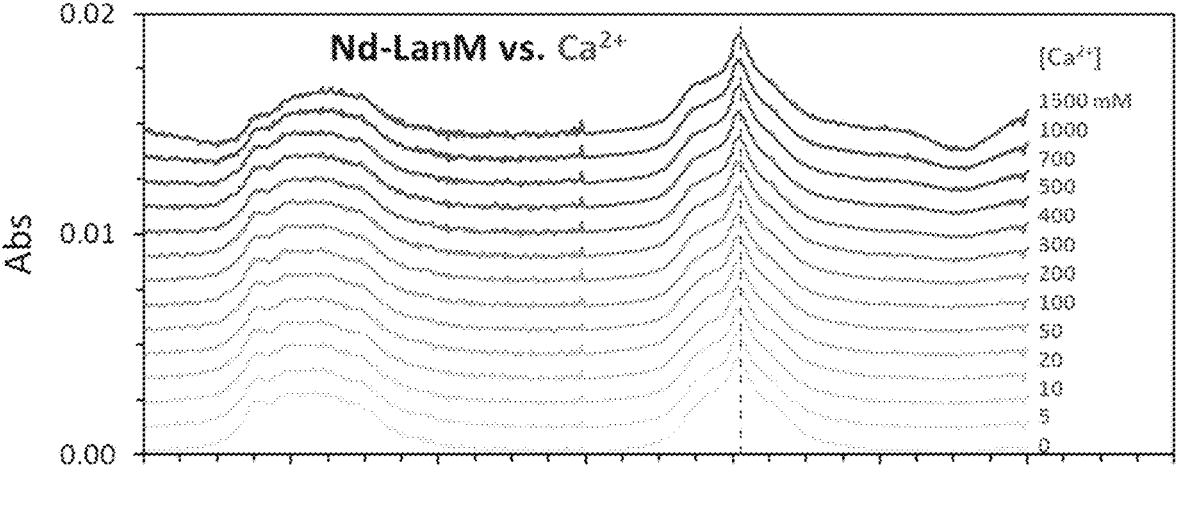
FIG. 5A-FIG. 5H shows the robustness of REE-LanM complexes in Mg-, Ca-, Zn-, and Cu-rich solutions. The figures show a competitive assay between $Nd^{3+}$-LanM and $Mg^{2+}$, $Ca^{2+}$, $Cu^{2+}$, or $Zn^{2+}$. [Nd]=0.500 mM, [LanM]=0.125 mM. Competitor: $MgCl_2$, $CaCl_2$), $ZnSO_4$, or $CuCl_2$. [Mg]=0 to 1500 mM. [Ca]=0 to 1500 mM. [Zn]=0 to 400 mM. [Cu]=0 to 10 mM. Evolution at the most sensitive wavelengths are given on the right panels. Buffer: 25 mM glycine, 25 mM $KCH_3COO$, 50 mM KCl, pH 5. Dotted curves: reference sample containing 0.500 mM $NdCl_3$ in the same buffer.
Figure 5B:
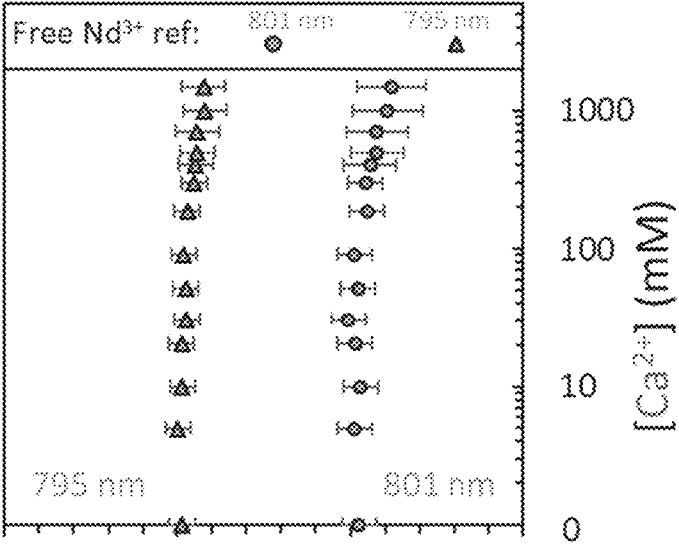
Figures 5C, 5D:
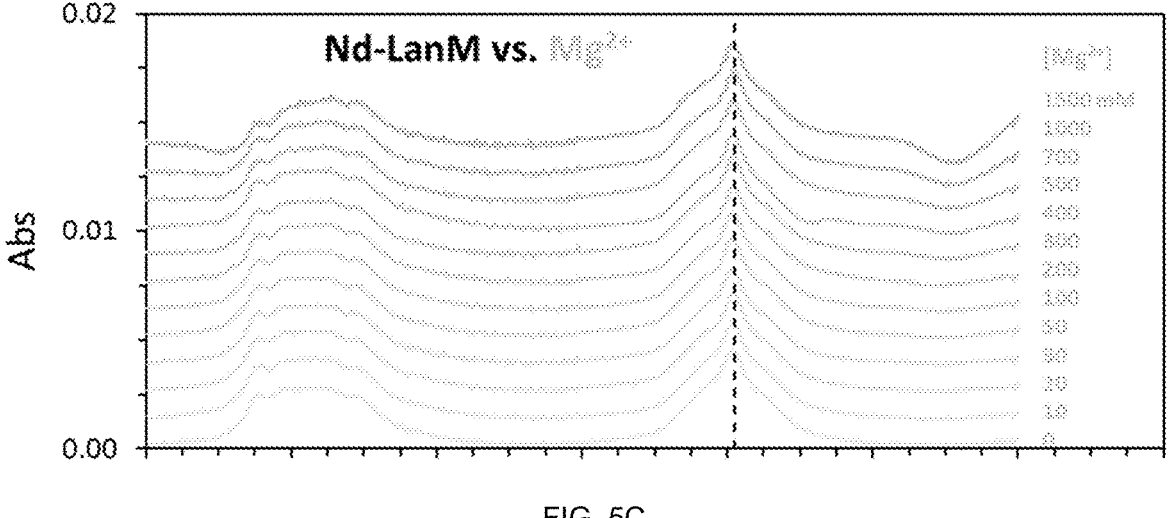
Figure 5E:
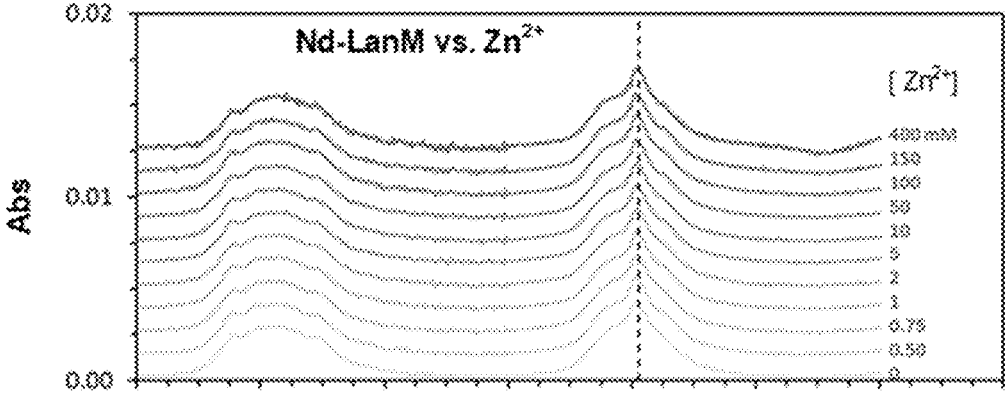
Figure 5F:
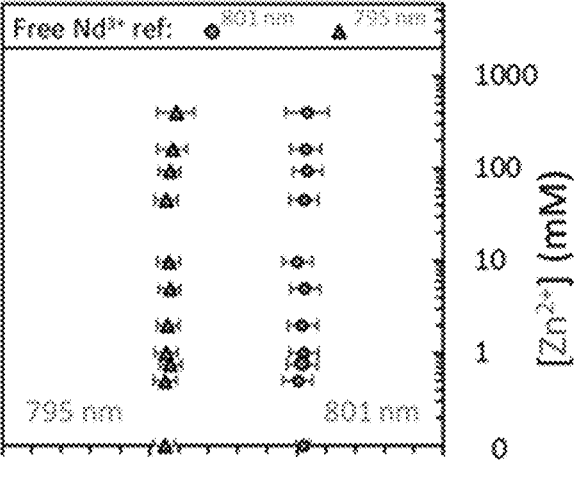
Figure 5G:
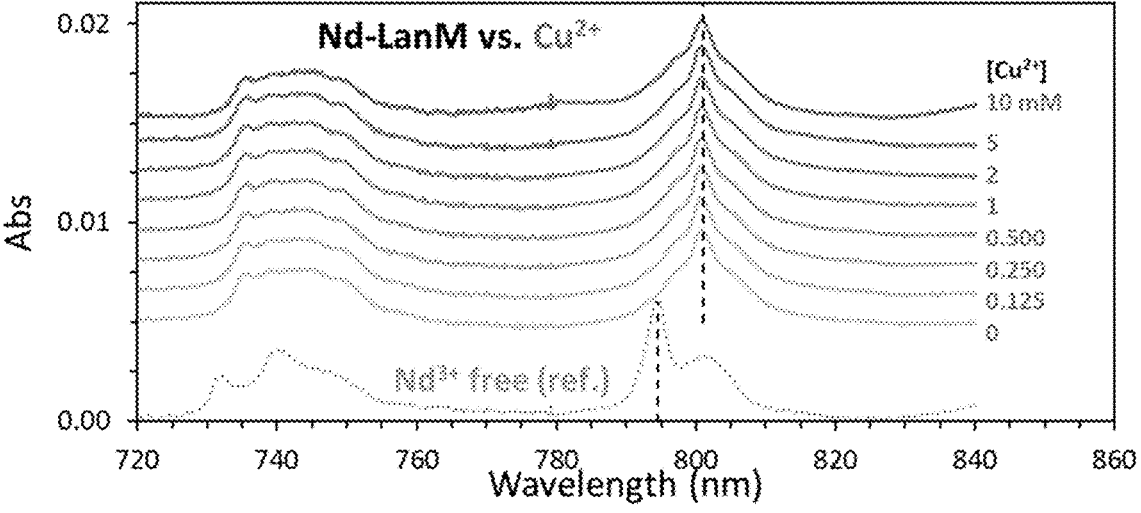
Figure 5H:
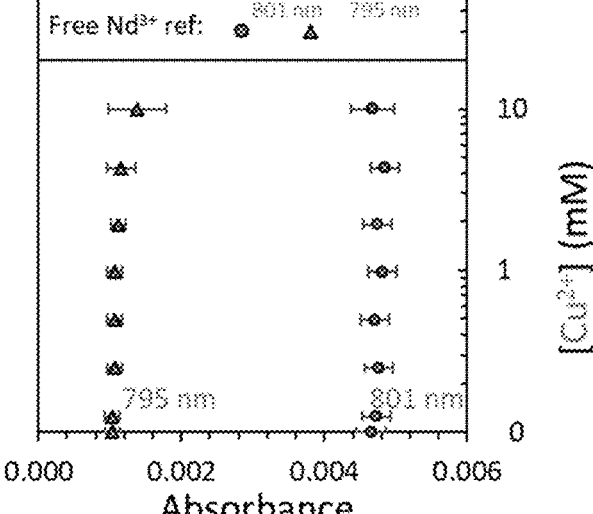

Given the presence of multiple binding sites and the relatively small differences in $K_d$ observed across the REE-LanM series (Table 1), experiments with mixtures of heavy and light REEs (ex: $Pr^{3+}$ and $Ho^{3+}$ or $Pr^{3+}$ and $Er^{3+}$) showed that LanM can scavenge multiple REEs concomitantly. As displayed in FIG. 2, addition of LanM to solutions containing equimolar amounts of REE mixtures triggered the simultaneous uptake of LREE and HREE ions. REE-REE substitutions assays also demonstrated LanM's ability to exchange one REE for another even when it was in its metal-bound conformation (FIG. 3). These results are in line with the presence of multiple binding sites and with the relatively small differences in $K_d$ observed across the REE-LanM series (Table 1). The trend observed across the REE-LanM series departed from previously reported REE chelators such as LBTs and some polyaminocarboxylates like EDTA, EDDS, and DTPA (FIG. 4). These previously developed synthetic molecules exhibited a continuous increase in affinity going from $La^{3+}$ to $Lu^{3+}$ whereas the trend for LanM appears unique and non-monotonic.

Surprisingly, the REE binding mode of LanM was relatively common with four to five carboxylate groups coming from aspartate and glutamate residues and one backbone carbonyl, reminiscent of LBTs and polyaminocarboxylate ligands. This suggests that other effects, beyond the local coordination environment of the metal ions and specific to protein chemistry (e.g., hydrophobic packing interactions within the protein), drove the selectivity of LanM toward REE ions. Such an unusual selectivity can be leveraged to perform grouped but selective recovery of the REEs against the non-REE impurities (vide infra).

Example 3—Competition Against Non-REE Impurities

Formation of mixed metal species was previously observed for ligands that comprise multiple binding sites and it usually prevented their use for purification applications due to competition between the targeted metals and impurities which led to low recovery or low purity. For example, Tf accommodated readily distinct metals in its two binding pockets such as $Fe^{3+}$ and $Pu^{4+}$, $Fe^{3+}$ and $Ln^{3+}$, or $Fe^{3+}$ and $Cm^{3+}$. Moreover, non-REE elements generally outcompeted REEs in metalloproteins.

Herein, REE/non-REE substitutions were attempted with $Nd^{3+}$-LanM and using $Mg^{2+}$, $Ca^{2+}$, $Zn^{2+}$, or $Cu^{2+}$ as challengers. These competing elements were selected because they are present at high concentrations relative to the REEs in environmental media as well as industrial feedstocks. The ionic radius of $Ca^{2+}$ (1 Å) is also close to that of the $Ln^{3+}$ ions and it is generally a strong competitor. Samples containing 0.125 mM of $Nd_4LanM$ were challenged by direct additions of concentrated $MgCl_{2(aq)}$, $CaCl_{2(aq)}$, $ZnSO_{4(aq)}$, or $CuCl_{2(aq)}$. As seen in FIG. 5, LanM retained its REE ions even in solutions containing at least up to 1.5 M $Mg^{2+}$, 1.5 M $Ca^{2+}$, 0.4 M $Zn^{2+}$, or 10 mM $Cu^{2+}$ (due to the intense blue color of $Cu^{2+}$, higher concentrations couldn't be tested). These concentrations exceeded the impurity levels found in typical REE feedstocks. The performance of LanM in the presence of macroscopic amounts of impurities is unmatched to date by any other protein (Table 1).

For comparison, similar experiments were also performed with the synthetic chelator EDTA. Contrasting with the robustness and selectivity of LanM, EDTA released its REE ions in the presence of ~2 equivalents of $Zn^{2+}$ or $Cu^{2+}$. These results highlighted the lack of selectivity of commonly used REE-binding small chelators and the need for developing more selective and robust REE scavengers. This issue currently represents a major challenge in the pharmaceutical community as some REE-based drugs (particularly the gadolinium-based contrast agents used for magnetic resonance imaging) partially release their REE payload at the expense of endogenous cations like $Zn^{2+}$, $Mg^{2+}$, and $Ca^{2+}$. The issue has recently led to the ban of some these REE-based drugs in Europe and the emission of a safety warning by the US Food and Drug Administration in 2017. The results presented herein demonstrate that bio-sourced chelators can be REE-specific, can withstand large amounts of competing ions, and are more robust than small synthetic molecules.

Example 4—Acid Tolerance and Thermal Stability of Lanmodulin

Figure 6A:
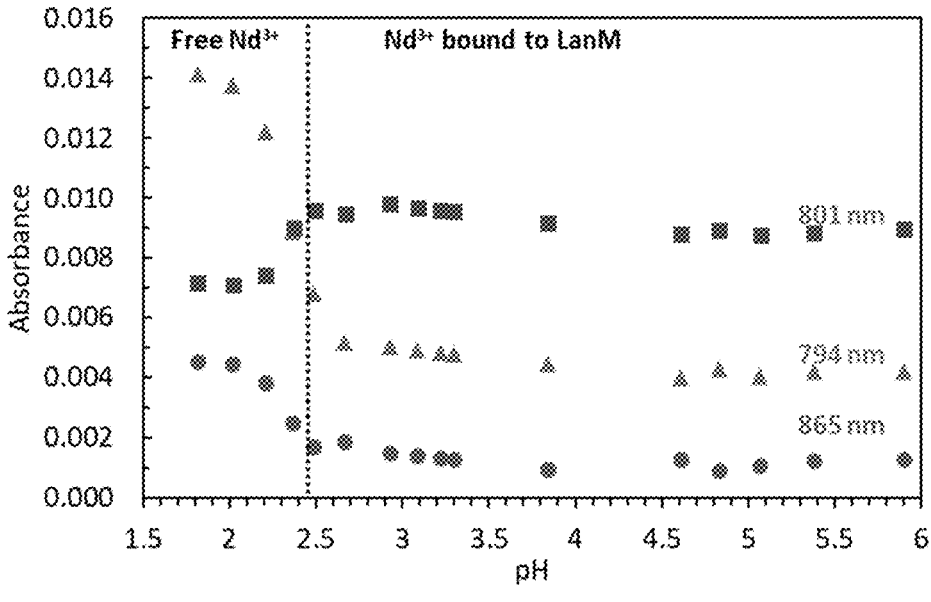
FIG. 6A-FIG. 6D shows the stability of REE-LanM at low pH and the binding of $REE^{3+}$ ions to LanM as a function of pH.
Figure 6B:
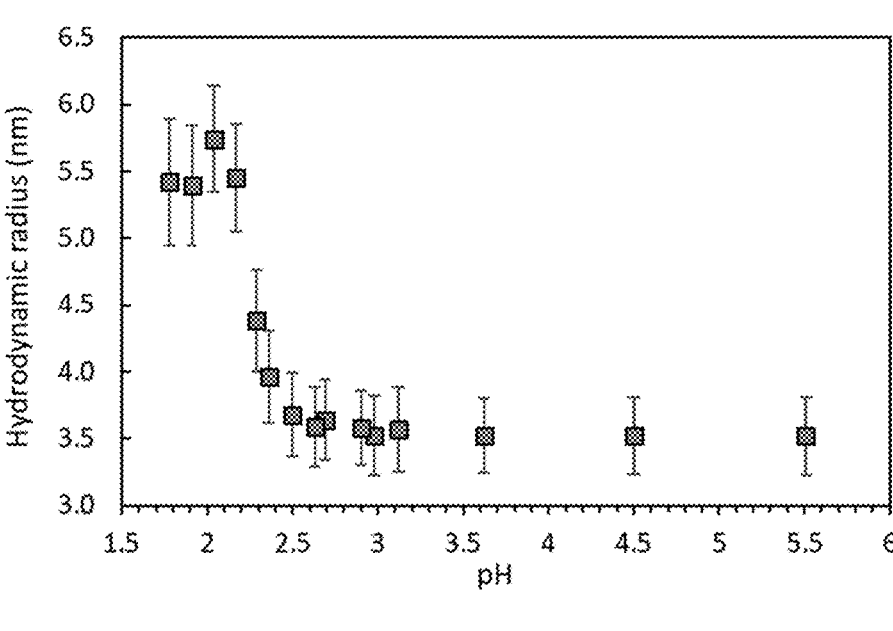
Figures 6C, 6D:
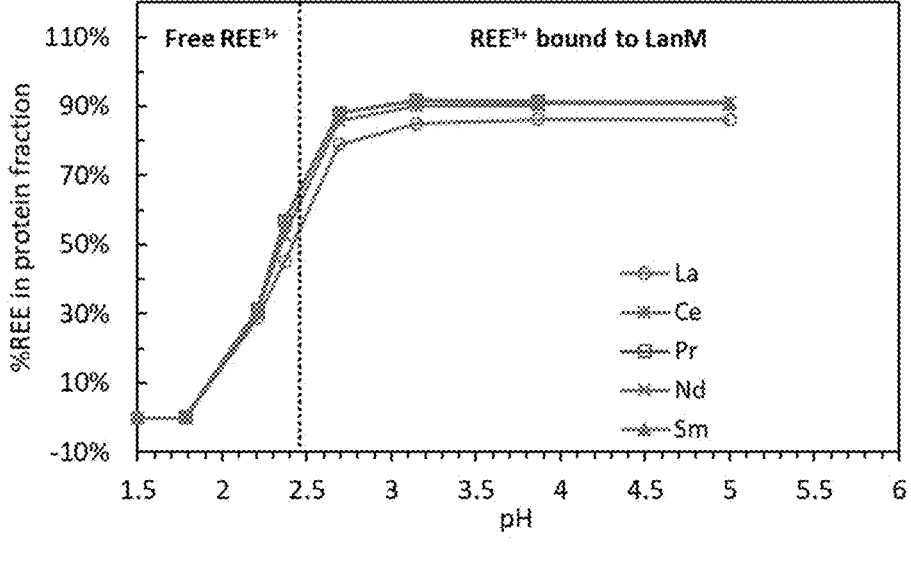
Figure 7A:
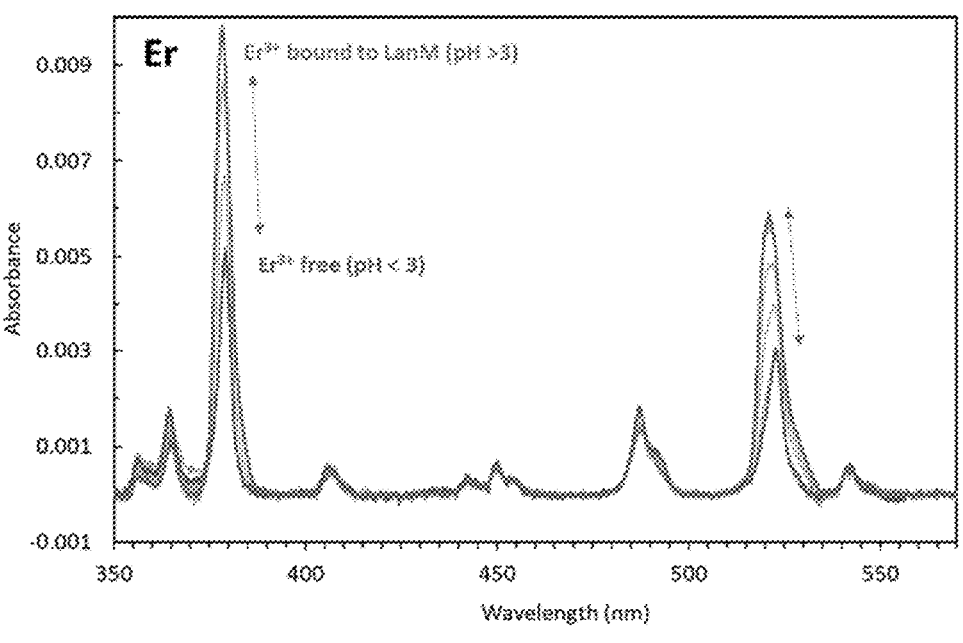
FIG. 7A-FIG. 7H shows the stability of REE-LanM at low pH and the binding of $REE^{3+}$ ions to LanM as a function of pH. [Er], [Nd], [Ho], and [Pr]=1 mM. [LanM]=0.25 mM. Buffer: 20 mM glycine, 10 mM $KCH_3COO$, 70 mM KCl.
Figure 7B:
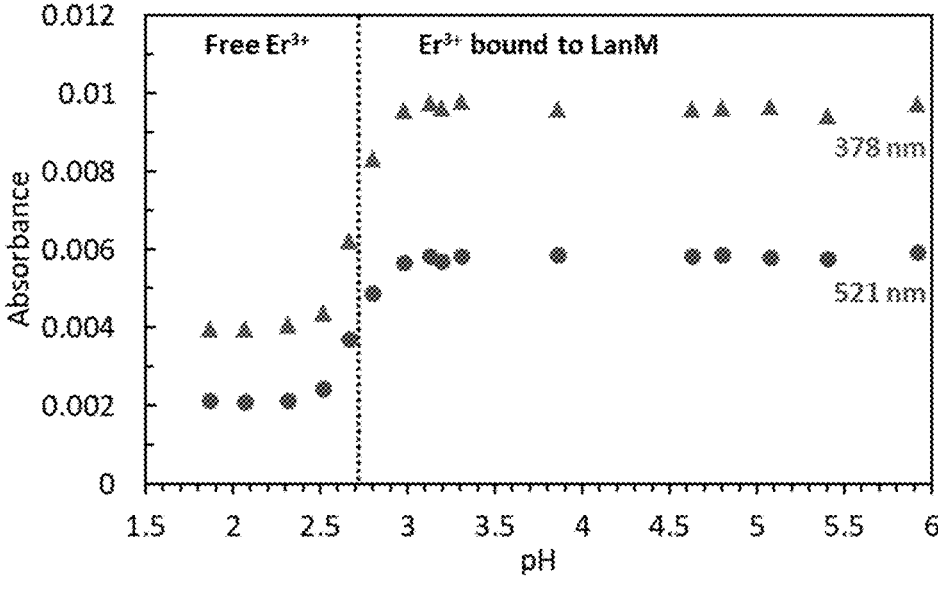
Figure 7C:
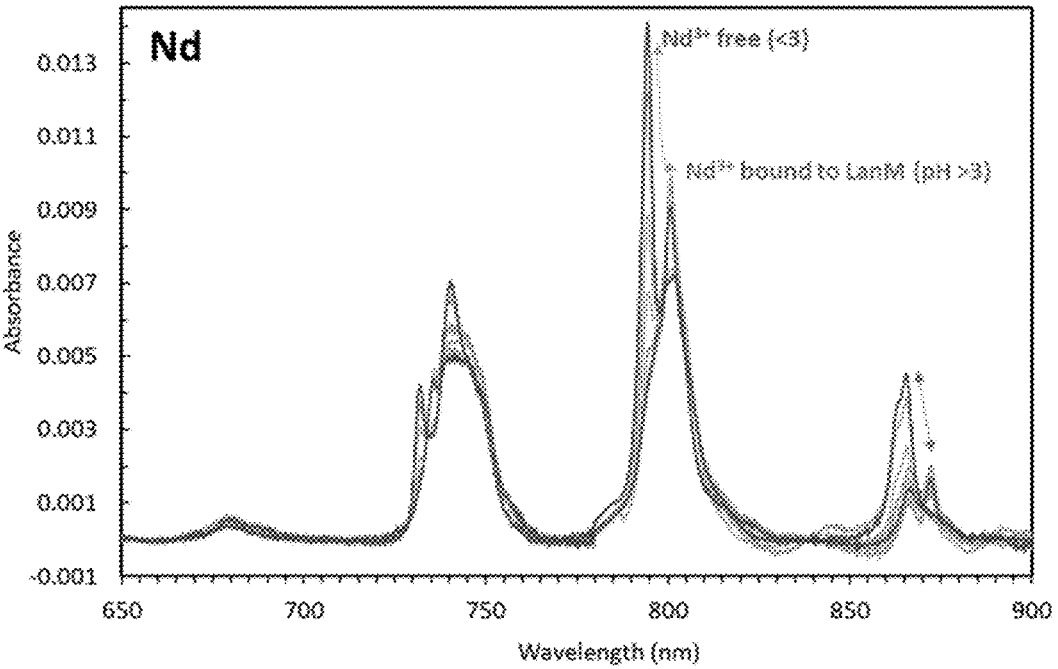
Figure 7D:
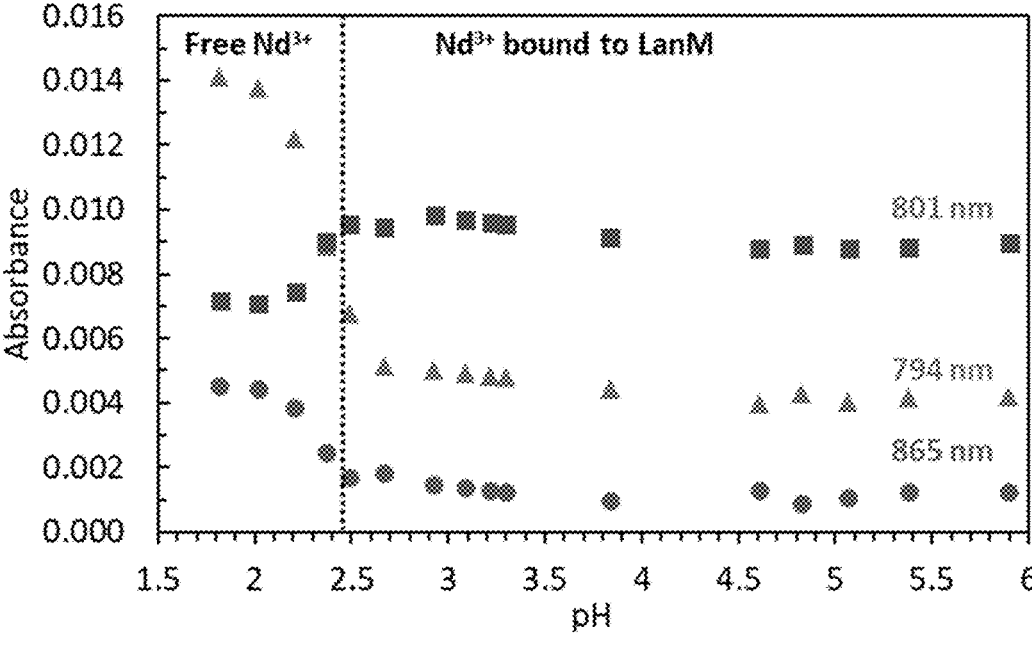
Figure 7E:
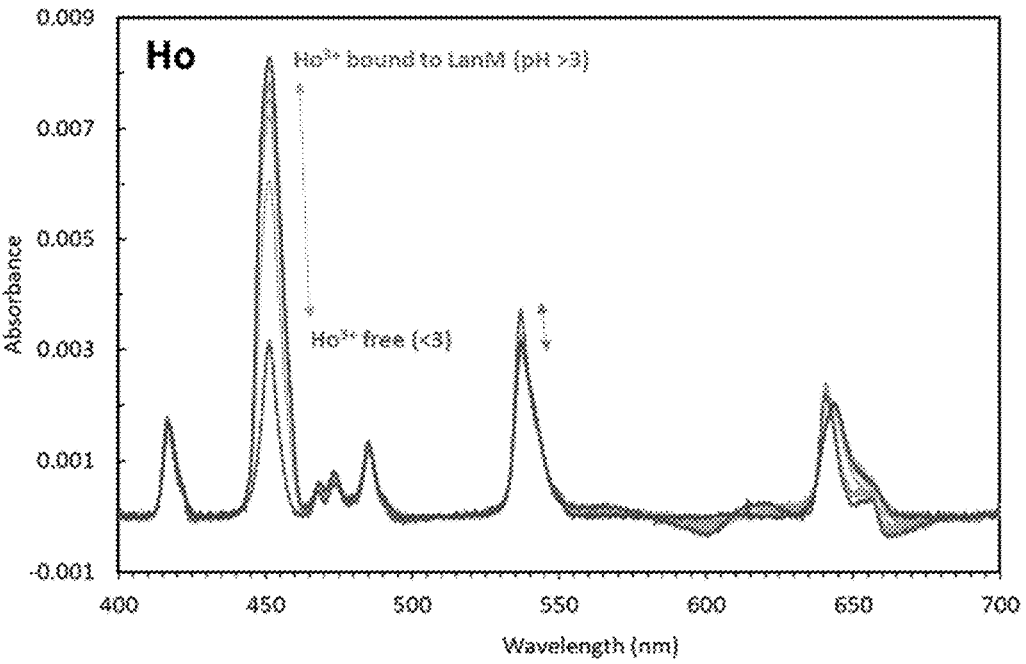
Figure 7F:
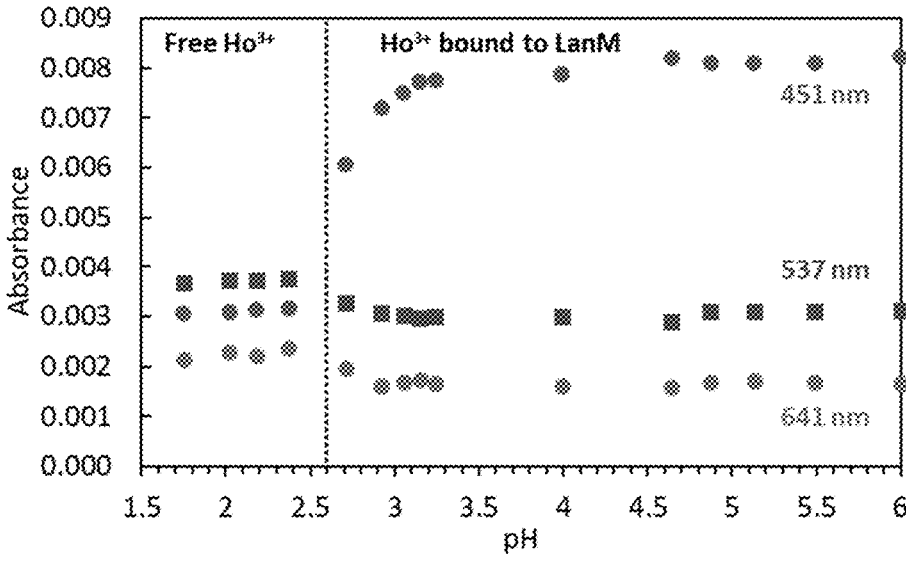
Figure 7G:
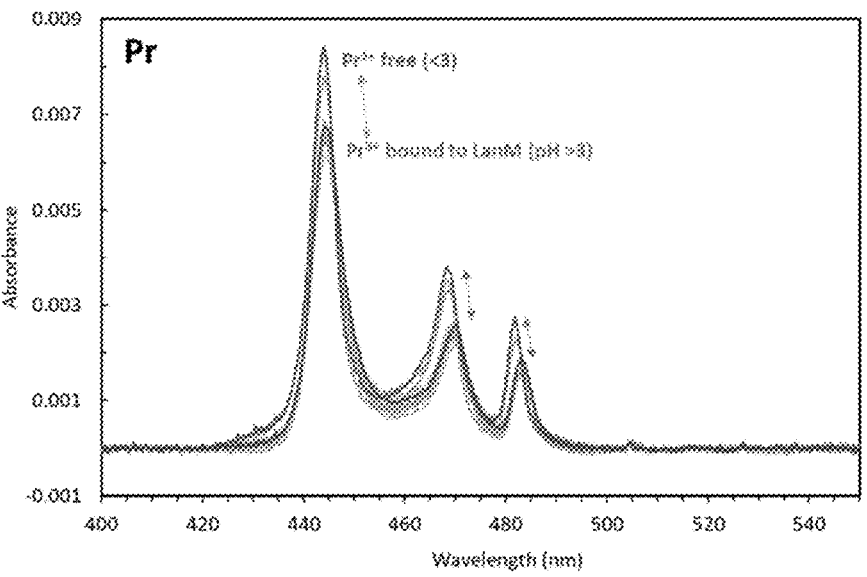
Figure 7H:
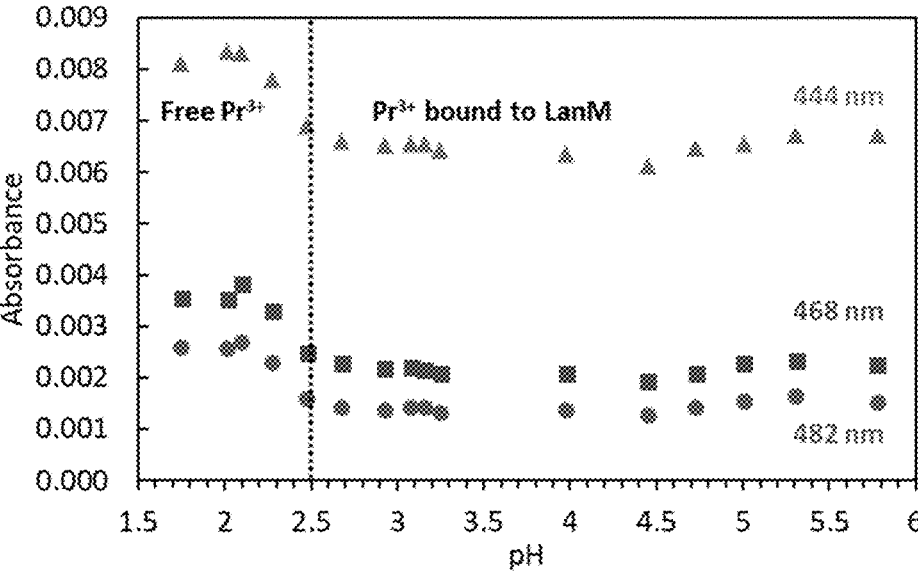

Natural macromolecules were typically considered to be incompatible with harsh chemical conditions such as those encountered in hydrometallurgical processes. Contrary to other known REE-binding proteins, LanM was found remarkably tolerant to acidic conditions. Spectrophotometric titrations of millimolar REE-LanM solutions indicated that REEs remain bound to LanM at pH ~2.5 (FIG. 6(A) and FIG. 7). Dynamic light scattering experiments also revealed a significant increase in the hydrodynamic diameter (from 3.5 to 5.5 nm) of the LanM-REE system when the pH reached ~2.5 (FIG. 6(B)) which suggested the release of the REE ions and opening of the protein. This size change was confirmed to be directly correlated to the REE uptake by LanM. LanM's unprecedented behavior at low pH was further confirmed by size-exclusion ultrafiltration and subsequent analysis of the filtrates (by both ICP-MS and Arsenazo III titrations; FIG. 6(C) and FIG. 6(D)) which afforded a direct confirmation of metal-protein complexation. Even in the micromolar range and with just the stoichiometric amount of LanM, REE ions remained bound to the protein down to PH ~2.5.

Most proteins denature at low pH or release their metals under mildly acidic conditions. The optimal stability for previously studied REE-binding proteins was around the near-neutral physiological pH. For comparison, even if Tf has an extraordinarily high affinity toward ferric iron ($K_d$~$10^{-20}$ M), it releases its metal ion at pH lower than 6 (Dautry-Varsat et al., *PNAS* 80, 2258-2262 (1983)). Similarly, Scn is unable to retain its metal ions under acidic conditions. The $Fe^{3+}$-siderophore-Scn adducts and most $Fe^{3+}$-siderophore complexes, which reputedly drive one of the most stable metal uptake mechanisms found in nature, fall apart between pH 6 and 3.5 (Correnti et al., *J. Biol. Chem.* 287, 13524-13531 (2012)). In the case of CaM, which shares some structural similarities with LanM, it starts releasing $Ca^{2+}$ around pH 6 (Haiech et al., *Biochemistry* 20, 3890-3897 (1981)). Synthetic LBTs are also unable to bind REEs ions below pH 5-6 (Park et al., *Environ. Sci. Technol.* 50, 2735-2742 (2016)).

The performance of LanM at low pH also challenged the general perception that manmade chelators were superior or more robust than natural macromolecules. For example, EDTA and DTPA were used for REE complexation in various applications going from pharmaceutical preparations to the nuclear chemistry field and analytical chemistry but, these synthetic chelators protonated and released their REE ions at pH 2.5 to 3.0. These results corroborated the fact that LanM outperformed chelators like EDTA or EDDS during ligand exchange titrations. The origin of the extreme pH stability of the REE-LanM remained unknown until now. FIG. 6 shows the stability of REE-LanM at low pH.

Figure 8A:
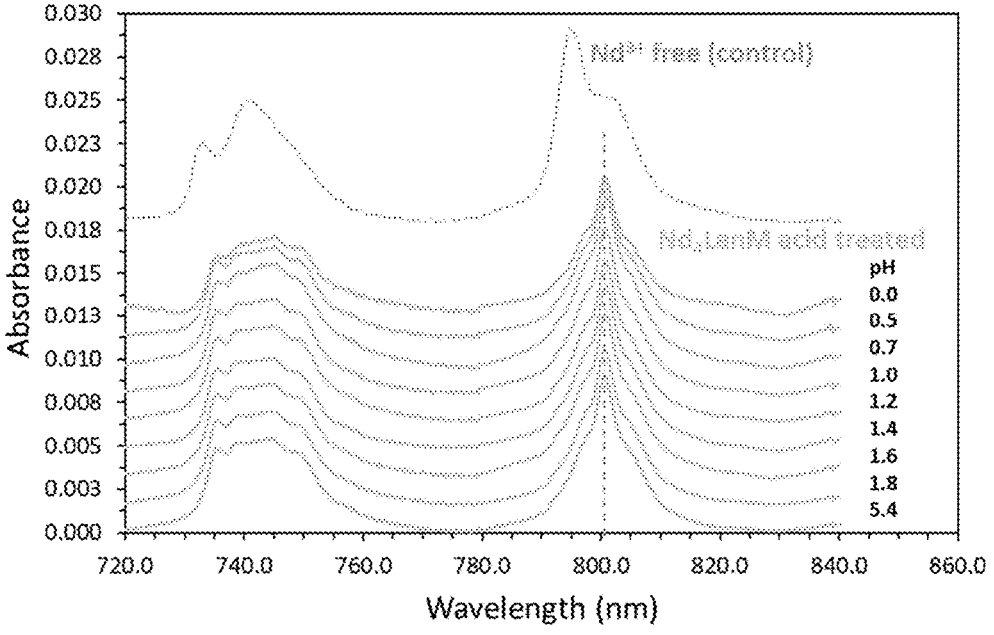
FIG. 8A-FIG. 8B shows the absorbance spectrum and wavelength of the maximum absorbance of an acid treated $Nd_4LanM$ sample. The $Nd_4LanM$ sample was consecutively acidified with 6 M HCl at different pH values (from 5.4 down to 0). After each acidification, the sample was left for at least 1 h, then brought back to PH ~5 (using 6 M NaOH) and its absorbance spectrum was measured. Initial concentrations: [Nd]=1 mM, [LanM]=0.25 mM. Sample corrected for dilution. Control sample: 1 mM $NdCl_3$ in HCl.
Figure 8B:
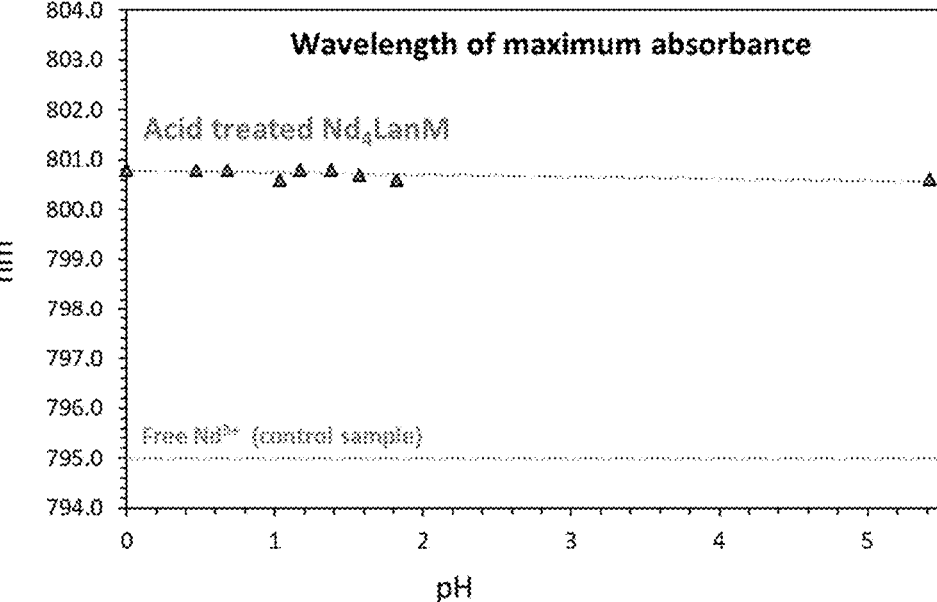
Figures 9A, 9B:
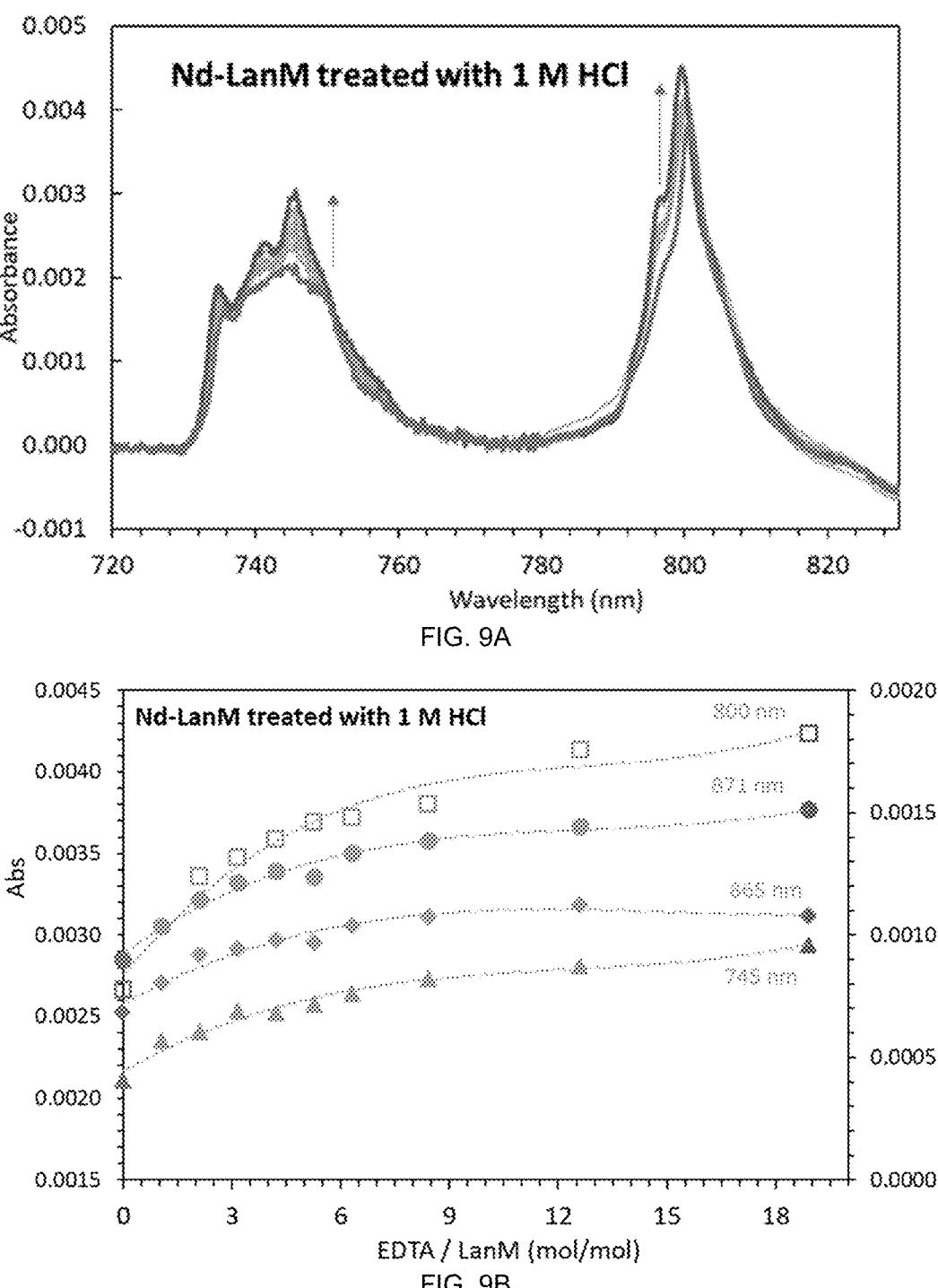
FIG. 9A-FIG. 9D shows the ligand-ligand competition titration between EDTA and acid-treated Nd-LanM and untreated Nd-LanM. Acid-treated Nd-LanM: acidified to pH 0 (1 M HCl) using 6 M HCl, left for 4 hours, and then readjusted to pH 5 using 6 M NaOH. [Nd]=0.48 mM. [LanM]=0.12 mM. [EDTA]=0 to 2.2 mM. pH=5.0. Untreated Nd-LanM: [Nd]=1 mM. [LanM]=0.31 mM. [EDTA]=0 to 4.1 mM. pH=5.0 (25 mM $KCH_3COO$, 75 mM KCl).
Figure 9C:
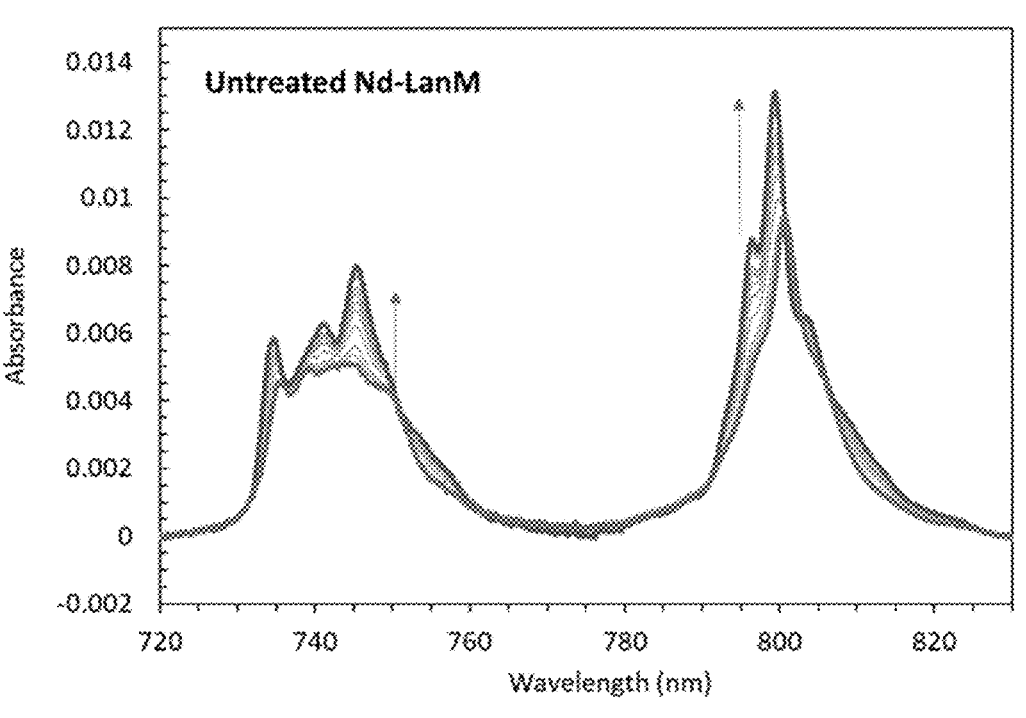
Figure 9D:
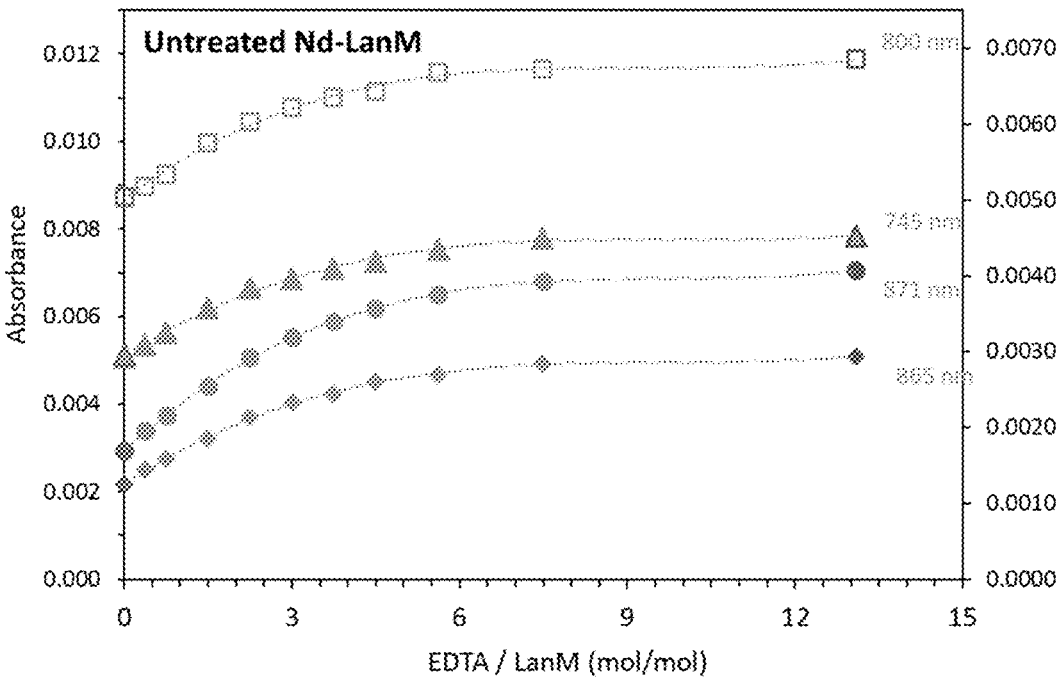
Figures 10, 10A:
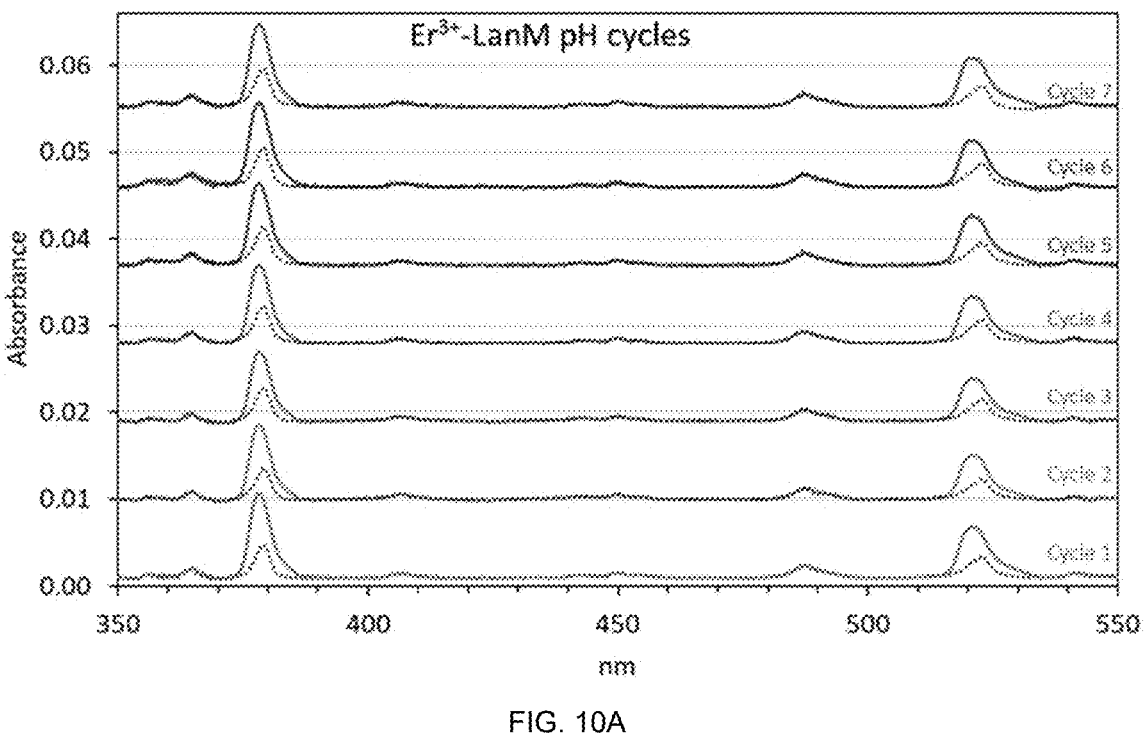
Figure 10C:
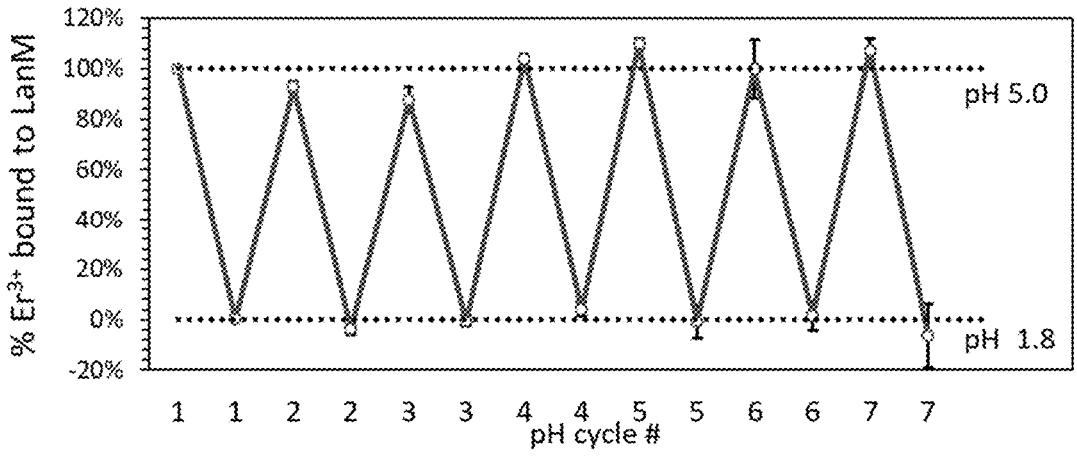
Figure 10D:
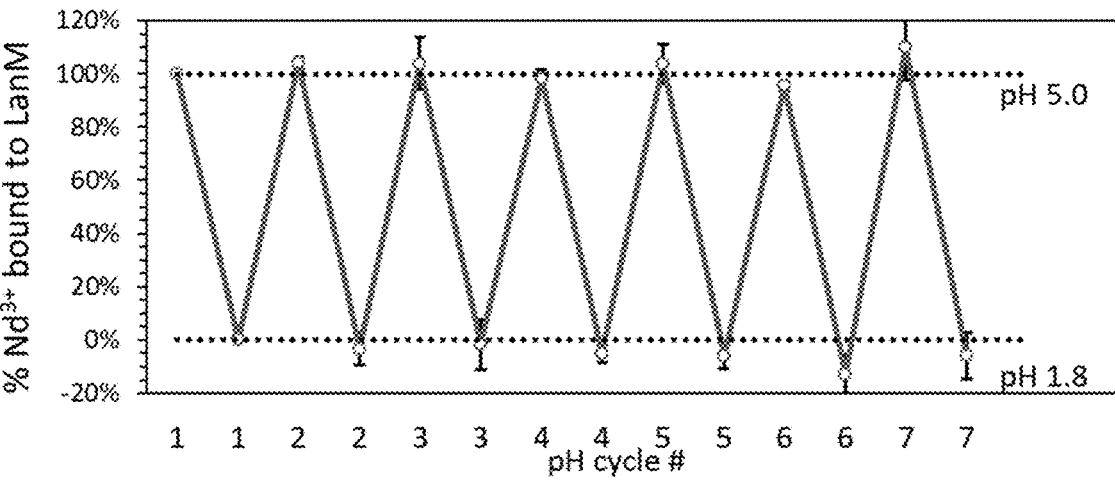

Going one step further, the resilience of LanM to repeated acid attacks was tested. Stoichiometric REE-LanM samples were first acidified to pH 1.8, left for 4 days (harsh conditions compared to normal process operating conditions), and then subjected to successive pH swing cycles below and above pH 2.5. As the LanM-bound and free REE ions had unique UV-vis-NIR absorbance signatures, potential release of the REE ions would have been translated into spectral changes. As shown on FIG. 10, the binding of REE ions to LanM was reversible and the coordination environment of the REE ions was unaffected by multiple pH-triggered complexation and release cycles. Treatment of LanM to even more acidic conditions but far more normal operating conditions (up to 1 M HCl) also showed that LanM was able to recover its affinity for the REEs after it was brought back to pH >2.5 (FIG. 8 and FIG. 9).

Thermal stability is also an important feature for any application relying on metal complexation. In the case of proteins, they are typically thermosensitive and prone to denaturation, aggregation, or precipitation at high temperature. For instance, this represents a major technical hurdle for developing pharmaceuticals that involve proteins and metal ions, including REE-based drugs. Positron electron tomography (i.e. PET imaging) and some cancer radiotherapies like targeted alpha therapy rely on the labeling of protein antibodies with medical radioisotopes such as $^{44}Sc^{3+}$, $^{90}Y^{3+}$, $^{134}Ce^{3+}$, $^{149}Tb^{3+}$, $^{177}Lu^{3+}$, or $^{225}Ac^{3+}$. Unfortunately, radiolabeling procedures often involve high temperature steps that are incompatible with proteins which create difficulties (e.g. low yields) in the preparation of radiopharmaceuticals. Another application where thermal stability is paramount is the extraction of REEs from geothermal fluids. These abundant but currently untapped sources can reach 80° C. and contain sub-ppb to low-ppm levels of REEs which would require very robust ligands for selectively extracting the REEs.

REE-LanM complexes were found thermally stable in solution. Stoichiometric Nd-LanM samples were subject to an aggressive thermal treatment: ten successive periods of 10 hours from 25 to 95° C. As displayed on FIG. 11, no change was detected in the absorbance spectrum indicating that $Nd^{3+}$ remained bound to LanM even after prolonged exposure to elevated temperatures. The integrity of the protein was further confirmed by SDS-PAGE tests. Similar experiments using dynamic light scattering also indicate that the REE-LanM species remain stable throughout the temperature range accessible in water at ambient pressure (FIG. 11). These results highlight the robustness and resilience of the REE-LanM species and the suitability of LanM for chemically demanding applications.

Example 5—LanM Application to Industrial Feedstock

Finally, the unique properties of LanM were tested on industrial REE feedstocks. Non-combusted coal (lignite) and electronic waste (E-waste) are potentially valuable REE sources but they are currently unused. These non-conventional sources are complex mixtures of REE and non-REE materials with a high variability compared to natural REE ores and their processing would require a very robust and versatile purification technology. The metal ion concentrations in the E-waste and lignite leachates spanned over 3 orders of magnitude for the REEs and 4 orders of magnitude of non-REE impurities covering a range from ~10 to 120,000 ppb under the experimental conditions herein. Conventional chelators don't exhibit sufficient selectivity to extract the REEs from such media. As shown on FIG. 12 and FIG. 13, even in industrial matrixes with low REE content and large amounts of impurities (Mg, Ca, Sr, Al, Si, Mn, Fe, Co, Ni, Cu, Zn, and U), LanM selectively scavenged the REEs and doesn't interact with the non-REE elements. Direct addition of LanM into the leachates followed by a classic size-exclusion filtration step affords an all-aqueous one-spot method to selectively recover the REEs from complex industrial streams. After a single step, the recovery yields for the lanthanides were higher than 99.5% in the case of the lignite and 99.8% for the E-waste (ICP-MS limit of quantification reached). Scandium and yttrium were recovered with a 96% yield. These results highlight LanM's unique affinity for the REEs and its lack of interaction with other elements across the periodic table.

Example 6—Americium-LanM

Upon addition of LanM to a solution of $Am^{3+}$ ($^{243}Am$) changes in the absorbance spectra were observed (FIGS.

17a-17b). Since absorbance spectrophotometry probes the coordination sphere of the metal center in contrast to the commonly used protein conformational change or protein fluorescence signals, these spectral perturbations are direct evidence of metal-protein binding. The spectrophotometric titration of $Am^{3+}$ by LanM, shown in FIG. 17A-17B, confirmed the LanM is amenable to bind $Am^{3+}$. These titration experiments were performed at pH 5.0, in $KCl/KCH_3COO$ buffer. The spectral variations (FIG. 17B) also suggest formation of 3:1 complex ($Am_3LanM_1$) under the studied conditions.

$K_d$ Determination of am(III)-LanM Versus am(III)-EDTA (FIG. 18A-18F)

The thermodynamic affinity of LanM for Am(III) was determined by ligand competition titration using EDTA. The displacement of Am(III) from LanM to EDTA was followed by UV-visible-Near Infrared (UV-Vis-NIR) spectrophotometry. The spectral variations upon addition of EDTA to a Am(III)-LanM solution were monitored at three independent spectral windows. The window at 230-350 nm (FIG. 18A) corresponds to the absorbance band of LanM or its complex with Am(III). The window at 495-525 nm (FIG. 18B) corresponds to an absorbance band of the Am(III) complexes (either with LanM or EDTA). The window at 750-850 nm (FIG. 18C) correspond to another absorbance band of the Am(III) complexes (either with LanM or EDTA). By performing incremental additions of EDTA to the Am(III)-LanM solution, there are progressive variations in the absorbance spectra in the three spectral windows (FIG. 18A, 18B, 18C, 18D, 18E, 18F). Since the formation constant of the Am(III) EDTA is known (from the literature-See NIST Critical Database), these spectral variations can be modeled and the formation constant of the Am(III)-LanM complex can be determined.

FIG. 18A-18F shows $K_d$ determination by UV-Vis-NIR spectra. The $K_d$ ($Am^{3+}$-LanM)=4.5 μM (±1.3) at pH of 5.0. This signifies that the LanM is the macromolecule (proteins and peptides included) with the highest affinity for $Am^{3+}$ reported. Comparatively, lanthanide binding tags have $K_d$ of 45 nM at pH of 7 and lanthanide binding tags mutants with $K_d$ of 230 nM to 2690 nM at pH of 7 (Jensen et al., Inorg. Chem., 2011, 50, 7937-7939).

pH Stability of Am(III)-LanM Species. Similar to the Kd determination, the UV-Vis-NIR signal of the Am(III)-LanM complex was monitored to determine its stability as a function of pH. An initial sample containing 243Am(III) and LanM at pH 6 (containing $HEPES/KCH_3COO/Glycine/NaCl$ buffer), was slowly acidified by incremental additions of HCl. After each addition of HCl, the UV-Vis-NIR spectrum of the sample was recorded and the pH was measured. No significant change was observed between pH ~6 and PH ~2.8 indicating that the LanM remains bound to Am(III) under these conditions (FIG. 19A, 19B, 19C).

FIG. 19A-19C show the stability in various pH, wherein the concentration of $^{243}Am$ was $15 \times 10^{-6}$ M and the concentration of LanM was $5 \times 10^{-6}$ M with an activity of about 1 microcurie/sample.

Example 7—Radioactive Metal Separation Using LanM

The actinide-lanmodulin filtration procedure included: 1) the protein (LanM) was mixed with the actinide in various pH buffers (for example, an HCl solution at pH 1; or a 10 mM glycine buffer at pH 2; or 10 mM potassium acetate buffer at pH 5; or HEPES buffer at pH 7; or a combination thereof); 2) the small molecules (i.e., less than 5 kDa) were separated from the macromolecules using size-exclusion filtration; and 3) the radioactivity was determined in each fraction of liquid scintillation counting (LSC). "VivaSpin 500 Filters" manufactured by Viva products were used in the examples below.

The filtration of $^{243}$Am with LanM proceeded as such, wherein the concentration of Am was $1\times10^{-6}$ M, the concentration of LanM was $1\times10^{-5}$ M, and the size exclusion filter has a molecular weight cutoff of 3 kDa. Results were recorded and are shown in FIG. 20. These size filtration results were in line with the UV-Vis-NIR results and demonstrated that LanM remains bounds to Am(III) even at low pH, down to pH ~2.8 under these conditions. The FIG. 21 depicts the half-life of $^{243}$Am, and because of the long half-life of Am-243 (about 7,400 year) and the short half-life of Np-239 (2.35 days), the two isotopes are in secular equilibrium after about 22 days. Therefore, after about 22 days the activity of Am-243 and the activity of Np-239 are about equal. Am-243 sources always contain Np-239 unless the two isotopes have been separated in the past few days, which can be very cumbersome. As such, there is a need to be able to separate the isotopes easily and efficiently. Np-239 also decays to Pu-239 (half-life of 24, 110 years). Therefore, producing pure Np-239 by extraction from Am-243 can also give access to purified samples of Pu-239 by simple decay of Np-239 following its purification from Am-243 using LanM.

Filtration of a Mixture of $^{243}$Am and $^{239}$Np with LanM (FIG. 23)

Samples containing $^{243}$Am(III) and LanM, in the appropriate buffer, were subjected to size filtration using VivaSpin500 filters (cut-off at 3 kDa). The $^{243}$Am material was initially in secular equilibrium with its daughter $^{239}$Np and therefore the initial radiopurity of the sample was only 50% Am-243 and 50% Np-239. After mixing and introduction of the sample in the filter, the sample-loaded filter was centrifugated at 10,000 RPM for about 15 min. This step allowed the sample to elute through the filter's size exclusion membrane. After centrifugation, the low molecular weight compounds passed through the membrane whereas the high-molecular weight compounds are retained at the top of the filter. Following centrifugation, the radioactivity was monitored by LSC over time. FIG. 23 shows that the radioactivity in the low molecular weight fractions decays with a half-life that matches exactly that of Np-239. This demonstrated that Np-239 was separated from Am-243 (which was retained by LanM in the high-molecular weight fraction) and that high-purity Np-239 was obtained using LanM in just 1 step and in a few minutes.

Results: The Am-243 was totally scavenged by the LanM and pure Np-239 was filtered through the size exclusion filtration system in one step, under mild conditions (pH 7, at room temperature) with no redox needed, and without using harsh chemical conditions as often required by conventional separation methods (e.g., liquid-liquid extraction or ion-exchange resins).

FIG. 23 is a graph of the activity of the low molecular weight fraction after filtrations of Am-243 and Np-239.

Separation of a Mixture of $^{90}$Sr and $^{90}$Y with LanM (FIG. 24-26)

Samples containing 90Sr (II)/90Y (III) and LanM, in the appropriate buffer (ex: NaCl/HEPES at pH 7.4 or NaCl/NaCH$_3$COO at pH 5), were subjected to size chromatography using Sephadex G25 PD-10 columns. Sr-90 has a relatively long radioactive half-life (28.9 years) and naturally decays to Y-90 which has half-life (2.7 days). Because of the long half-life of Sr-90 and the short half-life of Y-90, the two isotopes are in secular equilibrium after about 30 days. Y-90 is often used in nuclear medicine and can be harvested from Sr-90. However, the available purifications procedures for Y-90/Sr-90 generators are cumbersome. As such, there is a need to be able to separate the isotopes easily and efficiently. The 90Sr material used in the experiments was initially in secular equilibrium with its daughter 90Y and therefore the initial radiopurity of the sample was only 50% Sr-90 and 50% Y-90. After mixing the samples were introduced in the size exclusion column. The typical volume of the sample was 0.1 to 3 mL. After introduction of the sample, buffer was added to elute the sample through the column. The elution was performed by gravity and at room temperature and ambient pressure. The typical sample volume was less than 1 mL and the total volume eluted through the column was ~10 mL. The elution typically takes about 5 min and can even be fasten if one centrifuges the column instead of using a simple elution by gravity. Fractions were collected, weighted for mass balance purposes, and the radioactivity in each fraction was determined by liquid scintillation counting and gamma spectroscopy (performed by the LLNL's counting facility). The nature of the isotope(s) present in each fraction after elution was determined based on the emission spectra and by evolution of the radioactivity over time (i.e., decay curves). FIG. 24 shows the typical elution profile obtained with this type of radioisotope separations. The first peak (at ~3.5 mL) corresponds to the high-molecular weight compounds. In these examples, the first peak corresponds to excess free LanM and its complexes. The second peak at ~7 mL corresponds to the low molecular weight fraction. In the case of the Y-90/Sr-90 separation, Y-90 eluted in the first peak with LanM whereas Sr-90 elutes in the second peak, affording an easy and fast way to separate and purify these two isotopes.

FIG. 25 and FIG. 26 correspond to the radioactivity profile measured (by LSC) over time for the first peak (LanM fraction) and second peak (low molecular weight fraction), respectively. FIG. 25 demonstrated that high-purity Y-90 was obtained using LanM and the size exclusion chromatography column. After a single elution, the recovery yield for Y-90 was higher than 95% and the radiopurity was higher than 99.9%. Similarly, FIG. 26 demonstrated that the low molecular weight fraction (second peak) contained high purity Sr-90. The measured recovery yield for Sr-90 was higher than 95% and the radiopurity was higher than 99.9%.

Results: The elution curve of the separation of Y-90 and Sr-90 with LanM and a PD-10 column (Cytiva) at pH of 7 is shown FIG. 24. The calculated radiopurity of the $^{90}$Y fraction was >99.8%, as shown in FIG. 25. The calculated radiopurity of the $^{90}$Sr fraction was >99.8%, as shown in FIG. 26.

A different filter was used for the filtration of a mixture of $^{90}$Sr and $^{90}$Y with LanM, depicted in FIG. 27 and the results are shown in FIG. 28-30. The Vivaspin Filter manufactured by VivaProducts was tested. The Sr-90 fraction was >99.9% pure in a single centrifugation step at pH of 7.

Separation of Sr-90 and Y-90 was also observed when using mutants of the LanM protein (3D9N, 3D9H, 3E12Q, and 3E12M). The Vivaspin Filter was used for these separation experiments shown in FIG. 29 and FIG. 30.

The Sr-90 and Y-90 separation described above was also accomplished at extremely low concentrations of Y-90 (e.g., 50 femtomolar concentration). FIG. 31 shows elution curves of the Sr-90 and Y-90 separation with a constant low Y-90 concentration (i.e., 50 femtomolar injected in the column) and varying LanM concentrations (i.e., 10 μM, 1 μM, 100 nM, and 10 nM). FIG. 32 shows elution curves of the Sr-90 and Y-90 separation with varying low Y-90 concentrations (e.g., 100 femtomolar, 50 femtomolar, and 10 femtomolar) and constant LanM concentration (i.e., 1 μM). Despite the extremely low metal concentrations in the tests, the results demonstrated the ability of LanM to scavenge Y-90 and purify it from Sr-90 in a very efficient way.

Separation of a Mixture of $^{228}$Ac and $^{228}$Ra with LanM (FIG. 33-35)

Samples containing $^{228}$Ac (III)/$^{228}$Ra (III) and LanM, in the appropriate buffer (ex: pH 7.2), were subjected to size chromatography using Sephadex G25 PD-10 columns. The $^{228}$Ra and $^{228}$Ac material used in the experiments were initially in secular equilibrium. After mixing, the samples were introduced in the size exclusion column. The typical volume of the sample was 0.1 to 3 mL. After introduction of the sample, buffer was added to elute the sample through the column. The elution was performed by gravity and a room temperature and ambient pressure. The typical total volume eluted through the column was ~10 mL. The elution typically takes about 5 min and can even be fasten if one centrifuges the column instead of using a simple elution by gravity. Fractions were collected, weighted for mass balance purposes, and the radioactivity in each fraction was determined by liquid scintillation counting and gamma spectroscopy (performed by the LLNL's counting facility). The nature of the isotope(s) present in each fraction after elution was determined based on the emission spectra and by evolution of the radioactivity over time (i.e., decay curves). The initial amount of Ac-228 used was about 25 femtomolar and LanM was used in a concentration of 40 micromolar. FIG. 33 shows the elution profile obtained with this type of radioisotope separations. The first peak (at ~4.5 mL) corresponds to the high-molecular weight compounds. In these examples, the first peak corresponds to free LanM and its complexes. The second peak at ~9.5 mL corresponds to the low molecular weight fraction. In this separation, Ac-228 eluted in the first peak with LanM whereas Ra-228 elutes in the second peak, affording an easy and fast way to separate and purify these two isotopes. In this separation, the elution peaks were broadened because the volume of the injected sample was 3 mL, which was close to the bed volume of the column. Even under these non-ideal conditions, the LanM system yielded an effective separation between Ac-228 and the other radioisotopes initially present.

Separation of a Mixture of $^{228}$Ac, $^{228}$Ra, $^{90}$Sr and $^{90}$Y with LanM (FIG. 36-38)

Samples containing $^{228}$Ac(III), $^{228}$Ra(II), $^{90}$Sr(II) and $^{90}$Y(III) and LanM, in the appropriate buffer (ex: NaCl/HEPES at pH 7.4), were subjected to size chromatography using Sephadex G25 PD-10 columns. After mixing, the samples were introduced in the size exclusion column. After introduction of the sample, buffer was added to elute the sample through the column. The elution was performed by gravity and a room temperature and ambient pressure. The typical sample volume was less than 3 mL and the total volume eluted through the column was ~10 mL. The elution typically takes about 5 min and can even be fasten if one centrifuges the column instead of using a simple elution by gravity. Fractions were collected, weighted for mass balance purposes, and the radioactivity in each fraction was determined by liquid scintillation counting and gamma spectroscopy (performed by the LLNL's counting facility). The nature of the isotope(s) present in each fraction after elution was determined based on the emission spectra and by evolution of the radioactivity over time (i.e., decay curves). The initial amount of Ac-228 used was 10 femtomolar, the initial amount of Y-90 used was 100 femtomolar, and LanM was used in a concentration of 10 micromolar. FIG. 36 shows the elution profile obtained with this type of radioisotope separations. The first peak (at ~4 mL) corresponds to the high-molecular weight compounds. In these examples, the first peak corresponds to free LanM and its complexes with Y-90 and Ac-228. The second peak at ~8.5 mL corresponds to the low molecular weight fraction of Sr-90 and Ra-228. In this separation, Ac-228 and Y-90 eluted in the first peak with LanM whereas Ra-228 and Sr-90 elutes in the second peak, affording an easy and fast way to separate and purify these two isotopes. FIG. 38 shows that by tuning the ratio between the isotopes (e.g., 25/75 Y/Ac to 75/25 Y/Ac) the radiopharmaceutical doses to be delivered (to a patient or the like) can be modulated, the duration of the dose can be modulated, and the energy spectrum can be modulated.

Example 8—Separation of Radiometal from a Mixture of Metals

A sample containing a mixture of metals, such as $^{243}$Am and $^{239}$NpO$_2$ is mixed with a LanM formulation to form a solution. The solution is added to a filter, such as a spin filter, and is centrifuged. The metals that do not bind to LanM, such as metals that do not have a 3$^+$ oxidation state, M(III*), are eluted through the filter and recovered from the solution. For example, the $^{239}$NpO$_2$ is eluted through the filter and is recovered from solution as purified $^{239}$NpO$_2$. The $^{243}$Am-LanM did not elute through the filter as its size is too large. There are two options to move forward: 1) add dilute acid, such as HCl or acetate having a pH of 2, to the filter such that the radiometal is desorbed from the LanM and elutes through the filter and is recovered; or, 2) store the filter with the M (III)-LanM for a certain amount of time such that the secular equilibrium between the radiometals is up, such as storing the filter for 22 days after filtering for the $^{243}$Am and $^{239}$NpO$_2$ mixture, and then filter again, collecting the isotope that does not bind or weakly binds to LanM.

A sample containing a mixture of metals, $^{241}$Am$^{3+}$ and $^{241}$Pu$^{4+}$ (or $^{241}$PuO$^{2+}$) is mixed with a LanM formulation to form a solution. The solution is added to a filter, such as a spin filter, and is centrifuged. The $^{241}$Pu$^{4+}$ is eluted through the filter and is recovered from the solution. The $^{241}$Am-LanM does not elute through the filter as its size is too large. There are two options to move forward: 1) add dilute acid, such as HCl, acetate, or glycine having a pH of 2 or less, to the filter such that the $^{241}$Am is desorbed from the LanM and elutes through the filter and is recovered; or, 2) the $^{241}$Am-LanM is further washed with an acetate buffer (pH of 5) to obtain more $^{241}$Pu as well as obtain high-purity $^{241}$Am-LanM.

A sample containing a mixture of metals, Nd$^{3+}$ and $^{241}$Pu$^{4+}$ is mixed with a LanM formulation to form a solution. The solution is added to a filter, such as a spin filter, and is centrifuged. The $^{241}$Pu$^{4+}$ is eluted through the filter and is recovered from the solution. The Nd-LanM does not elute through the filter as its size is too large.

A sample containing a mixture of metals, $^{225}$Ac$^{3+}$, $^{233}$UO$_2$$^{2+}$, $^{229}$Th$^{4+}$, and $^{225}$Ra$^{2+}$, is mixed with a LanM formulation to form a solution. The solution is added to a filter, such as spin filter, and is centrifuged. The $^{233}$UO$^{2+}$, $^{229}$Th$^{4+}$, and $^{225}$Ra$^{2+}$ are eluted through the filter and are recovered from the solution. The $^{225}$Ac-LanM does not elute through the filter as its size is too large. There are three options to move forward: 1) add dilute acid, such as HCl pH of 2, to the filter such that the $^{225}$Ac$^{3+}$ is desorbed from the LanM and elutes through the filter and is recovered; 2) the $^{225}$Ac-LanM is further washed with an acetate buffer (pH of >3) to remove trace amounts of $^{233}UO_2^{2+}$, $^{229}Th^{4+}$, and $^{225}Ra^{2+}$; or, 3) concentrate the $^{225}Ac$-LanM that is recovered from the high molecular weight part of the filter for use.

A sample containing a mixture of metals, $^{225}Ac^{3+}$, $^{233}UO_2^{2+}$, $^{229}Th^{4+}$, and $^{225}Ra^{2+}$, is mixed with a LanM formulation to form a solution. The solution is added to a filter, such as a size exclusive filter or desalting column, and is filtered. The purified $^{225}Ac$-LanM is eluted first and then the $^{233}UO_2^{2+}$, $^{229}Th^{4+}$, and $^{225}Ra^{2+}$ are eluted after through the filter. Both the $^{225}Ac$-LanM and the $^{233}UO_2^{2+}$, $^{229}Th^{4+}$, and $^{225}Ra^{2+}$ are recovered separately from solution.

A sample containing a mixture of metals, $Nd^{3+}$ and $^{241}Pu^{4+}$, is mixed with a LanM formulation to form a solution. The solution is added to a filter, such as a size exclusive filter or desalting column, and is filtered. The purified Nd-LanM is eluted first and then the $^{241}Pu^{4+}$ is eluted after through the filter. Both the Nd-LanM and the $^{241}Pu^{4+}$ are recovered separately from solution.

A sample containing a mixture of metals, $^{44}Sc^{3+}$ and $^{44}Ti^{4+}$, is mixed with a LanM formulation to form a solution. The solution is added to a filter, such as a size exclusive filter or desalting column, and is filtered. The purified $^{44}Sc$-LanM is eluted first and then the purified $^{44}Ti^{4+}$ is eluted after through the filter. Both the $^{44}Sc$-LanM and the $^{44}Ti^{4+}$ are recovered separately from solution.

A sample containing a mixture of metals, $^{90}Y^{3+}$ and $^{90}Sr^{2+}$, is mixed with a LanM formulation to form a solution. The solution is added to a filter, such as a size exclusive filter or desalting column, and is filtered. The purified $^{90}Y$-LanM is eluted first and then the purified $^{90}Sr^{2+}$ is eluted after through the filter. Both the $^{90}Y$-LanM and the $^{90}Sr^{2+}$ are recovered separately from solution.

Example 9—Estimated $K_d$ for Ac₃LanM

Based on the initial elution curves shown in FIG. 39, the estimated stability constant for the Ac₃LanM complex is log Beta about 35.5 (at pH of 7.2) and a $K_d$ of 1.5 μM.

Example 10—Competition of LanM with other Chelators Various Y-90/Sr-90 separations using a PD-10 column with LanM were done as described above with an initial concentration of Y-90 of 100 femtomolar, and LanM of 20 micromolar, at a pH of 7.4, but with the addition of varying concentrations of carbonate anion (e.g., 5 mM, 10 mM, 25 mM, 50 mM, and 100 mM) were added. FIG. 40 shows that even under unfavorable conditions, LanM still competes with chelators to bind Y-90. FIG. 41 shows the percent recovery of Y-90 in the separations versus the concentration of carbonate anion versus LanM. FIG. 41 indicates that a simple solution comprising carbonate can be used to desorb radiometals or REEs in a two-step process: 1) LanM is loaded with Y-90 (or other RM or REE), and 2) the carbonate solution causes the desorption of Y-90 (or other RM or REE) from the LanM such that it can be recovered, and the now pure Y-90 (or RM or REE) is protein-free.

Various Y-90/Sr-90 separations using a PD-10 column with LanM were done as described above with an initial concentration of Y-90 of 100 femtomolar, and LanM of 20 micromolar but with the addition of varying concentrations of phosphate anion were added. FIG. 42 shows that even under unfavorable conditions, LanM still competes with chelators to bind Y-90.

Various Y-90/Sr-90 separations using a PD-10 column with LanM were done as described above with an initial concentration of Y-90 of 100 femtomolar, and LanM of 20 micromolar but with the addition of varying competing chelators at a concentration of 25 mM. FIG. 43 shows that even under unfavorable conditions, LanM still competes with chelators to bind Y-90, and the recovery yields in the presence of all chelators except carbonate was 70% or more. Even with carbonate the recovery yield was about 50%.

Example 11—Recovery of Y-90 in the Presence of Bio-Relevant Cations

Various Y-90/Sr-90 separations using a PD-10 column with LanM were done at a pH of 7.4. The samples were prepared by admixing a Y-90 concentration of 100 femtomolar, a LanM concentration of 20 micromolar, and varying concentration of bio-relevant cations, such as Mg (II), Ca (II), Mn (II), Zn (II), and Cu (II). The concentrations of the bio-relevant cations included 0 micromolar, 1 micromolar, 10 micromolar, 100 micromolar, and 1000 micromolar (for each cation-so the total concentration of competing cations was 0, 5, 50, 500, and 5000 micromolar). FIG. 44 shows the recovery yields of all samples were above 70%. In addition, the separations were also done at varying pH (e.g., 7.4, 7, 6, and 5) with a constant concentration of bio-relevant molecules of 10 micromolar. FIG. 45 shows that the separations were still successful. FIG. 46 shows the Y-90 was above 90% radiopure in all cases. In fact, the radiopurity was higher (>95% pure) at lower pH.

Example 12—Expression and Purification of *M. extorquens* AM1 Lanmodulin

All solid and liquid growth media contain 50 μg/mL kanamycin (Km)

Buffer M1: 50 mM Tris, 10 mM NaCl, 1 mM EDTA, pH 8.0

Buffer M2: 50 mM Tris, 1 M NaCl, 1 mM EDTA, pH 8.0

Buffer M3: 30 mM MOPS, 100 mM KCl, pH 7.0

Protein expression: Chemically competent *E. coli* BL21 (DE3) cells were transformed with pET24a-LanM [this plasmid was analogous to those constructed to express the cytosolic, His6-tagged LanM proteins initially described by Cotruvo and co-workers, JACS 2018, 140, 15056, but without the His tag] and were grown at 37° C. overnight on LB-agar-Km plates. A single colony was used to inoculate 100 mL LB-Km and the culture was shaken at 200 rpm overnight (~16 h) at 37° C. This culture was used to inoculate one 2-L culture (in a 6 L flask) at 50× dilution. The cultures were shaken at 200 rpm (37° C.). At OD600 nm~0.6, LanM expression was induced by adding isopropyl-beta-D-1-thiogalactopyranoside (IPTG) to a concentration of 0.2 mM. After 3 h of induction, the cells were harvested by centrifugation (7 min, 7000×g, 4° C.) and transferred to pre-weighed 50-ml conical tubes. Typical yield is ~2-3 g per L culture. The cell paste was flash frozen in liquid nitrogen and stored at −80° C.

Protein purification: On ice, the cell pellet was resuspended in 5 mL of Buffer M1 per g of cell paste. Buffer M1 was supplemented with 1 protease tablet per 10 mL, DNase (2 U/mL), and phenylmethanesulfonyl fluoride (PMSF, 0.25 mM). The cells were lysed by sonication and pellet insoluble material by centrifugation at 40,000×g, 45 min, 4° C. A 20 mL (2.5×4 cm) Q-Sepharose Fast Flow column was pre-equilibrated in Buffer M1. The lysate was loaded to the column slowly, at ~2 mL/min. The column was slowly washed (2-3 mL/min) with 1 CV Buffer M1. A gradient mixer was filled (e.g., CBS Scientific GM-200) with 80 mL solutions of Buffer M1 and Buffer M2. The gradient was started and the protein was eluted from the Q-Sepharose column at the same flow rate as above. 2 mL fractions in microcentrifuge tubes were collected. It was only necessary to collect fractions for the first half (~80 mL) of the gradient, as LanM eluted with relatively good purity close to the beginning, at ~100-200 mM NaCl. Fractions were screened by SDS-PAGE (16% Tris-Glycine). LanM ran on the gel as a major band just above 10 kDa, in addition to several lower molecular weight bands which derived from multiple conformations of LanM [see Figure S7 in Cotruvo, JACS 2018]. The desired fractions were pooled and concentrated by centrifugal filtration (Amicon Ultra 10 kDa MWCO) to <2 mL.

In order to remove DNA and minor contaminating proteins, the protein solution was loaded onto a HiLoad Superdex 75 pg 16/600 column pre-equilibrated with Buffer M3 and the protein was loaded using a 2 mL capillary loop. The loop was rinsed with 2 mL Buffer M3 and eluted with 1 CV of the same buffer at 0.75 mL/min. The elution was followed at 280 nm and 260 nm, and collected 2 mL fractions. The elution profile was a broad peak between ~60-85 mL on the 120 mL Superdex 75 pg column. LanM-containing fractions were pooled based on SDS-PAGE analysis and concentrated to the desired volume (e.g., 2 mL) by centrifugal filtration (10 kDa MWCO). 5 g Chelex-100 was added to 500 mL Buffer M3 and stirred in a beaker at room temperature. LanM was added to a dialysis cassette (e.g. Slide-a-Lyzer MWCO 3500) or dialysis tubing and dialyzed overnight at room temperature. The protein concentration was determined using $\varepsilon_{275\ nm}=1400\ M^{-1}\ cm^{-1}$.

The foregoing description is given for clearness of understanding only, and no unnecessary limitations should be understood therefrom, as modifications within the scope of the disclosure herein may be apparent to those having ordinary skill in the art.

Throughout this specification and the claims which follow, unless the context requires otherwise, the word "comprise" and variations such as "comprises" and "comprising" will be understood to imply the inclusion of a stated integer or step or group of integers or steps but not the exclusion of any other integer or step or group of integers or steps.

The use of the terms "a," "an," "the," and similar referents in the context of the disclosure herein (especially in the context of the claims) are to be construed to cover both the singular and the plural, unless otherwise indicated. Recitation of ranges of values herein merely are intended to serve as a shorthand method of referring individually to each separate value falling within the range, unless otherwise indicated herein, and each separate value is incorporated into the specification as if it were individually recited herein. The use of any and all examples, or exemplary language (e.g., "such as") provided herein, is intended to better illustrate the disclosure herein and is not a limitation on the scope of the disclosure herein unless otherwise indicated. No language in the specification should be construed as indicating any non-claimed element as essential to the practice of the disclosure herein.

What is claimed:

1. A method of sequestering a target element from a sample, the method comprising:

contacting the sample and a lanmodulin protein (LanM protein) in a first solution such that the target element (TE) binds to the LanM protein to form TE-LanM, wherein the first solution is aqueous and has a pH of 2.5 to 6.5, the target element is selected from a rare-earth element (REE), Bi, Tl, and In, wherein the LanM protein comprises at least one LanM unit, wherein the at least one LanM unit is a portion of the LanM protein comprising at least two EF hand motifs, wherein at least one of the EF hand motifs is of the form SEQ ID NO: 2 and at least two of the EF hand motifs of the LanM protein are separated by a space of 10-15 residues, wherein the LanM protein is selected from:

a) wild-type lanmodulin comprising the sequence of SEQ ID NO: 1, b) homologs of wild-type lanmodulin comprising the at least one LanM unit, and c) a protein having portions comprising the at least one LanM unit;

recovering the TE-LanM from the first solution by separating the TE-LanM from the sample and LanM protein to form a second solution comprising the TE-LanM;

adjusting the pH of the second solution to less than 2.5, wherein at the pH less than 2.5, the TE desorbs from the LanM protein;

separating the LanM protein and the TE; and repeating the contacting, recovering, and adjusting steps with a second sample and the LanM protein at least once.

2. The method of claim 1, wherein the TE is one or more rare earth elements selected from Sc, Y, La, Ce, Pr, Nd, Pm, Sm, Eu, Gd, Tb, Dy, Ho, Er, Tm, Yb, and Lu.

3. The method of claim 1, wherein the contacting step is performed at a temperature of 0° C. to 100° C.

4. The method of claim 1, wherein the contacting step is performed at a pressure of 0.1 atm to 5 atm.

5. The method of claim 1, wherein the LanM protein has a TE selectivity of $10^3$ or more.

6. The method of claim 1, wherein the sample is an industrial feedstock comprising TEs and non-target elements and the industrial feedstock is non-combusted coal, electronic waste, natural waters, waste streams, radioisotope production compositions, industrial effluents, ore deposits, or a combination thereof.

7. The method of claim 1, wherein the recovery yield of TEs from the sample is 80% or more.

8. The method of claim 1, wherein the TE comprises a radioactive isotope selected from one or more of $^{44}$Sc, $^{47}$Sc, $^{90}$Y, $^{134}$Ce, $^{134}$La, $^{86}$Y, $^{88}$Y, $^{139}$Ce, $^{149}$Th, $^{153}$Gd, $^{177}$Lu, $^{165}$Dy, $^{152}$Eu, $^{153}$Sm, $^{147}$Pm, $^{166}$Ho, $^{169}$Yb, $^{176}$Yb, $^{152}$Tb, $^{155}$Tb, and $^{161}$Tb.

9. The method of claim 1, wherein the sample is a pharmaceutical composition.

10. The method of claim 1, wherein the LanM protein includes a homolog of wild-type lanmodulin comprising the sequence selected from the group consisting of: SEQ ID NO: 3, SEQ ID NO: 4, and SEQ ID NO: 5.

* * * * *